US009624287B2

(12) United States Patent
Weiss

(10) Patent No.: US 9,624,287 B2
(45) Date of Patent: Apr. 18, 2017

(54) O-LINKED CARBOHYDRATE-MODIFIED INSULIN ANALOGUES

(71) Applicant: Case Western Reserve University, Cleveland, OH (US)

(72) Inventor: Michael Weiss, Moreland Hills, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 14/416,022

(22) PCT Filed: Jul. 17, 2013

(86) PCT No.: PCT/US2013/050955
§ 371 (c)(1),
(2) Date: Jan. 20, 2015

(87) PCT Pub. No.: WO2014/015078
PCT Pub. Date: Jan. 23, 2014

(65) Prior Publication Data
US 2015/0299287 A1    Oct. 22, 2015

Related U.S. Application Data

(60) Provisional application No. 61/672,711, filed on Jul. 17, 2012, provisional application No. 61/693,997, filed on Aug. 28, 2012.

(51) Int. Cl.
*A61K 38/28* (2006.01)
*C07K 14/62* (2006.01)
*A61K 38/00* (2006.01)

(52) U.S. Cl.
CPC ............. *C07K 14/62* (2013.01); *A61K 38/00* (2013.01)

(58) Field of Classification Search
None
See application file for complete search history.

(56) References Cited

U.S. PATENT DOCUMENTS

| 7,396,903 | B2 | 7/2008 | Bogsnes et al. |
| 2009/0011976 | A1 | 1/2009 | Ludvigsen et al. |
| 2010/0298212 | A1 | 11/2010 | Miao et al. |
| 2011/0077196 | A1 | 3/2011 | Weiss |
| 2011/0136736 | A1 | 6/2011 | Borowicz et al. |
| 2013/0085101 | A1* | 4/2013 | Weiss .................... A61K 38/28 514/6.2 |

FOREIGN PATENT DOCUMENTS

| WO | 90/10645 A1 | 9/1990 | |
| WO | 2011028813 A2 | 3/2011 | |
| WO | WO2011103575 | * 8/2011 | ............. A61K 38/28 |
| WO | 2014/071405 A2 | 5/2014 | |

OTHER PUBLICATIONS

Betts et al. Amino Acid Properties and Consequences of Substitutions. Bioinformatics for Geneticists. Chapter 14. 2003. pp. 289-316.*
Structure of Lysine. Chemspider. Accessed online at http://www.chemspider.com/Chemical-Structure.5747.html on Aug. 2, 2016, 3 pages.*
Structure of Ornithine. Chemspider. Accessed online at http://www.chemspider.com/Chemical-Structure.6026.html on Aug. 2, 2016, 3 pages.*
Baudys, M; Uchio, T.; Hovgaard, L.; Zhu, E.F.; Avramoglou, T.; Jozefowicz, M.; Rihova, B.; Park, J.Y.; Lee, H.K.; Kim. S.W., "Glycosylated insulins," Journal of Controlled Release 36 (1995) 151-157.
Berenson, Daniel F.; Weiss, Allison R; Wan, Zhu-Li; Weiss, Michael A.; "Insulin analogs for the treatment of diabetes mellitus: therapeutic applications of protein engineering," NIH Public Access Author Manuscripts—Ann. NY Acad Sci, Dec. 2011, pp. 1-28.
Brownlee, Michael and Cerami, Anthony, "A Glucose-Controlled Insulin-Delivery System: Semisynthetic Insulin Bound to Lectin," Science, vol. 206, Dec. 7, 1979, pp. 1190-1191.
PCT/US2013/050955 International Search Report and Written Opinion dated Dec. 6, 2013.

* cited by examiner

Primary Examiner — Marcela M Cordero Garcia
(74) Attorney, Agent, or Firm — Hahn Loeser & Parks LLP

(57) ABSTRACT

An insulin analogue comprises an insulin B-chain polypeptide modified with an O-linked monosaccaride pyranoside adduct at the side chain of residue B27 or an O-linked monosaccaride pyranoside adduct at the side chain of residue B30, or both, where the positions are recited relative to human insulin. The monosaccaride may be a manopyranoside, an N-acetyl-galactopyranoside, or a glucopyranoside. The insulin analogue may additionally comprise containing a foreshortened B-chain polypeptide lacking residues B1-B3, an extension of 1 or 2 Glu residues on the carboxy terminal end of the B-chain polypeptide, an extension of ornithine at the carboxy-terminal end of the B-chain, the substitutions Lys at position B28 and Pro at position B29, an ornithine substitution at position B29, or combinations thereof. The analogue may be an analogue of a mammalian insulin, such as human insulin. A method of treating a patient comprises administering a physiologically effective amount of the insulin analogue.

20 Claims, 17 Drawing Sheets

PROINSULIN

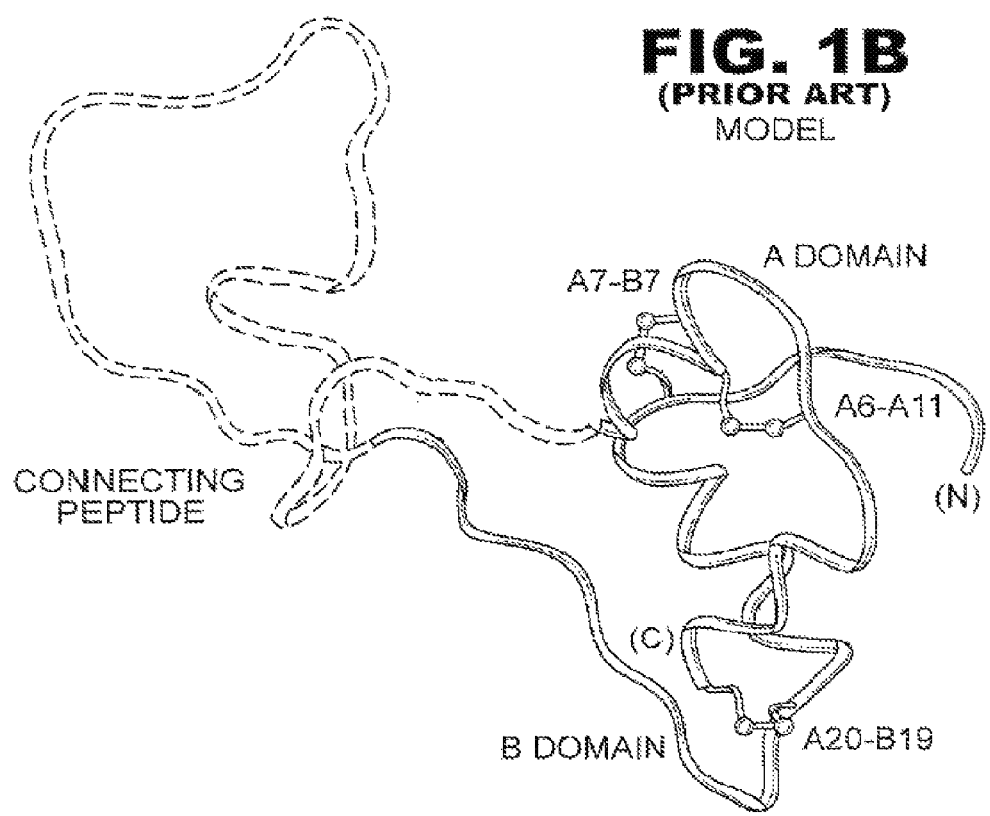

mannosepyranoside**

N-acetylgalactosepyranoside-O-linkage

FIG. 3A,B
(MODEL)
O$^\gamma$-mannosyl-The$^{B27}$-insulin (monomer)
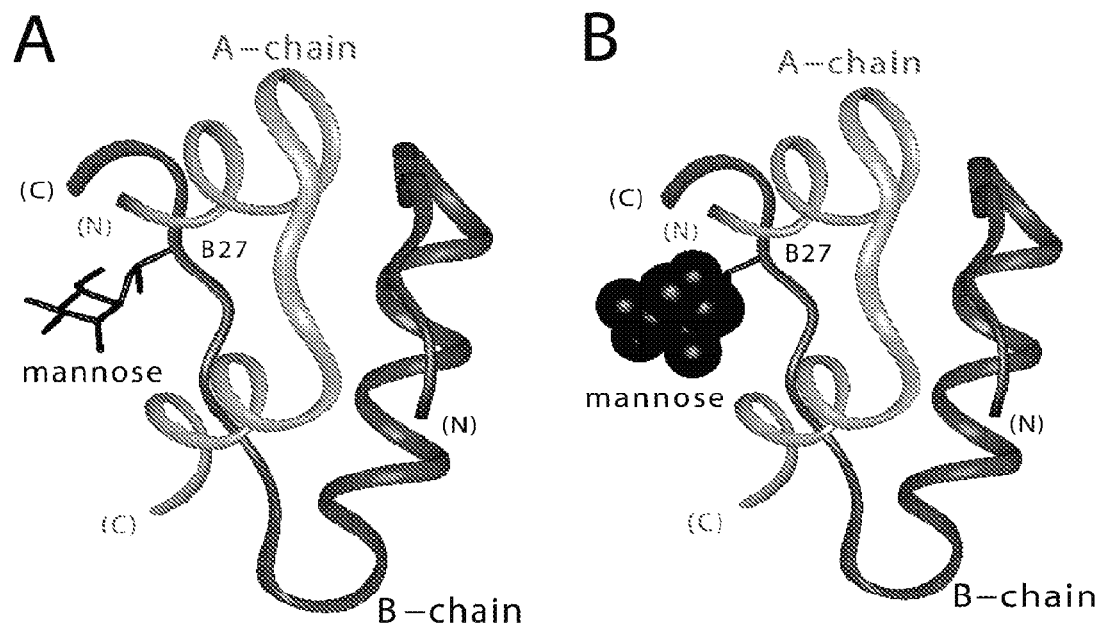

FIG. 4A,B
(MODEL)
O$^\gamma$-mannosyl-The$^{B27}$-insulin (dimer)
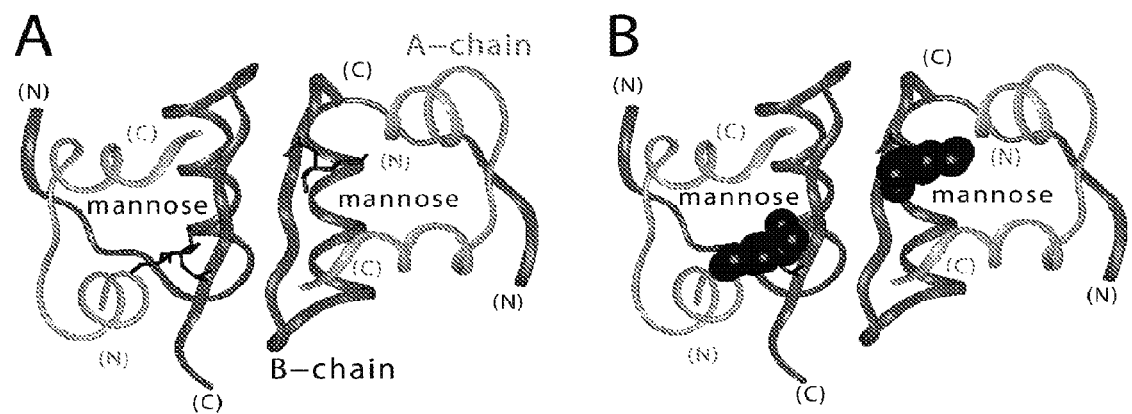

**FIG. 5A,B
(MODEL)
O^γ-mannosyl-The^{B27}-insulin (hexamer)**
A
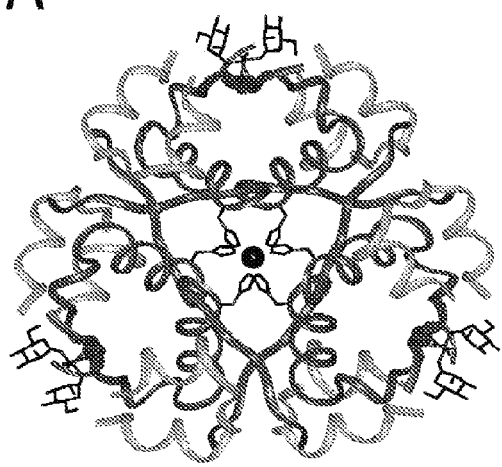
B
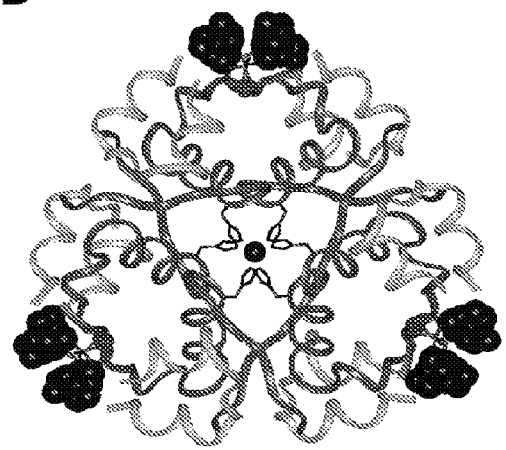

receptor-binding studies low-dose rat studies high-dose rat studies

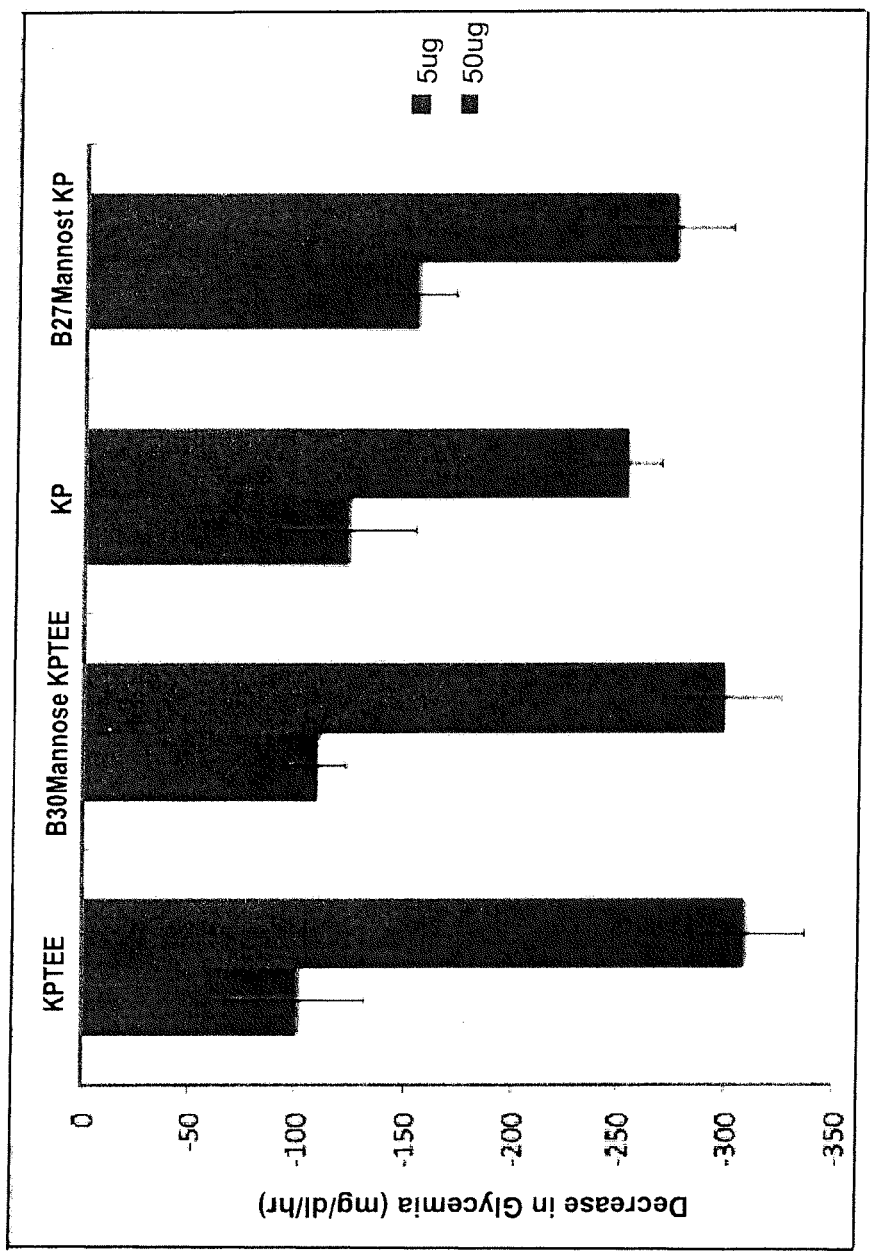

kinetics of insulin hexamer disassembly kinetics of insulin hexamer disassembly Receptor-binding assays STZ rat studies kinetics of insulin hexamer disassembly

SEQUENCE LISTING

<160> NUMBER OF SEQ ID NOS: 79

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is any amino acid.

<400> SEQUENCE: 4

Phe Val Glu Gln His Leu Cys Gly Ser Xaa Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 5
<211> LENGTH: 32
<212> TYPE: PRT
<213> ORGANISM: Homo sapiens

-continued

<400> SEQUENCE: 5

Phe Val Glu Gln His Leu Cys Gly Ser His Leu Val Glu Ala Leu Tyr
1               5                   10                  15

Leu Val Cys Gly Glu Arg Gly Phe Phe Tyr Thr Lys Pro Thr Glu Glu
            20                  25                  30

<210> SEQ ID NO 6
<211> LENGTH: 31
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is any amino acid.
<220> FEATURE:
<221> NAME/KEY: MISC_FEATURE
<222> LOCATION: (29)..(29)
<223> OTHER INFORMATION: Xaa is Ornithine.
<220> FEATURE:
<221> NAME/KEY: MISC_FEATURE
<222> LOCATION: (31)..(31)
<223> OTHER INFORMATION: Xaa is Ornithine.

<400> SEQUENCE: 6

Phe Val Glu Gln His Leu Cys Gly Ser Xaa Leu Val Glu Ala Leu Tyr
1               5                   10                  15

Leu Val Cys Gly Glu Arg Gly Phe Phe Tyr Thr Pro Xaa Thr Xaa
            20                  25                  30

<210> SEQ ID NO 7
<211> LENGTH: 30
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa is an O-Beta Thr linked monosaccharide
      pyranoside selected from a group consisting of  alpha-D
      mannopyranoside, alpha-D glucopyranoside, or N acetyl-Beta
      D galactopyranoside.

<400> SEQUENCE: 7

Phe Val Glu Gln His Leu Cys Gly Ser His Leu Val Glu Ala Leu Tyr
1               5                   10                  15

Leu Val Cys Gly Glu Arg Gly Phe Phe Tyr Xaa Lys Pro Thr
            20                  25                  30

<210> SEQ ID NO 8
<211> LENGTH: 30
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa is an O-Beta Ser linked monosaccharide
      pyranoside selected from a group consisting of  alpha-D
      mannopyranoside, alpha-D glucopyranoside, or N acetyl-Beta  D
      galactopyranoside.

<400> SEQUENCE: 8

Phe Val Glu Gln His Leu Cys Gly Ser His Leu Val Glu Ala Leu Tyr
1               5                   10                  15

Leu Val Cys Gly Glu Arg Gly Phe Phe Tyr Xaa Lys Pro Thr
            20                  25                  30

<210> SEQ ID NO 9

```
<211> LENGTH: 30
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa can be any amino acid.
<220> FEATURE:
<221> NAME/KEY: MISC_FEATURE
<222> LOCATION: (27)..(27)
<223> OTHER INFORMATION: Xaa is an O-Beta Ser linked monosaccaride
      pyranoside selected from a group consisting of  alpha-D
      mannopyranoside, alpha-D glucopyranoside, or N acetyl-Beta
      D galactopyranoside.

<400> SEQUENCE: 9

Phe Val Glu Gln His Leu Cys Gly Ser Xaa Leu Val Glu Ala Leu Tyr
1               5                   10                  15

Leu Val Cys Gly Glu Arg Gly Phe Phe Tyr Xaa Lys Pro Thr
            20                  25                  30

<210> SEQ ID NO 10
<211> LENGTH: 32
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is any amino acid.
<220> FEATURE:
<221> NAME/KEY: MISC_FEATURE
<222> LOCATION: (27)..(27)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(32)
<223> OTHER INFORMATION: Xaa is a two residue extension of the B chain
      containing at least one acidic residue (Glu or Asp).

<400> SEQUENCE: 10

Phe Val Glu Gln His Leu Cys Gly Ser Xaa Leu Val Glu Ala Leu Tyr
1               5                   10                  15

Leu Val Cys Gly Glu Arg Gly Phe Phe Tyr Xaa Lys Pro Thr Xaa Xaa
            20                  25                  30

<210> SEQ ID NO 11
<211> LENGTH: 30
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is any amino acid.
<220> FEATURE:
<221> NAME/KEY: MISC_FEATURE
<222> LOCATION: (27)..(27)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Pro, Ala or a basic residue selected
      from the group Lys, norleucine, Ornithine, diaminobutyric acid or
      diaminopropionic acid.

<400> SEQUENCE: 11

Phe Val Glu Gln His Leu Cys Gly Ser Xaa Leu Val Glu Ala Leu Tyr
```

```
1               5                   10                  15
Leu Val Cys Gly Glu Arg Gly Phe Phe Tyr Xaa Asp Xaa Thr
            20                  25                  30

<210> SEQ ID NO 12
<211> LENGTH: 27
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is any amino acid.
<220> FEATURE:
<221> NAME/KEY: MISC_FEATURE
<222> LOCATION: (24)..(24)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.

<400> SEQUENCE: 12

Gln His Leu Cys Gly Ser Xaa Leu Val Glu Ala Leu Tyr Leu Val Cys
1               5                   10                  15

Gly Glu Arg Gly Phe Phe Tyr Xaa Pro Glu Thr
            20                  25

<210> SEQ ID NO 13
<211> LENGTH: 32
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is any amino acid.
<220> FEATURE:
<221> NAME/KEY: MISC_FEATURE
<222> LOCATION: (24)..(24)
<223> OTHER INFORMATION: Xaa is cyclohexanylalanine.
<220> FEATURE:
<221> NAME/KEY: MISC_FEATURE
<222> LOCATION: (27)..(27)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(32)
<223> OTHER INFORMATION: Xaa is a two residue extension of the B chain
      containing at least one acidic residue (Glu or Asp).

<400> SEQUENCE: 13

Phe Val Glu Gln His Leu Cys Gly Ser Xaa Leu Val Glu Ala Leu Tyr
1               5                   10                  15

Leu Val Cys Gly Glu Arg Gly Xaa Phe Tyr Xaa Lys Pro Thr Xaa Xaa
            20                  25                  30

<210> SEQ ID NO 14
<211> LENGTH: 30
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is any amino acid.
<220> FEATURE:
<221> NAME/KEY: MISC_FEATURE
<222> LOCATION: (24)..(24)
<223> OTHER INFORMATION: Xaa is cyclohexanylalanine.
<220> FEATURE:
<221> NAME/KEY: MISC_FEATURE
```

```
<222> LOCATION: (27)..(27)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Pro, Ala or a basic residue selected
      from the group Lys, norleucine, Ornithine, diaminobutyric acid or
      diaminopropionic acid.

<400> SEQUENCE: 14

Phe Val Glu Gln His Leu Cys Gly Ser Xaa Leu Val Glu Ala Leu Tyr
1               5                   10                  15

Leu Val Cys Gly Glu Arg Gly Xaa Phe Tyr Xaa Asp Xaa Thr
            20                  25                  30

<210> SEQ ID NO 15
<211> LENGTH: 27
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is any amino acid.
<220> FEATURE:
<221> NAME/KEY: MISC_FEATURE
<222> LOCATION: (21)..(21)
<223> OTHER INFORMATION: Xaa is cyclohexanylalanine.
<220> FEATURE:
<221> NAME/KEY: MISC_FEATURE
<222> LOCATION: (24)..(24)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.

<400> SEQUENCE: 15

Gln His Leu Cys Gly Ser Xaa Leu Val Glu Ala Leu Tyr Leu Val Cys
1               5                   10                  15

Gly Glu Arg Gly Xaa Phe Tyr Xaa Pro Glu Thr
            20                  25

<210> SEQ ID NO 16
<211> LENGTH: 32
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is any amino acid.
<220> FEATURE:
<221> NAME/KEY: MISC_FEATURE
<222> LOCATION: (24)..(24)
<223> OTHER INFORMATION: Xaa is a non-standard derivative of Phe.
<220> FEATURE:
<221> NAME/KEY: MISC_FEATURE
<222> LOCATION: (27)..(27)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(32)
<223> OTHER INFORMATION: Xaa is a two residue extension of the B chain
      containing at least one acidic residue (Glu or Asp).

<400> SEQUENCE: 16

Phe Val Glu Gln His Leu Cys Gly Ser Xaa Leu Val Glu Ala Leu Tyr
1               5                   10                  15
```

-continued

```
Leu Val Cys Gly Glu Arg Gly Xaa Phe Tyr Xaa Lys Pro Thr Xaa Xaa
            20                  25                  30

<210> SEQ ID NO 17
<211> LENGTH: 30
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is an amino acid.
<220> FEATURE:
<221> NAME/KEY: MISC_FEATURE
<222> LOCATION: (24)..(24)
<223> OTHER INFORMATION: Xaa is a halogenated derivative of Phe selected
      from the group consisting of 2 CH3 Phe, 3 CH3 Phe, 4 CH3 Phe,
      pentafluoro Phe, 2F Phe, 3F Phe, 2 Cl Phe, 3 Cl Phe, 4 Cl Phe, 2
      Br Phe, 3 Br Phe, and 4 Br Phe.
<220> FEATURE:
<221> NAME/KEY: MISC_FEATURE
<222> LOCATION: (27)..(27)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Pro, Ala or a basic residue selected
      from the group Lys, norleucine, Ornithine, diaminobutyric acid or
      diaminopropionic acid.

<400> SEQUENCE: 17

Phe Val Glu Gln His Leu Cys Gly Ser Xaa Leu Val Glu Ala Leu Tyr
1               5                   10                  15

Leu Val Cys Gly Glu Arg Gly Xaa Phe Tyr Xaa Asp Xaa Thr
            20                  25                  30

<210> SEQ ID NO 18
<211> LENGTH: 27
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is any amino acid.
<220> FEATURE:
<221> NAME/KEY: MISC_FEATURE
<222> LOCATION: (22)..(22)
<223> OTHER INFORMATION: Xaa is 2 CH3 Phe, 3 CH3 Phe, 4 CH3 Phe, or a
      halogenated derivative of Phe selected from the group consisting
      of pentafluoro Phe, 2F Phe, 3F Phe, 2 Cl Phe, 3 Cl Phe, 4 Cl Phe,
      2 Br Phe, 3 Br Phe, and 4 Br Phe.
<220> FEATURE:
<221> NAME/KEY: MISC_FEATURE
<222> LOCATION: (24)..(24)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.

<400> SEQUENCE: 18

Gln His Leu Cys Gly Ser Xaa Leu Val Glu Ala Leu Tyr Leu Val Cys
1               5                   10                  15

Gly Glu Arg Gly Phe Xaa Tyr Xaa Pro Glu Thr
            20                  25

<210> SEQ ID NO 19
<211> LENGTH: 30
<212> TYPE: PRT
<213> ORGANISM: Homo sapiens
```

```
<220> FEATURE:
<221> NAME/KEY: MISC_FEATURE
<222> LOCATION: (5)..(5)
<223> OTHER INFORMATION: Xaa is Asp or Glu.
<220> FEATURE:
<221> NAME/KEY: MISC_FEATURE
<222> LOCATION: (10)..(10)
<223> OTHER INFORMATION: Xaa is Asp or Glu.
<220> FEATURE:
<221> NAME/KEY: MISC_FEATURE
<222> LOCATION: (24)..(24)
<223> OTHER INFORMATION: Xaa is a halogenated derivative of Phe selected
      from the group consisting of 2 CH3 Phe, 3 CH3 Phe, 4 CH3 Phe,
      pentafluoro Phe, 2F Phe, 3F Phe, 2 Cl Phe, 3 Cl Phe, 4 Cl Phe, 2
      Br Phe, 3 Br Phe, and 4 Br Phe.
<220> FEATURE:
<221> NAME/KEY: MISC_FEATURE
<222> LOCATION: (27)..(27)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (28)..(29)
<223> OTHER INFORMATION: Xaa is Lys Pro, Lys Ala, Asp Pro, Asp Lys, Asp
      Ornithine, Asp diaminobutyric acid, Asp diaminopropionic acid, or
      Asp Norleucine.

<400> SEQUENCE: 19

Phe Val Glu Gln Xaa Leu Cys Gly Ser Xaa Leu Val Glu Ala Leu Tyr
1               5                   10                  15

Leu Val Cys Gly Glu Arg Gly Xaa Phe Tyr Xaa Xaa Xaa Thr
            20                  25                  30

<210> SEQ ID NO 20
<211> LENGTH: 31
<212> TYPE: PRT
<213> ORGANISM: Homo sapiens
<220> FEATURE:
<221> NAME/KEY: MISC_FEATURE
<222> LOCATION: (28)..(29)
<223> OTHER INFORMATION: Xaa is Lys Pro, Lys Ala, Asp Pro, Asp Lys, Asp
      Ornithine, Asp diaminobutyric acid, Asp diaminopropionic acid, or
      Asp Norleucine.
<220> FEATURE:
<221> NAME/KEY: MISC_FEATURE
<222> LOCATION: (30)..(30)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Glu or Asp.

<400> SEQUENCE: 20

Phe Val Glu Gln His Leu Cys Gly Ser His Leu Val Glu Ala Leu Tyr
1               5                   10                  15

Leu Val Cys Gly Glu Arg Gly Phe Phe Tyr Thr Xaa Xaa Xaa Xaa
            20                  25                  30

<210> SEQ ID NO 21
<211> LENGTH: 32
<212> TYPE: PRT
<213> ORGANISM: Homo sapiens
<220> FEATURE:
<221> NAME/KEY: MISC_FEATURE
<222> LOCATION: (28)..(29)
<223> OTHER INFORMATION: Xaa is Lys Pro, Lys Ala, Asp Pro, Asp Lys, Asp
      Ornithine, Asp diaminobutyric acid, Asp diaminopropionic acid, or
      Asp Norleucine.
```

```
<220> FEATURE:
<221> NAME/KEY: MISC_FEATURE
<222> LOCATION: (30)..(30)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(32)
<223> OTHER INFORMATION: Xaa is a two residue extension of the B chain
      containing at least one acidic residue (Glu or Asp).

<400> SEQUENCE: 21

Phe Val Glu Gln His Leu Cys Gly Ser His Leu Val Glu Ala Leu Tyr
1               5                   10                  15

Leu Val Cys Gly Glu Arg Gly Phe Phe Tyr Thr Xaa Xaa Xaa Xaa Xaa
            20                  25                  30

<210> SEQ ID NO 22
<211> LENGTH: 31
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Where Xaa is a non standard amino acid selected
      from the group consisting of 2 CH3 Phe, 3 CH3 Phe, 4 CH3 Phe,
      Cyclohexanylalanine, pentafluoro Phe, 2F Phe, 3F Phe, 2 Cl Phe, 3
      Cl Phe, 4 Cl Phe, 2 Br Phe, 3 Br Phe, and 4 Br Phe.
<220> FEATURE:
<221> NAME/KEY: MISC_FEATURE
<222> LOCATION: (28)..(29)
<223> OTHER INFORMATION: Where Xaa Xaa is Lys Pro, Lys Ala, Asp Pro, Asp
      Lys, Asp Orn, Asp diaminobutyric acid, Asp diaminopropionic acid,
      or Asp Norleucine.
<220> FEATURE:
<221> NAME/KEY: MISC_FEATURE
<222> LOCATION: (30)..(30)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Glu or Asp.

<400> SEQUENCE: 22

Phe Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa Xaa Xaa
            20                  25                  30

<210> SEQ ID NO 23
<211> LENGTH: 32
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is a non standard amino acid selected from
      the group consisting of 2 CH3 Phe, 3 CH3 Phe, 4 CH3 Phe,
      Cyclohexanylalanine, pentafluoro Phe, 2F Phe, 3F Phe, 2 Cl Phe, 3
      Cl Phe, 4 Cl Phe, 2 Br Phe, 3 Br Phe, and 4 Br Phe.
<220> FEATURE:
<221> NAME/KEY: MISC_FEATURE
<222> LOCATION: (28)..(29)
<223> OTHER INFORMATION: Xaa is Lys Pro, Lys Ala, Asp Pro, Asp Lys, Asp
      Ornithine, Asp diaminobutyric acid, Asp diaminopropionic acid, or
      Asp Norleucine.
<220> FEATURE:
<221> NAME/KEY: MISC_FEATURE
```

-continued

```
<222> LOCATION: (30)..(30)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(32)
<223> OTHER INFORMATION: Xaa is a two residue extension of the B chain
      containing at least one acidic residue (Glu or Asp).

<400> SEQUENCE: 23

Phe Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa Xaa Xaa Xaa
            20                  25                  30

<210> SEQ ID NO 24
<211> LENGTH: 32
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is Asp or Glu.
<220> FEATURE:
<221> NAME/KEY: MISC_FEATURE
<222> LOCATION: (28)..(29)
<223> OTHER INFORMATION: Xaa is Lys Pro, Lys Ala, Asp Pro, Asp Lys, Asp
      Ornithine, Asp diaminobutyric acid, Asp diaminopropionic acid.
<220> FEATURE:
<221> NAME/KEY: MISC_FEATURE
<222> LOCATION: (30)..(30)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(32)
<223> OTHER INFORMATION: Xaa is a two residue extension of the B chain
      containing at least one acidic residue (Glu or Asp).

<400> SEQUENCE: 24

Phe Val Glu Gln His Leu Cys Gly Ser Xaa Leu Val Glu Ala Leu Tyr
1               5                   10                  15

Leu Val Cys Gly Glu Arg Gly Phe Phe Tyr Thr Xaa Xaa Xaa Xaa Xaa
            20                  25                  30

<210> SEQ ID NO 25
<211> LENGTH: 32
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is any amino acid.
<220> FEATURE:
<221> NAME/KEY: MISC_FEATURE
<222> LOCATION: (24)..(24)
<223> OTHER INFORMATION: Xaa is a non standard amino acid selected from
      the group consisting of 2 CH3 Phe, 3 CH3 Phe, 4 CH3 Phe,
      Cyclohexanylalanine, pentafluoro Phe, 2F Phe, 3F Phe, 2 Cl Phe, 3
      Cl Phe, 4 Cl Phe, 2 Br Phe, 3 Br Phe, and 4 Br Phe.
<220> FEATURE:
<221> NAME/KEY: MISC_FEATURE
<222> LOCATION: (28)..(29)
<223> OTHER INFORMATION: Xaa is Lys Pro, Lys Ala, Asp Pro, Asp Lys, Asp
      Ornithine, Asp diaminobutyric acid, Asp diaminopropionic acid.
<220> FEATURE:
<221> NAME/KEY: MISC_FEATURE
<222> LOCATION: (30)..(30)
<223> OTHER INFORMATION: Xaa is a non standard amino acid selected from
```

```
      the group consisting of 2 CH3 Phe, 3 CH3 Phe, 4 CH3 Phe,
      Cyclohexanylalanine, pentafluoro Phe, 2F Phe, 3F Phe, 2 Cl Phe, 3
      Cl Phe, 4 Cl Phe, 2 Br Phe, 3 Br Phe, and 4 Br Phe.
<220> FEATURE:
<221> NAME/KEY: MISC_FEATURE
<222> LOCATION: (31)..(32)
<223> OTHER INFORMATION: Xaa is a non standard amino acid selected from
      the group consisting of 2 CH3 Phe, 3 CH3 Phe, 4 CH3 Phe,
      Cyclohexanylalanine, pentafluoro Phe, 2F Phe, 3F Phe, 2 Cl Phe, 3
      Cl Phe, 4 Cl Phe, 2 Br Phe, 3 Br Phe, and 4 Br Phe.

<400> SEQUENCE: 25

Phe Val Glu Gln His Leu Cys Gly Ser Xaa Leu Val Glu Ala Leu Tyr
1               5                   10                  15

Leu Val Cys Gly Glu Arg Gly Xaa Phe Tyr Thr Xaa Xaa Xaa Xaa
            20                  25                  30

<210> SEQ ID NO 26
<211> LENGTH: 30
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.

<400> SEQUENCE: 26

Phe Val Glu Gln His Leu Cys Gly Ser His Leu Val Glu Ala Leu Tyr
1               5                   10                  15

Leu Val Cys Gly Glu Arg Gly Phe Phe Tyr Xaa Pro Xaa Thr
            20                  25                  30

<210> SEQ ID NO 27
<211> LENGTH: 30
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (30)..(30)
<223> OTHER INFORMATION: Xaa is an amidated Thr.

<400> SEQUENCE: 27

Phe Val Glu Gln His Leu Cys Gly Ser His Leu Val Glu Ala Leu Tyr
1               5                   10                  15

Leu Val Cys Gly Glu Arg Gly Phe Phe Tyr Xaa Pro Xaa Xaa
            20                  25                  30

<210> SEQ ID NO 28
<211> LENGTH: 31
<212> TYPE: PRT
```

<213> ORGANISM: Homo sapiens
<220> FEATURE:
<221> NAME/KEY: MISC_FEATURE
<222> LOCATION: (27)..(27)
<223> OTHER INFORMATION: Xaa is an O-Beta Ser linked monosaccharide pyranoside or O-Beta Thr linked monosaccharide pyranoside selected from a group consisting of alpha-D mannopyranoside, alpha-D glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine, diaminobutyric acid or diaminopropionic acid.
<220> FEATURE:
<221> NAME/KEY: MISC_FEATURE
<222> LOCATION: (31)..(31)
<223> OTHER INFORMATION: Xaa is Lys, Arg, or His.

<400> SEQUENCE: 28

Phe Val Glu Gln His Leu Cys Gly Ser His Leu Val Glu Ala Leu Tyr
1               5                   10                  15

Leu Val Cys Gly Glu Arg Gly Phe Phe Tyr Xaa Pro Xaa Thr Xaa
            20                  25                  30

<210> SEQ ID NO 29
<211> LENGTH: 32
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa is an O-Beta Ser linked monosaccharide pyranoside or O-Beta Thr linked monosaccharide pyranoside selected from a group consisting of alpha-D mannopyranoside, alpha-D glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine, diaminobutyric acid or diaminopropionic acid.
<220> FEATURE:
<221> NAME/KEY: MISC_FEATURE
<222> LOCATION: (31)..(31)
<223> OTHER INFORMATION: Xaa is Ornithine, diaminobutyric acid or diaminopropionic acid.
<220> FEATURE:
<221> NAME/KEY: MISC_FEATURE
<222> LOCATION: (32)..(32)
<223> OTHER INFORMATION: Xaa is amidated Lys, amidated Arg, or amidated His.

<400> SEQUENCE: 29

Phe Val Glu Gln His Leu Cys Gly Ser His Leu Val Glu Ala Leu Tyr
1               5                   10                  15

Leu Val Cys Gly Glu Arg Gly Phe Phe Tyr Xaa Pro Xaa Thr Xaa Xaa
            20                  25                  30

<210> SEQ ID NO 30
<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa a non standard amino acid selected from the group consisting of 2 CH3 Phe, 3 CH3 Phe, 4 CH3 Phe, Cyclohexanylalanine, pentafluoro Phe, 2F Phe, 3F Phe, 2 Cl Phe, 3 Cl Phe, 4 Cl Phe, 2 Br Phe, 3 Br Phe, and 4 Br Phe.
<220> FEATURE:
<221> NAME/KEY: MISC_FEATURE
<222> LOCATION: (27)..(27)
<223> OTHER INFORMATION: Xaa is an O-Beta Ser linked monosaccharide pyranoside or O-Beta Thr linked monosaccharide pyranoside selected from a group consisting of alpha-D mannopyranoside, alpha-D
glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.

<400> SEQUENCE: 30

Phe Val Glu Gln His Leu Cys Gly Ser His Leu Val Glu Ala Leu Tyr
1               5                   10                  15

Leu Val Cys Gly Glu Arg Gly Xaa Phe Tyr Xaa Pro Xaa Thr
            20                  25                  30

<210> SEQ ID NO 31
<211> LENGTH: 31
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (30)..(30)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Alanine, Norleucine, Ornithine,
      diaminobutyric acid or diaminopropionic acid.

<400> SEQUENCE: 31

Phe Val Glu Gln His Leu Cys Gly Ser His Leu Val Glu Ala Leu Tyr
1               5                   10                  15

Leu Val Cys Gly Glu Arg Gly Phe Phe Tyr Thr Pro Xaa Xaa Xaa
            20                  25                  30

<210> SEQ ID NO 32
<211> LENGTH: 32
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (30)..(30)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Alanine, Norleucine, Ornithine,
      diaminobutyric acid or diaminopropionic acid and the amino acid is
      amidated.
<220> FEATURE:
<221> NAME/KEY: misc_feature
<222> LOCATION: (32)..(32)
<223> OTHER INFORMATION: Xaa can be any naturally occurring amino acid

<400> SEQUENCE: 32

Phe Val Glu Gln His Leu Cys Gly Ser His Leu Val Glu Ala Leu Tyr
1               5                   10                  15

```
Leu Val Cys Gly Glu Arg Gly Phe Phe Tyr Thr Pro Xaa Xaa Xaa Xaa
            20                  25                  30
```

<210> SEQ ID NO 33
<211> LENGTH: 30
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.

<400> SEQUENCE: 33

```
Phe Val Glu Gln His Leu Cys Gly Ser His Leu Val Gln Ala Leu Tyr
1               5                   10                  15

Leu Val Cys Gly Glu Arg Gly Phe Phe Tyr Xaa Pro Xaa Thr
            20                  25                  30
```

<210> SEQ ID NO 34
<211> LENGTH: 30
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (30)..(30)
<223> OTHER INFORMATION: Xaa is an amidated Thr.

<400> SEQUENCE: 34

```
Phe Val Glu Gln His Leu Cys Gly Ser His Leu Val Gln Ala Leu Tyr
1               5                   10                  15

Leu Val Cys Gly Glu Arg Gly Phe Phe Tyr Xaa Pro Xaa Xaa
            20                  25                  30
```

<210> SEQ ID NO 35
<211> LENGTH: 31
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE

```
<222> LOCATION: (31)..(31)
<223> OTHER INFORMATION: Xaa is Ornithine diaminobutyric acid or
      diaminopropionic acid.

<400> SEQUENCE: 35

Phe Val Glu Gln His Leu Cys Gly Ser His Leu Val Gln Ala Leu Tyr
1               5                   10                  15

Leu Val Cys Gly Glu Arg Gly Phe Phe Tyr Xaa Pro Xaa Thr Xaa
            20                  25                  30

<210> SEQ ID NO 36
<211> LENGTH: 32
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (31)..(32)
<223> OTHER INFORMATION: Xaa is an amidated Ornitine, diaminobutyric
      acid or diaminopropionic acid.

<400> SEQUENCE: 36

Phe Val Glu Gln His Leu Cys Gly Ser His Leu Val Gln Ala Leu Tyr
1               5                   10                  15

Leu Val Cys Gly Glu Arg Gly Phe Phe Tyr Xaa Pro Xaa Thr Xaa Xaa
            20                  25                  30

<210> SEQ ID NO 37
<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is a non standard amino acid selected from
      the group consisting of 2 CH3 Phe, 3 CH3 Phe, 4 CH3 Phe,
      Cyclohexanylalanine, pentafluoro Phe, 2F Phe, 3F Phe, 2 Cl Phe, 3
      Cl Phe, 4 Cl Phe, 2 Br Phe, 3 Br Phe, and 4 Br Phe.
<220> FEATURE:
<221> NAME/KEY: MISC_FEATURE
<222> LOCATION: (27)..(27)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.

<400> SEQUENCE: 37

Phe Val Glu Gln His Leu Cys Gly Ser His Leu Val Gln Ala Leu Tyr
1               5                   10                  15

Leu Val Cys Gly Glu Arg Gly Xaa Phe Tyr Xaa Pro Xaa Thr
            20                  25                  30

<210> SEQ ID NO 38
<211> LENGTH: 31
```

<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (30)..(30)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Alanine, Norleucine, Ornithine,
      diaminobutyric acid or diaminopropionic acid.

<400> SEQUENCE: 38

Phe Val Glu Gln His Leu Cys Gly Ser His Leu Val Gln Ala Leu Tyr
1               5                   10                  15

Leu Val Cys Gly Glu Arg Gly Phe Phe Tyr Thr Pro Xaa Xaa Xaa
            20                  25                  30

<210> SEQ ID NO 39
<211> LENGTH: 32
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (30)..(30)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is an amidated amino acid selected from
      Ala, Norleucine, Ornithing, diaminobutyric acid and
      diaminopropionic acid.
<220> FEATURE:
<221> NAME/KEY: MISC_FEATURE
<222> LOCATION: (32)..(32)
<223> OTHER INFORMATION: Xaa is an amine.

<400> SEQUENCE: 39

Phe Val Glu Gln His Leu Cys Gly Ser His Leu Val Gln Ala Leu Tyr
1               5                   10                  15

Leu Val Cys Gly Glu Arg Gly Phe Phe Tyr Thr Pro Xaa Xaa Xaa Xaa
            20                  25                  30

<210> SEQ ID NO 40
<211> LENGTH: 31
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is a non standard amino acid selected from
      the group consisting of 2 CH3 Phe, 3 CH3 Phe, 4 CH3 Phe,
      Cyclohexanylalanine, pentafluoro Phe, 2F Phe, 3F Phe, 2 Cl Phe, 3
      Cl Phe, 4 Cl Phe, 2 Br Phe, 3 Br Phe, and 4 Br Phe.
<220> FEATURE:
<221> NAME/KEY: MISC_FEATURE
<222> LOCATION: (29)..(29)

```
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (30)..(30)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Alanine, Norleucine, Ornithine,
      diaminobutyric acid or diaminopropionic acid.

<400> SEQUENCE: 40

Phe Val Glu Gln His Leu Cys Gly Ser His Leu Val Gln Ala Leu Tyr
1               5                   10                  15

Leu Val Cys Gly Glu Arg Gly Xaa Phe Tyr Thr Pro Xaa Xaa Xaa
            20                  25                  30

<210> SEQ ID NO 41
<211> LENGTH: 32
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is Phe or optionally a non standard amino
      acid selected from the group consisting of 2 CH3 Phe, 3 CH3 Phe,
      4 CH3 Phe, Cyclohexanylalanine, pentafluoro Phe, 2F Phe, 3F Phe,
      2 Cl Phe, 3 Cl Phe, 4 Cl Phe, 2 Br Phe, 3 Br Phe, and 4 Br Phe.
<220> FEATURE:
<221> NAME/KEY: MISC_FEATURE
<222> LOCATION: (26)..(26)
<223> OTHER INFORMATION: Xaa is 3 mono iodo Tyr or (3,5) di iodo Tyr.
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (30)..(30)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (32)..(32)
<223> OTHER INFORMATION: Xaa is an unmodified C terminal carboxylate
      group or C terminal amide.

<400> SEQUENCE: 41

Phe Val Glu Gln His Leu Cys Gly Ser His Leu Val Gln Ala Leu Tyr
1               5                   10                  15

Leu Val Cys Gly Glu Arg Gly Xaa Phe Xaa Thr Pro Xaa Xaa Xaa Xaa
            20                  25                  30

<210> SEQ ID NO 42
<211> LENGTH: 32
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa a non standard amino acid selected from
```

```
        the group consisting of 2 CH3 Phe, 3 CH3 Phe, 4 CH3 Phe,
        Cyclohexanylalanine, pentafluoro Phe, 2F Phe, 3F Phe, 2 Cl Phe,
        3 Cl Phe, 4 Cl Phe, 2 Br Phe, 3 Br Phe, and 4 Br Phe.
<220> FEATURE:
<221> NAME/KEY: MISC_FEATURE
<222> LOCATION: (29)..(29)
<223> OTHER INFORMATION: Xaa is Alanine, Norleucine, Ornithine,
        diaminobutyric acid or diaminopropionic acid.
<220> FEATURE:
<221> NAME/KEY: MISC_FEATURE
<222> LOCATION: (30)..(30)
<223> OTHER INFORMATION: Xaa is an O-Beta Ser linked monosaccharide
        pyranoside or O-Beta Thr linked monosaccharide pyranoside selected
        from a group consisting of alpha-D mannopyranoside, alpha-D
        glucopyranoside, or N acetyl Beta-D galactopyranoside..
<220> FEATURE:
<221> NAME/KEY: MISC_FEATURE
<222> LOCATION: (31)..(31)
<223> OTHER INFORMATION: Xaa is Alanine, Norleucine, Ornithine,
        diaminobutyric acid or diaminopropionic acid.
<220> FEATURE:
<221> NAME/KEY: MISC_FEATURE
<222> LOCATION: (32)..(32)
<223> OTHER INFORMATION: Xaa is an amine.

<400> SEQUENCE: 42

Phe Val Glu Gln His Leu Cys Gly Ser His Leu Val Gln Ala Leu Tyr
1               5                   10                  15

Leu Val Cys Gly Glu Arg Gly Xaa Phe Tyr Thr Pro Xaa Xaa Xaa Xaa
            20                  25                  30

<210> SEQ ID NO 43
<211> LENGTH: 32
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Xaa is Gln or Glu.
<220> FEATURE:
<221> NAME/KEY: MISC_FEATURE
<222> LOCATION: (24)..(24)
<223> OTHER INFORMATION: Xaa is a non standard amino acid selected
        from the group consisting of Phe, 2 CH3 Phe, 3 CH3 Phe, 4 CH3 Phe,
        Cyclohexanylalanine, pentafluoro Phe, 2F Phe, 3F Phe, 2 Cl Phe, 3
        Cl Phe, 4 Cl Phe, 2 Br Phe, 3 Br Phe, and 4 Br Phe.
<220> FEATURE:
<221> NAME/KEY: MISC_FEATURE
<222> LOCATION: (27)..(27)
<223> OTHER INFORMATION: Xaa is an O-Beta Ser linked monosaccharide
        pyranoside or O-Beta Thr linked monosaccharide pyranoside selected
        from a group consisting of alpha-D mannopyranoside, alpha-D
        glucopyranoside, or N acetyl Beta-D galactopyranoside.
<220> FEATURE:
<221> NAME/KEY: MISC_FEATURE
<222> LOCATION: (28)..(29)
<223> OTHER INFORMATION: Xaa are Lys Pro, Lys Ala, Asp Pro, Asp Lys, Asp
        Ala, Asp Norleucine, Asp Ornithine, Asp diaminobutyric acid, or
        Asp dipropionic acid.
<220> FEATURE:
<221> NAME/KEY: MISC_FEATURE
<222> LOCATION: (30)..(30)
<223> OTHER INFORMATION: Xaa is an O-Beta Ser linked monosaccharide
        pyranoside or O-Beta Thr linked monosaccharide pyranoside selected
        from a group consisting of alpha-D mannopyranoside, alpha-D
        glucopyranoside, or N acetyl Beta-D galactopyranoside.
<220> FEATURE:
<221> NAME/KEY: MISC_FEATURE
<222> LOCATION: (31)..(32)
<223> OTHER INFORMATION: Xaa are selected from a group consisting of
        Ala, Asp, and Glu such that at least one acidic residue is
        selected.

<400> SEQUENCE: 43

Phe Val Glu Gln His Leu Cys Gly Ser His Leu Val Xaa Ala Leu Tyr
```

-continued

```
1               5                   10                  15

Leu Val Cys Gly Glu Arg Gly Xaa Phe Tyr Xaa Xaa Xaa Xaa Xaa Xaa
            20                  25                  30
```

<210> SEQ ID NO 44
<211> LENGTH: 31
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Xaa is Gln or Glu.
<220> FEATURE:
<221> NAME/KEY: MISC_FEATURE
<222> LOCATION: (24)..(24)
<223> OTHER INFORMATION: Xaa is a non standard amino acid selected from
      the group consisting of Phe, 2 CH3 Phe, 3 CH3 Phe, 4 CH3 Phe,
      Cyclohexanylalanine, pentafluoro Phe, 2F Phe, 3F Phe, 2 Cl Phe, 3
      Cl Phe, 4 Cl Phe, 2 Br Phe, 3 Br Phe, and 4 Br Phe.
<220> FEATURE:
<221> NAME/KEY: MISC_FEATURE
<222> LOCATION: (27)..(27)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (28)..(29)
<223> OTHER INFORMATION: Xaa are Lys Pro, Lys Ala, Asp Pro, Asp Lys,
      Asp Ala, Asp Norleucine, Asp Ornithine, Asp diaminobutyric acid,
      or Asp dipropionic acid.
<220> FEATURE:
<221> NAME/KEY: MISC_FEATURE
<222> LOCATION: (30)..(30)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Ala, Asp, or Glu.

<400> SEQUENCE: 44

```
Phe Val Glu Gln His Leu Cys Gly Ser His Leu Val Xaa Ala Leu Tyr
1               5                   10                  15

Leu Val Cys Gly Glu Arg Gly Xaa Phe Tyr Xaa Xaa Xaa Xaa Xaa
            20                  25                  30
```

<210> SEQ ID NO 45
<211> LENGTH: 31
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is Asp or Glu.
<220> FEATURE:
<221> NAME/KEY: MISC_FEATURE
<222> LOCATION: (13)..(13)
<223> OTHER INFORMATION: Xaa is Ala, Asp, or Glu.
<220> FEATURE:
<221> NAME/KEY: MISC_FEATURE
<222> LOCATION: (24)..(24)
<223> OTHER INFORMATION: Xaa is a non standard amino acid selected from
      the group consisting of Phe, 2 CH3 Phe, 3 CH3 Phe, 4 CH3 Phe,
      Cyclohexanylalanine, pentafluoro Phe, 2F Phe, 3F Phe, 2 Cl Phe, 3
      Cl Phe, 4 Cl Phe, 2 Br Phe, 3 Br Phe, and 4 Br Phe; and where
<220> FEATURE:
<221> NAME/KEY: MISC_FEATURE
<222> LOCATION: (27)..(27)
<223> OTHER INFORMATION: Xaa is an O-Beta Ser linked monosaccaride
      pyranoside or O-Beta Thr linked monosaccaride pyranoside selected -continued from a group consisting of alpha-D mannopyranoside, alpha-D
    glucopyranoside, or N acetyl Beta-D galactopyranoside.
<220> FEATURE:
<221> NAME/KEY: MISC_FEATURE
<222> LOCATION: (28)..(29)
<223> OTHER INFORMATION: Xaa are Lys Pro, Lys Ala, Asp Pro, Asp Lys,
    Asp Ala, Asp Norleucine, Asp Ornithine, Asp diaminobutyric acid,
    or Asp dipropionic acid.
<220> FEATURE:
<221> NAME/KEY: MISC_FEATURE
<222> LOCATION: (30)..(30)
<223> OTHER INFORMATION: Xaa is an O-Beta Ser linked monosaccharide
    pyranoside or O-Beta Thr linked monosaccharide pyranoside selected
    from a group consisting of alpha-D mannopyranoside, alpha-D
    glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Ala, Asp, or Glu.

<400> SEQUENCE: 45

Phe Val Glu Gln His Leu Cys Gly Ser Xaa Leu Val Xaa Ala Leu Tyr
1               5                   10                  15

Leu Val Cys Gly Glu Arg Gly Xaa Phe Tyr Xaa Xaa Xaa Xaa Xaa
            20                  25                  30

<210> SEQ ID NO 46
<211> LENGTH: 31
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Xaa is Glu or Gln.
<220> FEATURE:
<221> NAME/KEY: MISC_FEATURE
<222> LOCATION: (24)..(24)
<223> OTHER INFORMATION: Xaa is Glu or Gln.
<220> FEATURE:
<221> NAME/KEY: MISC_FEATURE
<222> LOCATION: (27)..(27)
<223> OTHER INFORMATION: Xaa is an O-Beta Ser linked monosaccharide
    pyranoside or O-Beta Thr linked monosaccharide pyranoside selected
    from a group consisting of alpha-D mannopyranoside, alpha-D
    glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine,
    diaminobutyric acid or diaminopropionic acid.
<220> FEATURE:
<221> NAME/KEY: MISC_FEATURE
<222> LOCATION: (30)..(30)
<223> OTHER INFORMATION: Xaa is an O-Beta Ser linked monosaccharide
    pyranoside or O-Beta Thr linked monosaccharide pyranoside selected
    from a group consisting of alpha-D mannopyranoside, alpha-D
    glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Alanine, Norleucine, Ornithine,
    diaminobutyric acid or diaminopropionic acid.

<400> SEQUENCE: 46

Phe Val Glu Gln His Leu Cys Gly Ser His Leu Val Xaa Ala Leu Tyr
1               5                   10                  15

Leu Val Cys Gly Glu Arg Gly Xaa Phe Tyr Xaa Pro Xaa Xaa Xaa
            20                  25                  30

<210> SEQ ID NO 47
<211> LENGTH: 32
<212> TYPE: PRT
<213> ORGANISM: Homo sapiens

```
<220> FEATURE:
<221> NAME/KEY: MISC_FEATURE
<222> LOCATION: (13)..(13)
<223> OTHER INFORMATION: Xaa is Glu or Gln.
<220> FEATURE:
<221> NAME/KEY: MISC_FEATURE
<222> LOCATION: (24)..(24)
<223> OTHER INFORMATION: Xaa is Glu or Gln.
<220> FEATURE:
<221> NAME/KEY: MISC_FEATURE
<222> LOCATION: (27)..(27)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (29)..(29)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (30)..(30)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (31)..(31)
<223> OTHER INFORMATION: Xaa is Alanine, Norleucine, Ornithine,
      diaminobutyric acid or diaminopropionic acid.
<220> FEATURE:
<221> NAME/KEY: MISC_FEATURE
<222> LOCATION: (32)..(32)
<223> OTHER INFORMATION: Xaa is an amine.

<400> SEQUENCE: 47

Phe Val Glu Gln His Leu Cys Gly Ser His Leu Val Xaa Ala Leu Tyr
1               5                   10                  15

Leu Val Cys Gly Glu Arg Gly Xaa Phe Tyr Xaa Pro Xaa Xaa Xaa Xaa
            20                  25                  30

<210> SEQ ID NO 48
<211> LENGTH: 21
<212> TYPE: PRT
<213> ORGANISM: Homo sapiens

<400> SEQUENCE: 48

Gly Ile Val Glu Gln Cys Cys Glu Ser Ile Cys Ser Leu Tyr Gln Leu
1               5                   10                  15

Glu Asn Tyr Cys Asn
            20

<210> SEQ ID NO 49
<211> LENGTH: 21
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is selected from a group consisting of
      His, Trp, Lys, Arg, or Gln.

<400> SEQUENCE: 49

Gly Ile Val Glu Gln Cys Cys Xaa Ser Ile Cys Ser Leu Tyr Gln Leu
1               5                   10                  15

Glu Asn Tyr Cys Asn
            20
```

```
<210> SEQ ID NO 50
<211> LENGTH: 21
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is selected from a group consisting of His,
      Trp, Lys, Arg, or Gln.
<220> FEATURE:
<221> NAME/KEY: MISC_FEATURE
<222> LOCATION: (21)..(21)
<223> OTHER INFORMATION: Xaa is Asp, Gly or Ala.

<400> SEQUENCE: 50

Gly Ile Val Glu Gln Cys Cys Xaa Ser Ile Cys Ser Leu Tyr Gln Leu
1               5                   10                  15

Glu Asn Tyr Cys Xaa
            20

<210> SEQ ID NO 51
<211> LENGTH: 21
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: Xaa is Gly or Ala.

<400> SEQUENCE: 51

Gly Ile Val His Gln Cys Cys His Ser Ile Cys Ser Leu Tyr Gln Leu
1               5                   10                  15

Glu Asn Tyr Cys Xaa
            20

<210> SEQ ID NO 52
<211> LENGTH: 22
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is selected from a group consisting of Thr,
      His, Trp, Lys, Arg, or Gln.
<220> FEATURE:
<221> NAME/KEY: MISC_FEATURE
<222> LOCATION: (9)..(9)
<223> OTHER INFORMATION: Xaa is Arg, Lys, Ornithine, diaminobutyric acid
      or diaminopropionic acid.

<400> SEQUENCE: 52

Xaa Gly Ile Val Glu Gln Cys Cys Xaa Ser Ile Cys Ser Leu Tyr Gln
1               5                   10                  15

Leu Glu Asn Tyr Cys Asn
            20

<210> SEQ ID NO 53
<211> LENGTH: 22
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is selected from a group consisting of Thr,
      His, Trp, Lys, Arg, or Gln.
<220> FEATURE:
<221> NAME/KEY: MISC_FEATURE
<222> LOCATION: (9)..(9)
<223> OTHER INFORMATION: Xaa is Arg, Lys, Ornithine, diaminobutyric acid
      or diaminopropionic acid.
```

```
<220> FEATURE:
<221> NAME/KEY: MISC_FEATURE
<222> LOCATION: (22)..(22)
<223> OTHER INFORMATION: Xaa is Ala or Gly.

<400> SEQUENCE: 53

Xaa Gly Ile Val Glu Gln Cys Cys Xaa Ser Ile Cys Ser Leu Tyr Gln
1               5                   10                  15

Leu Glu Asn Tyr Cys Xaa
            20

<210> SEQ ID NO 54
<211> LENGTH: 8
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Norleucine, Ornithine, diaminobutytic
      acid, or diaminopropionic acid.

<400> SEQUENCE: 54

Gly Phe Phe Tyr Xaa Pro Xaa Thr
1               5

<210> SEQ ID NO 55
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Cyclohexanylalanine, 2 CH3 Phe, 3 CH3
      Phe, 4 CH3 Phe, pentafluoro Phe, 2F Phe, 3F Phe, 2 Cl Phe, 3 Cl
      Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Norleucine, Ornithine, diaminobutytic
      acid, or diaminopropionic acid.

<400> SEQUENCE: 55

Gly Xaa Phe Tyr Xaa Pro Xaa Thr
1               5

<210> SEQ ID NO 56
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
```

<222> LOCATION: (7)..(7)
<223> OTHER INFORMATION: Xaa is Norleucine, Ornithine, diaminobutytic
      acid, or diaminopropionic acid.
<220> FEATURE:
<221> NAME/KEY: MISC_FEATURE
<222> LOCATION: (9)..(9)
<223> OTHER INFORMATION: Xaa is an amidated Thr.

<400> SEQUENCE: 56

Gly Phe Phe Tyr Xaa Pro Xaa Thr Xaa
1               5

<210> SEQ ID NO 57
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is 3 mono iodo Tyr or di iodo (3, 5) Tyr.
<220> FEATURE:
<221> NAME/KEY: MISC_FEATURE
<222> LOCATION: (5)..(5)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Norleucine, Ornithine, diaminobutytic
      acid, or diaminopropionic acid.

<400> SEQUENCE: 57

Gly Phe Phe Xaa Xaa Pro Xaa Thr
1               5

<210> SEQ ID NO 58
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Norleucine, Ornithine, diaminobutytic
      acid, or diaminopropionic acid.
<220> FEATURE:
<221> NAME/KEY: MISC_FEATURE
<222> LOCATION: (9)..(9)
<223> OTHER INFORMATION: Xaa is Ornithine, diaminobutytic acid, or
      diaminopropionic acid.

<400> SEQUENCE: 58

Gly Phe Phe Tyr Xaa Pro Xaa Thr Xaa
1               5

<210> SEQ ID NO 59
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Cyclohexanylalanine, 2 CH3 Phe, 3 CH3
      Phe, 4 CH3 Phe, pentafluoro Phe, 2F Phe, 3F Phe, 2 Cl Phe, 3 Cl
      Phe, 4 Cl Phe, 2 Br Phe, 3 Br Phe, or 4 Br Phe.

-continued

```
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Norleucine, Ornithine, diaminobutytic
      acid, or diaminopropionic acid.
<220> FEATURE:
<221> NAME/KEY: MISC_FEATURE
<222> LOCATION: (9)..(9)
<223> OTHER INFORMATION: Xaa is Ornithine, diaminobutytic acid, or
      diaminopropionic acid.

<400> SEQUENCE: 59

Gly Xaa Phe Tyr Xaa Pro Xaa Thr Xaa
1               5

<210> SEQ ID NO 60
<211> LENGTH: 10
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Norleucine, Ornithine, diaminobutytic
      acid, or diaminopropionic acid.
<220> FEATURE:
<221> NAME/KEY: MISC_FEATURE
<222> LOCATION: (9)..(9)
<223> OTHER INFORMATION: Xaa is Norleucine, Ornithine, diaminobutytic
      acid, or diaminopropionic acid.
<220> FEATURE:
<221> NAME/KEY: MISC_FEATURE
<222> LOCATION: (10)..(10)
<223> OTHER INFORMATION: Xaa is an amine.

<400> SEQUENCE: 60

Gly Phe Phe Tyr Xaa Pro Xaa Thr Xaa Xaa
1               5                   10

<210> SEQ ID NO 61
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is 3 mono iodo Tyr or di iodo (3, 5) Tyr.
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Norleucine, Ornithine, diaminobutytic
      acid, or diaminopropionic acid.
<220> FEATURE:
<221> NAME/KEY: MISC_FEATURE
<222> LOCATION: (9)..(9)
```

```
<223> OTHER INFORMATION: Xaa is Ornithine, diaminobutytic acid, or
      diaminopropionic acid.

<400> SEQUENCE: 61

Gly Phe Phe Xaa Xaa Pro Xaa Thr Xaa
1               5

<210> SEQ ID NO 62
<211> LENGTH: 8
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.

<400> SEQUENCE: 62

Gly Phe Phe Tyr Xaa Lys Pro Thr
1               5

<210> SEQ ID NO 63
<211> LENGTH: 10
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.

<400> SEQUENCE: 63

Gly Phe Phe Tyr Xaa Lys Pro Thr Glu Glu
1               5                   10

<210> SEQ ID NO 64
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Cyclohexanylalanine, 2 CH3 Phe, 3 CH3
      Phe, 4 CH3 Phe, pentafluoro Phe, 2F Phe, 3F Phe, 2 Cl Phe, 3 Cl
      Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.

<400> SEQUENCE: 64

Gly Xaa Phe Tyr Xaa Lys Pro Thr
1               5

<210> SEQ ID NO 65
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Cyclohexanylalanine, 2 CH3 Phe, 3 CH3
      Phe, 4 CH3 Phe, pentafluoro Phe, 2F Phe, 3F Phe, 2 Cl Phe, 3 Cl
      Phe, 4 Cl Phe, 2 Br Phe, 3 Br Phe, or 4 Br Phe.
```

```
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.

<400> SEQUENCE: 65

Gly Xaa Phe Tyr Xaa Lys Pro Thr Glu Glu
1               5                   10

<210> SEQ ID NO 66
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe, Cyclohexanylalanine, 2 CH3 Phe,
      3 CH3 Phe, 4 CH3 Phe, pentafluoro Phe, 2F Phe, 3F Phe, 2 Cl Phe,
      3 Cl Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Pro, Ala, Norleucine, Ornithine,
      diamonibutyric acid, or diaminipropionic acid.

<400> SEQUENCE: 66

Gly Xaa Phe Tyr Xaa Asp Xaa Thr
1               5

<210> SEQ ID NO 67
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe, Cyclohexanylalanine, 2 CH3 Phe,
      3 CH3 Phe, 4 CH3 Phe, pentafluoro Phe, 2F Phe, 3F Phe, 2 Cl Phe,
      3 Cl Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Pro, Ala, Norleucine, Ornithine,
      diamonibutyric acid, or diaminipropionic acid.

<400> SEQUENCE: 67

Gly Xaa Phe Tyr Xaa Asp Xaa Thr Glu Glu
1               5                   10

<210> SEQ ID NO 68
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
```

```
<223> OTHER INFORMATION: Xaa is Phe, Cyclohexanylalanine, 2 CH3 Phe,
      3 CH3 Phe, 4 CH3 Phe, pentafluoro Phe, 2F Phe, 3F Phe, 2 Cl Phe,
      3 Cl Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (9)..(10)
<223> OTHER INFORMATION: At least one amino acid has an acidic side
      chain.
<220> FEATURE:
<221> NAME/KEY: MISC_FEATURE
<222> LOCATION: (9)..(9)
<223> OTHER INFORMATION: Xaa is Pro, Ala, Norleucine, Ornithine,
      diaminobutyric acid or diaminopropionic acid.
<220> FEATURE:
<221> NAME/KEY: MISC_FEATURE
<222> LOCATION: (10)..(10)
<223> OTHER INFORMATION: Xaa is Phe, Cyclohexanylalanine, 2 CH3 Phe,
      3 CH3 Phe, 4 CH3 Phe, pentafluoro Phe, 2F Phe, 3F Phe, 2 Cl Phe,
      3 Cl Phe, 4 Cl Phe, 2 Br Phe, 3 Br Phe, or 4 Br Phe.

<400> SEQUENCE: 68

Gly Xaa Phe Tyr Xaa Lys Pro Thr Xaa Xaa
1               5                   10

<210> SEQ ID NO 69
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe, Cyclohexanylalanine, 2 CH3 Phe, 3
      CH3 Phe, 4 CH3 Phe, pentafluoro Phe, 2F Phe, 3F Phe, 2 Cl Phe, 3
      Cl Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Pro, Ala, Norleucine, Ornithine,
      diamonibutyric acid, or diaminipropionic acid.
<220> FEATURE:
<221> NAME/KEY: MISC_FEATURE
<222> LOCATION: (9)..(10)
<223> OTHER INFORMATION: Xaa are each selected from a group consisting
      of Ala, Asp, and Glu such that at least one bears an acidic side
      chain.

<400> SEQUENCE: 69

Gly Xaa Phe Tyr Xaa Asp Xaa Thr Xaa Xaa
1               5                   10

<210> SEQ ID NO 70
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe, Cyclohexanylalanine, 2 CH3 Phe, 3
      CH3 Phe, 4 CH3 Phe, pentafluoro Phe, 2F Phe, 3F Phe, 2 Cl Phe, 3
      Cl Phe, 4 Cl Phe, 2 Br Phe, 3 Br Phe, or 4 Br Phe.
<220> FEATURE:
```

```
<221> NAME/KEY: MISC_FEATURE
<222> LOCATION: (8)..(8)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (9)..(9)
<223> OTHER INFORMATION: Xaa is Pro, Ala, Norleucine, Ornithine,
      diaminobutyric acid or diaminopropionic acid.
<220> FEATURE:
<221> NAME/KEY: MISC_FEATURE
<222> LOCATION: (10)..(10)
<223> OTHER INFORMATION: Xaa is Pro, Ala, Norleucine, Ornithine,
      diaminobutyric acid or diaminopropionic acid.

<400> SEQUENCE: 70

Gly Xaa Phe Tyr Thr Lys Pro Xaa Xaa Xaa
1               5                   10

<210> SEQ ID NO 71
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe, Cyclohexanylalanine, 2 CH3 Phe,
      3 CH3 Phe, 4 CH3 Phe, pentafluoro Phe, 2F Phe, 3F Phe, 2 Cl Phe,
      3 Cl Phe, 4 Cl Phe, 2 Br Phe, 3 Br Phe, or 4 Br Phe.
<220> FEATURE:
<221> NAME/KEY: MISC_FEATURE
<222> LOCATION: (7)..(7)
<223> OTHER INFORMATION: Xaa is Pro, Ala, Norleucine, Ornithine,
      diamonibutyric acid, or diaminipropionic acid.
<220> FEATURE:
<221> NAME/KEY: MISC_FEATURE
<222> LOCATION: (8)..(8)
<223> OTHER INFORMATION: Where Xaa1 is an O? SerB30 linked monosaccharide
      pyranoside or O? ThrB30 linked monosaccharide pyranoside selected
      from a group consisting of ? D mannopyranoside, ? D
      glucopyranoside, or N acetyl ? D galactopyranoside.
<220> FEATURE:
<221> NAME/KEY: MISC_FEATURE
<222> LOCATION: (9)..(10)
<223> OTHER INFORMATION: Xaa are each selected from a group consisting
      of Ala, Asp, and Glu such that at least one bears an acidic side
      chain.

<400> SEQUENCE: 71

Gly Xaa Phe Tyr Thr Asp Xaa Xaa Xaa Xaa
1               5                   10

<210> SEQ ID NO 72
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe, Cyclohexanylalanine, 2 CH3 Phe, 3
      CH3 Phe, 4 CH3 Phe, pentafluoro Phe, 2F Phe, 3F Phe, 2 Cl Phe, 3
      Cl Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccharide
      pyranoside or O-Beta Thr linked monosaccharide pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (8)..(8)
<223> OTHER INFORMATION: Xaa is an O-Beta Ser linked monosaccharide
```

```
        pyranoside or O-Beta Thr linked monosaccaride pyranoside selected
        from a group consisting of alpha-D mannopyranoside, alpha-D
        glucopyranoside, or N acetyl Beta-D galactopyranoside.
<220> FEATURE:
<221> NAME/KEY: MISC_FEATURE
<222> LOCATION: (9)..(10)
<223> OTHER INFORMATION: Xaa are each selected from a group consisting
        of Ala, Asp, and Glu such that at least one bears an acidic side
        chain.

<400> SEQUENCE: 72

Gly Xaa Phe Tyr Xaa Lys Pro Xaa Xaa Xaa
1               5                  10

<210> SEQ ID NO 73
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe, Cyclohexanylalanine, 2 CH3 Phe, 3
        CH3 Phe, 4 CH3 Phe, pentafluoro Phe, 2F Phe, 3F Phe, 2 Cl Phe, 3
        Cl Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccaride
        pyranoside or O-Beta Thr linked monosaccaride pyranoside selected
        from a group consisting of alpha-D mannopyranoside, alpha-D
        glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Pro, Norleucine, Orn, diaminobutyric
        acid, or dipropionic acid.
<220> FEATURE:
<221> NAME/KEY: MISC_FEATURE
<222> LOCATION: (8)..(8)
<223> OTHER INFORMATION: Xaa is an O-Beta Ser linked monosaccaride
        pyranoside or O-Beta Thr linked monosaccaride pyranoside selected
        from a group consisting of alpha-D mannopyranoside, alpha-D
        glucopyranoside, or N acetyl Beta-D galactopyranoside.
<220> FEATURE:
<221> NAME/KEY: MISC_FEATURE
<222> LOCATION: (9)..(9)
<223> OTHER INFORMATION: Xaa is Ala, Asp, and Glu.

<400> SEQUENCE: 73

Gly Xaa Phe Tyr Xaa Asp Xaa Xaa Xaa
1               5

<210> SEQ ID NO 74
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe, Cyclohexanylalanine, 2 CH3 Phe,
        3 CH3 Phe, 4 CH3 Phe, pentafluoro Phe, 2F Phe, 3F Phe, 2 Cl Phe,
        3 Cl Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccaride
        pyranoside or O-Beta Thr linked monosaccaride pyranoside selected
        from a group consisting of alpha-D mannopyranoside, alpha-D
        glucopyranoside, or N acetyl Beta-D galactopyranoside.
<220> FEATURE:
<221> NAME/KEY: MISC_FEATURE
<222> LOCATION: (9)..(10)
<223> OTHER INFORMATION: Xaa are each selected from a group consisting
        of Ala, Asp, and Glu such that at least one bears an acidic side
        chain.
```

<400> SEQUENCE: 74

Gly Xaa Phe Tyr Xaa Lys Asp Pro Xaa Xaa
1               5                   10

<210> SEQ ID NO 75
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe, Cyclohexanylalanine, 2 CH3 Phe, 3
      CH3 Phe, 4 CH3 Phe, pentafluoro Phe, 2F Phe, 3F Phe, 2 Cl Phe, 3
      Cl Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (8)..(8)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (9)..(9)
<223> OTHER INFORMATION: Xaa is Ala, Asp, and Glu.

<400> SEQUENCE: 75

Gly Xaa Phe Tyr Xaa Lys Pro Xaa Xaa
1               5

<210> SEQ ID NO 76
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe, Cyclohexanylalanine, 2 CH3 Phe, 3
      CH3 Phe, 4 CH3 Phe, pentafluoro Phe, 2F Phe, 3F Phe, 2 Cl Phe, 3
      Cl Phe, 4 Cl Phe, 2 Br Phe, 3 Br Phe, or 4 Br Phe.
<220> FEATURE:
<221> NAME/KEY: MISC_FEATURE
<222> LOCATION: (7)..(7)
<223> OTHER INFORMATION: Xaa is Pro, Ala, Norleucine, Ornithine,
      diamonibutyric acid, or diaminipropionic acid.
<220> FEATURE:
<221> NAME/KEY: MISC_FEATURE
<222> LOCATION: (8)..(8)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (9)..(10)
<223> OTHER INFORMATION: Xaa are each selected from a group consisting
      of Ala, Asp, and Glu such that at least one bears an acidic side
      chain.

<400> SEQUENCE: 76

Gly Xaa Phe Tyr Thr Asp Xaa Xaa Xaa Xaa
1               5                   10

<210> SEQ ID NO 77
<211> LENGTH: 9

```
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Norleucine, Ornithine, diaminobutytic
      acid, or diaminopropionic acid.
<220> FEATURE:
<221> NAME/KEY: MISC_FEATURE
<222> LOCATION: (8)..(8)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (9)..(9)
<223> OTHER INFORMATION: Xaa is Norleucine, Ornithine, diaminobutytic
      acid, or diaminopropionic acid; and where Xaa is Ornithine,
      diaminobutytic acid, or diaminopropionic acid.

<400> SEQUENCE: 77

Gly Phe Phe Tyr Xaa Pro Xaa Xaa Xaa
1               5

<210> SEQ ID NO 78
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Cyclohexanylalanine, 2 CH3 Phe, 3 CH3
      Phe, 4 CH3 Phe, pentafluoro Phe, 2F Phe, 3F Phe, 2 Cl Phe, 3 Cl
      Phe, 4 Cl Phe, 2 Br Phe, 3 Br Phe, or 4 Br Phe.
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Norleucine, Ornithine, diaminobutytic
      acid, or diaminopropionic acid.
<220> FEATURE:
<221> NAME/KEY: MISC_FEATURE
<222> LOCATION: (8)..(8)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (9)..(9)
<223> OTHER INFORMATION: Xaa is Ornithine, diaminobutytic acid, or
      diaminopropionic acid.

<400> SEQUENCE: 78

Gly Xaa Phe Tyr Xaa Pro Xaa Xaa Xaa
1               5

<210> SEQ ID NO 79
<211> LENGTH: 9
<212> TYPE: PRT
<213> ORGANISM: Homo sapiens
```

```
<220> FEATURE:
<221> NAME/KEY: MISC_FEATURE
<222> LOCATION: (4)..(4)
<223> OTHER INFORMATION: Xaa is 3 mono iodo Tyr or (3,5) di iodo Tyr.
<220> FEATURE:
<221> NAME/KEY: MISC_FEATURE
<222> LOCATION: (5)..(5)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (7)..(7)
<223> OTHER INFORMATION: Xaa is Norleucine, Ornithine, diaminobutytic
      acid, or diaminopropionic acid.
<220> FEATURE:
<221> NAME/KEY: MISC_FEATURE
<222> LOCATION: (8)..(8)
<223> OTHER INFORMATION: Xaa is an O-Beta Ser linked monosaccaride
      pyranoside or O-Beta Thr linked monosaccaride pyranoside selected
      from a group consisting of alpha-D mannopyranoside, alpha-D
      glucopyranoside, or N acetyl Beta-D galactopyranoside.
<220> FEATURE:
<221> NAME/KEY: MISC_FEATURE
<222> LOCATION: (9)..(9)
<223> OTHER INFORMATION: Xaa is Ornithine, diaminobutytic acid, or
      diaminopropionic acid.

<400> SEQUENCE: 79

Gly Phe Phe Xaa Xaa Pro Xaa Xaa Xaa
1               5
```

US 9,624,287 B2

O-LINKED CARBOHYDRATE-MODIFIED INSULIN ANALOGUES

CROSS REFERENCE TO RELATED APPLICATIONS

This application claims benefit of pending U.S. Provisional Application Nos. 61/672,711 filed Jul. 17, 2012, and 61/693,997 filed on Aug. 28, 2012, the disclosures of which are incorporated by reference herein.

STATEMENT REGARDING FEDERALLY SPONSORED RESEARCH OR DEVELOPMENT

This invention was made with government support under grant numbers DK040949 and DK074176 awarded by the National Institutes of Health. The government has certain rights in the invention.

BACKGROUND OF THE INVENTION

This invention relates to polypeptide hormone analogues that exhibits enhanced pharmaceutical properties, such as increased biological potency, more rapid pharmacokinetics, and/or augmented resistance to thermal fibrillation above room temperature. More particularly, this invention relates to insulin analogues that are modified by attachment of O-link carbohydrate moieties at positions B27 and/or B30. Such non-standard sequences may optionally contain standard amino-acid substitutions at other sites in the A or B chains of an insulin analogue.

The engineering of non-standard proteins, including therapeutic agents and vaccines, may have broad medical and societal benefits. An example of a medical benefit would be optimization of the pharmacokinetic properties of a protein. An example of a further societal benefit would be the engineering of proteins more refractory than standard proteins with respect to degradation at or above room temperature for use in regions of the developing world where electricity and refrigeration are not consistently available. An example of a therapeutic protein is provided by insulin. Analogues of insulin containing non-standard amino-acid substitutions may in principle exhibit superior properties with respect to biological activity, pharmacokinetics or resistance to thermal degradation. The challenge posed by the pharmacokinetics of insulin absorption following subcutaneous injection affects the ability of patients to achieve tight glycemic control and constrains the safety and performance of insulin pumps. The challenge posed by its physical degradation is deepened by the pending epidemic of diabetes mellitus in Africa and Asia. These issues are often coupled as modifications known in the art to accelerate absorption following subcutaneous injection usually worsen the resistance of insulin to chemical and/or physical degradation. Because fibrillation poses the major route of degradation above room temperature, the design of fibrillation-resistant formulations may enhance the safety and efficacy of insulin replacement therapy in such challenged regions. The present invention pertains to the use of an O-linked carbohydrate-modified residue at B27 and/or B30 in combination with standard or non-standard substitutions elsewhere in the A-chain or B-chain or in combination with C-terminal extension of the B-chain as a novel strategy to modify and improve distinct properties of insulin. During the past decade specific chemical modifications to the insulin molecule have been described that selectively modify one or another particular property of the protein to facilitate an application of interest. Whereas at the beginning of the recombinant DNA era (1980) wild-type human insulin was envisaged as being optimal for use in diverse therapeutic contexts, the broad clinical use of insulin analogues in the past decade suggests that a suite of analogues, each tailored to address a specific unmet clinical need, would provide significant medical and societal benefits.

Administration of insulin has long been established as a treatment for diabetes mellitus. Insulin is a small globular protein that plays a central role in metabolism in vertebrates. Insulin contains two chains, an A chain, containing 21 residues, and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). A variety of evidence indicates that it consists of an insulin-like core and disordered connecting peptide (FIG. 1B). Formation of three specific disulfide bridges (A6-A11, A7-B7, and A20-B19; FIGS. 1A and 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). The sequence of insulin is shown in schematic form in FIG. 1C. Individual residues are indicated by the identity of the amino acid (typically using a standard three-letter code), the chain and sequence position (typically as a superscript). Pertinent to the present invention is the designation of individual atoms in the amino acids Serine and Threonine, which each contain a hydroxyl group (—OH) attached to the beta carbon ($C_\beta$) of their respective side chains. By convention the oxygen atom attached to $C_\beta$ is denoted $O^\beta$.

The pharmacokinetic features of insulin absorption after subcutaneous injection have been found to correlate with the rate of disassembly of the insulin hexamer. Although not wishing the present invention to be constrained by theory, modifications to the insulin molecule that lead to accelerated disassembly of the insulin hexamer are thought to promote more rapid absorption of insulin monomers and dimers from the subcutaneous depot into the bloodstream. A major goal of insulin replacement therapy in patients with diabetes mellitus is tight control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinapathy, blindness, and renal failure. Because the pharmacokinetics of absorption of wild-type human insulin following subcutaneous injection is often too slow and too prolonged relative to the physiological requirements of post-prandial metabolic homeostasis, considerable efforts have been expended during the past 20 years to develop insulin analogues that exhibit more rapid absorption with pharmacodynamic effects that are more rapid in onset and less prolonged in duration. Examples of such rapid-acting analogues known in the art are [$Lys^{B28}$, $Pro^{B29}$]-insulin (KP-insulin, the active component of Humalog®), [$Asp^{B28}$]-insulin (Novalog®), and [$Lys^{B3}$, $Glu^{B29}$]- insulin (Apidra®). These products contain standard amino-acid substitutions, which change the pattern of positive or negative charges in the molecule and which, in the case of KP-insulin or [Asp$^{B28}$]-insulin, respectively relocate or remove the distinctive pyrrolidine ring of Proline (an imino acid) at position B28. Although widely used in clinical practice, these analogues exhibit two principal limitations. First, although their pharmacokinetic and pharmacodynamic profiles are more rapid than those of wild-type insulin, they are not rapid enough in many patients to optimize glycemic control or enable the safe and effective use of algorithm-based insulin pumps (closed-loop systems). Second, the amino-acid substitutions in these analogues impair the thermodynamic stability of insulin and exacerbate its susceptibility to fibrillation above room temperature. Thus, the safety, efficacy, and real-world convenience of these products have been limited by a trade-off between accelerated absorption and accelerated degradation. Because of this trade-off (which pertains to present products Humalog®, Novalog®, and Apidra® and which is reflected in instructions to patients in package inserts to inspect vials for signs of degradation), it has seemed not possible to identify substitutions that simultaneously enhance the rate of hexamer disassembly and retard formation of fibrils above room temperature.

Fibrillation, which is a serious concern in the manufacture, storage and use of insulin and insulin analogues for the treatment of diabetes mellitus, is enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, patients with diabetes mellitus optimally must keep insulin refrigerated prior to use. Fibrillation of insulin or an insulin analogue can be a particular concern for such patients utilizing an external insulin pump, in which small amounts of insulin or insulin analogue are injected into the patient's body at regular intervals. In such a usage, the insulin or insulin analogue is not kept refrigerated within the pump apparatus, and fibrillation of insulin can result in blockage of the catheter used to inject insulin or insulin analogue into the body, potentially resulting in unpredictable fluctuations in blood glucose levels or even dangerous hyperglycemia. At least one recent report has indicated that insulin Lispro (KP-insulin, an analogue in which residues B28 and B29 are interchanged relative to their positions in wild-type human insulin; trade name Humalog®) may be particularly susceptible to fibrillation and resulting obstruction of insulin pump catheters. Insulin exhibits an increase in degradation rate of 10-fold or more for each 10° C. increment in temperature above 25° C.; accordingly, guidelines call for storage at temperatures <30° C. and preferably with refrigeration. The propensity of current products Humalog®, Novalog®, and Apidra® to form fibrils at or above room temperature is exacerbated on dilution, as may be used in the treatment of Type I diabetes mellitus in children or adults with low body mass. Accordingly, the shelf life of such diluted pharmaceutical formulations in use at room temperature is reduced in accordance with instructions contained in package inserts regarding disposal of diluted insulin analogue formulations. Fibrillation of basal insulin analogues formulated as soluble solutions at pH less than 5 (such as Lantus® (Sanofi-Aventis), which contains an unbuffered solution of insulin glargine and zinc ions at pH 4.0) also can limit their self lives due to physical degradation at or above room temperature; the acidic conditions employed in such formulations impairs insulin self-assembly and weakens the binding of zinc ions, reducing the extent to which the insulin analogues can be protected by sequestration within zinc-protein assemblies.

The present theory of protein fibrillation posits that the mechanism of fibrillation proceeds via a partially folded intermediate state, which in turn aggregates to form an amyloidogenic nucleus. In this theory, it is possible that amino-acid substitutions that stabilize the native state may or may not stabilize the partially folded intermediate state and may or may not increase (or decrease) the free-energy barrier between the native state and the intermediate state. Therefore, the current theory indicates that the tendency of a given amino-acid substitution in the insulin molecule to increase or decrease the risk of fibrillation is highly unpredictable. Protein- and peptide fibrils ordinarily derive from non-glycosylated proteins. Insulin, for example, contains no O-linked carbohydrate moieties (despite having Threonine residues as potential sites of modification at positions A8, B27, and B30 and having Serine residues as potential sites of modification at positions A9 and A12) and similarly no N-linked carbohydrate moieties (despite having Asparagine residues as potential sites of modification at positions A18, A21, and B3, having Glutamine at position A5, A15 and B4, and having Arginine at position B22). Although the native amino-acid sequences surrounding these residues do not specify their glycosylation in the endoplasmic reticulum or Golgi apparatus of pancreatic beta cells, such modifications may be introduced in vitro through chemical synthesis. O-linked or N-linked carbohydrate moieties at one or more of these positions would introduce a cyclic polar adduct (pyranosides) containing multiple hydrogen-bond donors and hydrogen-bond receptors. Such a residue-specific modification would therefore be expected to modify the solvation of the modified polypeptide chain and could thereby modify the relative stabilities of the native state, partially folded state, and non-native aggregates pertinent to the mechanism of fibrillation. While not wishing to be constrained by theory, it is possible that such modified glycopeptides-water interactions and potential glycopeptides-glycopeptide could augment the kinetic barrier that ordinarily protects the native state of a protein from formation of an amyloidogenic seed and could thereby delay the onset of fibrillation. While further not wishing to be constrained by theory, it seemed possible that reorganization of the water structure surrounding the carbohydrate moiety and in particular disruption of bridging water molecules involved in a network of hydrogen bonds at the outer surface of the insulin hexamer could lead to accelerated disassembly of the hexamer, thus circumventing the trade-off that thwarted previous attempts to optimize simultaneously resistance to insulin fibrillation and rate of hexamer disassembly. We further envisaged that the protective effects of carbohydrate modification would be operative under a broad range of pH conditions, including under acidic conditions employed in the formulation of basal insulin analogues (pH 3-4) whose isoelectric points are shifted to near neutrality as exemplified by insulin glargine, so long as the specific monosaccharide pyranoside adduct either did not contain a formal charge or was incorporated into a protein framework in which the overall isoelectric point was maintained to be near neutrality (pH 7) due to amino-acid substitutions or extensions elsewhere in the A- or B-chains as known in the art.

Two general considerations motivated the specific molecular designs disclosed in this application: (i) avoidance of competing high-affinity binding to membrane carbohydrate-binding proteins and (ii) avoidance of steric occlusion of the receptor-binding surface of insulin, i.e., that surface of insulin that mediates its binding to and activation of the insulin receptor. We describe these avoidance strategies as follows.

(i) Mammalian cells contain cell-surface proteins that recognize with high affinity branched-chain oligosaccharide moieties covalently tethered to proteins by O-ester linkages (to the β-hydroxyl function of Serine or Threonine) or by N-ester linkages (to the side-chain carboxamide function of Asparagine or Glutamine and to the guanadinium group of Arginine). The affinities and specificities of such membrane proteins vary but in general the strength of binding is markedly enhanced by having two or more sites of carbohydrate modification, by having branched carbohydrate moieties, and by exhibiting appropriate terminal carbohydrate units that are complementary to the binding site or binding sites of the membrane protein. High affinity is a consequence of multidentate interactions with such branching carbohydrate adducts. An example of such a membrane protein is the human mannose receptor, which binds with nanomolar or subnanomolar affinity branched-chain carbohydrate moieties that terminate in the hexose mannose or that terminate in a sulfated form of the hexose N-acetyl-galactose. Such high-affinity binding would be undesirable in an insulin analogue as binding of the hormone to a carbohydrate-binding membrane receptor would be likely to compete with binding of the hormone to the insulin receptor, which mediates the biological activities of insulin. We therefore sought to invent analogues of insulin containing single hexose modifications, intended to confer protection from fibrillation while avoiding competitive binding to and clearance by membrane carbohydrate-binding proteins. Examples of single hexose modifications are provided by an alpha-O-ester linkage between mannose, glucose, or N-acetyl-galactose to Threonine as corresponding pyranosides. The structure of mannose as a free cyclic structure (D-mannopyranoside) is shown in FIG. 2A. The structure of an N-acetyl-β-D-galactopyranoside is shown in FIG. 2B with an $O^{\beta}$-linkage to Serine (right) and potentially extended by other linked carbohydrates (wavy line at left; in a monosaccaride adduct the moiety at left would terminate as —OH).

(ii) The primary receptor-binding surface of insulin spans residues A1-A14 and B6-B26. Restriction of carbohydrate modification to sites outside of these peptide segments would therefore be expected to be associated with at least a portion of the receptor-binding activity and biological potency of insulin. Examples of sites outside of the receptor-binding surface of insulin are provided by $Thr^{B27}$ and $Thr^{B30}$.

Although residues B26-B30 may be deleted from insulin without loss of receptor-binding activity and so might be modifiable with retention of at least a portion of the biological potency of insulin, modifications in this segment that are known in the art to confer more rapid absorption of insulin from a subcutaneous depot also confer inferior physical stability relative to human insulin. Examples of provided by prandial insulin analogues insulin lispro ([$Lys^{B28}$, $Pro^{B29}$]-insulin, herein abbreviated KP-insulin; the active component of Humalog® (Eli Lilly and Co.)), insulin aspart ($Asp^{B28}$-insulin; the active component of Novolog® (Novo-Nordisk LLC)). Such impaired physical stability reflects the same structural mechanism as accelerated absorption: partial structural perturbation of the native dimerization surface of insulin (as found at three subunit interfaces of the insulin hexamer) both leads to accelerated absorption and accelerated fibrillation. It is not obvious how this segment might be modified in such a way as to confer accelerated hexamer disassembly while also protecting the insulin monomer from fibrillation. Simultaneous enhancement of the rate of hexamer disassembly and resistance to physical degradation would require a physical principle unrelated to those that underlie the design of insulin analogues that are known in the art. While not wishing to be constrained by theory, we envisaged that residue-specific modification of the solvation properties at the surface of the insulin monomer, dimer, and hexamer by means of carbohydrate modification at sites peripheral to the receptor-binding surface could simultaneously confer accelerated hexamer disassembly and enhanced protection from fibrillation with maintenance of at least a portion of the biological activity of wild-type insulin.

There is a need, therefore for an insulin analogue that displays increased resistance to fibrillation above room temperature while retaining rapid hexamer disassembly and while exhibiting at least a portion of the activity of the corresponding wild-type insulin and maintaining at least a portion of its chemical and/or physical stability.

SUMMARY OF THE INVENTION

It is, therefore, an aspect of the present invention to provide insulin analogues that provide augmented resistance to fibrillation above room temperature while retaining rapid hexamer disassembly and hence accelerated absorption following subcutaneous injection. The present invention addresses previous limitations for fast-acting insulin analogues, namely, that they are more susceptible to fibrillation than wild-type insulin. The claimed invention exploits the natural occurrence of Threonine residues at positions B27 and B30 and the feasibility of trypsin-mediated semi-synthesis to attach synthetic peptides modified by carbohydrate adducts at these sites to the prefolded core of insulin (designated des-octapeptide[B23-B30]-insulin; DOI) containing residues B1-B22 and A1-A21 connected by the three native disulfide linkages (cystines A6-A11, A7-B7, and A20-B19). Trypsin-mediated semi-synthesis also permits native attachment of peptides shorter or longer than eight amino acids, peptides containing one or more carbohydrate moieties linked to variant peptides containing Serine, Asparagine or Glutamine instead of Threonine or containing one or more carbohydrate moieties linked to variant peptides containing Serine, Asparagine, Glutamine, or Threonine at positions other than B27 and B30. All such peptides must lack an internal tryptic site and contain a Glycine at their respective N-termini to provide an insulin analogue that retains significant biological activity. The semi-synthetic preparation of insulin analogues containing one or more carbohydrate adducts in the B-chain at a position or positions C-terminal to $Gly^{B23}$ is also feasible in combination with variants of DOI containing amino-acid substitutions elsewhere in the A- or B-chains provided that the residue at position B22 is Arg or Lys.

The essence of this invention is that modification of $Thr^{B27}$ and/or $Thr^{B30}$ by a monosaccharide pyranoside may be efficiently be accomplished by trypsin-mediated semi-synthesis and can introduce one or more of the following favorable properties: (i) protect the protein from fibrillation above room temperature; (ii) maintain at least a portion of the insulin-receptor-binding affinity and biological activity of wild-type human insulin; (iii) in cases in which the parent non-glycosylated insulin analogue is able to form dimers, hexamers, and/or zinc-stabilized hexamers, the monosaccaride pyranoside adduct would maintain at least a portion of such competence for self-assembly; (iv) in cases in which the parent non-glycosylated insulin analogue exhibits an isoelectric point (pI) shifted to near pH 7 such that pH-dependent self-assembly, aggregation, and/or insolubility occurs in the subcutaneous depot, the monosaccaride pyranoside adduct would maintain at least a portion of such pH-dependent self-assembly, aggregation, and/or insolubility; and (v) in cases in which the parent non-glycosylated insulin analogue is unable to form dimers, hexamers, and/or zinc-stabilized hexamers, the monosaccaride pyranoside adduct would not confer or restore competence for such self-assembly.

It is possible that the above analogues may also be prepared by total chemical synthesis of the glycosylated insulin B-chain followed by standard insulin-chain combination employing a synthetic A-chain (or A-chain variant) or employing an A-chain obtained from biosynthetic insulin by oxidative sulfitolysis. Although of low yield, insulin chain combination would permit the introduction of the carbohydrate adduct at other sites in the A- or B-chains, such as at $Thr^{A8}$ or following substitution of $Tyr^{A14}$ by corresponding monosaccaride adducts of Ser, Thr, Asn, or Gln; the feasibility of this method of preparation is limited by the inefficiency of disulfide pairing, which may be further impaired by the modification. Except in the presence of glycosylation of the side chain of B30, it is possible that the remaining subset of the above analogues may be prepared by a recently described protocol for the total chemical synthesis of insulin analogues in which an ester linkage is introduced between the side chains of $Thr^{B30}$ and $Glu^{A4}$ as a synthetic intermediate (Sohma, Y., Hua, Q. X., Whittaker, J., Weiss, M. A. & Kent, S. B. H. (2010) Design and folding of [$Glu^{A4}$($O^{\beta}$-$Thr^{B30}$)]insulin ("Ester Insulin"): a minimal proinsulin surrogate chemically convertible to human insulin. *Angew. Chem. Int. Ed.* 49, 5489-5493). It is also possible that derivatives of insulin containing one or more O- or N-linked carbohydrate adducts may be obtained through the total chemical synthesis of a variant proinsulin or single-chain polypeptide precursor wherein the reduced polypeptide chain contains one or more modified amino-acids. A protocol for the total chemical synthesis of proinsulin by native fragment ligation has been described (Luisier, S., Avital-Shmilovici, M., Weiss, M. A. & Kent, S. B. H. (2010) Total chemical synthesis of human proinsulin. *Chem. Comm.* 46, 8177-8179); a protocol for the total chemical synthesis of a foreshortened single-chain precursor by standard solid-phase peptide synthesis has also been described (Hua, Q. X., Hu, S. Q., Frank, B. H., Jia, W., Chu, Y. C., Wang, S. H., Burke, G. T., Katsoyannis, P. G. & Weiss, M. A. (1996) Mapping the functional surface of insulin by design: structure and function of a novel A-chain analogue. *J. Mol. Biol.* 264, 390-403). Such alternative synthetic routes offer the advantages of flexibility in the positioning of the monosaccaride pyranoside adduct in the A-chain and/or B-chain, but incur a requirement for native and efficient disulfide pairing in the presence of one or more such modification.

The semi-synthetic protocol employed in the examples disclosed herein circumvents potential barriers posed by disulfide pairing and protein folding based on its order of steps; i.e., DOI is generated from a prefolded insulin, proinsulin, or foreshortened single-chain insulin analogue. This folding prior to tryptic digestion circumvents any folding defect that may otherwise be introduced by the desired monosaccaride adduct or adducts. The same advantages would pertain to the semi-synthesis of insulin analogues containing di-saccaride adducts, tri-saccaride adducts, or branched polysaccaride adducts at positions B27, B30, or other sites between $Gly^{B23}$ and the C-terminus of the B-chain.

In general, the present invention provides an insulin analogue comprising a modified B-chain polypeptide that contains one or more monosaccaride adducts at positions B27 and/or B30 and in combination with other amino-acid substitutions in the insulin molecule or in combination with C-terminal extension of the B-chain. In one example the B-chain contains α-D-mannopyranoside as a $O^{\beta}$-linked side-chain modification of $Thr^{B27}$ in combination with substitutions $Pro^{B28} \rightarrow Lys$ and $Lys^{B29} \rightarrow Pro$ (designated mannose-$Thr^{B27}$-KP-insulin); the latter substitutions are known in the art to confer rapid action as embodied in the product Humalog® (Eli Lilly and Co.). In another example KP-insulin was modified at B27 by O-linked N-acetyl-β-D-galactose (designated GalNAc-$Thr^{B27}$-KP-insulin). In another example the insulin analogue contains a monosaccaride pyranoside adduct at position B30 (mannose-$Thr^{B30}$) in combination with (i) a modified A-chain containing substitutions $His^{A4}$, $His^{A8}$, and $Gly^{A21}$; and (ii) a modified B-chain containing Ornithine (Orn) at position B29 and Orn at position B31 as an extension of the B-chain. The A-chain substitutions $His^{A4}$ and $His^{A8}$ confer "zinc stapling" and a partial shift in pI toward neutrality as disclosed in International Patent Application No. PCT/US2007/00320 and pending U.S. patent application Ser. No. 12/160,187 and incorporated by reference herein; the A-chain modification $Gly^{A21}$ in combination with substitutions at positions A4 and A8 confers partial protection from chemical degradation under acidic conditions as disclosed in pending U.S. patent application Ser. No. 13/393,745 and incorporated by reference herein; the B-chain modification $Orn^{B29}$ is believed to prevent tryptic digestion at $Lys^{B29}$; and the B-chain extension $Orn^{B31}$ is believed to extend the shift in pI due to A-chain substitutions $His^{A4}$ and $His^{A8}$ further toward physiological pH.

In one particular set of embodiments, the B-chain polypeptide comprises an amino-acid sequence selected from the group consisting of SEQ ID NOS. 7-47 and polypeptides having three or fewer additional amino-acid substitutions thereof. In yet another particular set of embodiments, designated halogenated insulin analogues, the B-chain polypeptide contains pentafluoro-Phe at position B24 or a single halogen modification (mono-fluoro, mono-chloro, or mono-bromo) at $Phe^{B24}$ or $Phe^{B25}$; the modification may be at the ortho, meta, or para position of the aromatic ring (corresponding to ring positions 2, 3, and 4, respectively). Such halogen modifications were disclosed in pending U.S. patent application Ser. No. 13/018,011, which is incorporated by reference herein. In addition or in the alternative, the insulin analogue may contain a non-halogenated unnatural amino-acid substitution at position 24 of the B-chain; examples include Cyclohexanylalanine (Cha), 2-methyl-Phe, 3-methyl-Phe, or 4-methyl-Phe as disclosed in pending U.S. patent application Ser. No. 12/884,943 which is incorporated by reference herein. In addition or in the alternative, the insulin analogue may contain an amino-acid substitution at position A8 whereby the β-branched side chain in wild-type insulin ($Thr^{A8}$) is substituted by a non-β-branched polar or charged side chain, such as Arg, Gln, Glu, His, or Lys. As part of the present invention, the A-chain of the des-pentapeptide[B23-B30]-insulin analogue employed in semi-synthesis may optionally be selected from one of the variant A-chain sequences given in SEQ ID NO: 48-52.

The invention also provides a method of preparation of the above analogues by trypsin-mediated semi-synthesis in which a prefolded disulfide-bridged fragment of insulin (DOI) is linked by formation of a peptide bond between $Arg^{B22}$ and $Gly^{B23}$ to a synthetic peptide containing an N-terminal Glycine, is of length between 7 and 15 residues, lacks an internal tryptic cleavage site, and contains one or more O-linked monosaccharide pyranoside adducts.

The invention also provides a method of treating a patient. The method comprises administering a physiologically effective amount of an insulin analogue or a physiologically acceptable salt thereof to the patient, wherein the insulin analogue or a physiologically acceptable salt thereof contains a variant B-chain polypeptide containing a monosaccharide pyranoside adduct at position B27 and/or B30 in combination of one or more additional substitutions at sites B24, B28, B29, and A8 or in combination with a C-terminal extension of the B-chain as described above. In one embodiment, the monosaccharide pyranoside adduct may be α-D-mannopyranoside, α-D-glucopyranoside, or N-acetyl-β-D-galactopyranoside. In such an embodiment, the modified B-chain in the insulin analogue administered to a patient may otherwise have the amino-acid sequence of human insulin or may contain standard amino-acid substitutions known in the art to confer rapid action; these include [$Lys^{B28}$, $Pro^{B29}$] (as in Humalog®), $Asp^{B28}$ (as in Novolog®), [$Lys^{B3}$, $Glu^{B29}$] (as in Apidra®), or an acidic residue at position B10 ($Asp^{B10}$ or $Glu^{B10}$). In another embodiment the insulin analogue contains one or more substitutions to remove an acidic amino-acid side chain or introduce a basic amino-acid side chain in order to shift its isoelectric point toward neutrality as known in the art to confer protracted action. In yet another embodiment the insulin analogue contains additional Histidine residues to enable the binding of zinc ions in addition to the axial zinc ions that are known in the art to mediate classical hexamer assembly. In still another embodiment, the insulin analogue is a mammalian insulin analogue, such as an analogue of human insulin. In one particular set of embodiments, the variant B-chain contains Cyclohexanylalanine at position B24 or a monomethyl modification of $Phe^{B24}$; or contains one or more halogen atoms within the aromatic ring of $Phe^{B24}$, $Phe^{B25}$, or $Tyr^{B26}$. In another particular set of embodiments, the B-chain polypeptide comprises an amino-acid sequence selected from the group consisting of SEQ ID NOS.: 11-47 and polypeptides having three or fewer additional amino-acid substitutions thereof.

BRIEF DESCRIPTION OF THE SEVERAL VIEWS OF THE DRAWINGS

FIG. 1B is a structural model of proinsulin, consisting of an insulin-like moiety and a disordered connecting peptide (dashed line).

FIG. 3 provides a ribbon model of a putative insulin monomer containing an O-linked mannosylpyranoside modification of $Thr^{B27}$: (A) stick model of adduct and (B) space-filling model of adduct. In each panel the A-chain ribbon is shown in light gray and the B-chain ribbon is shown in dark gray. The structures represent the T state (Protein Databank entry 4INS). The mannosylpyranoside projects from the surface of the monomer.

FIG. 4 provides a ribbon model of a putative insulin dimer containing O-linked mannosylpyranoside modifications of $Thr^{B27}$ and its dimer-related mate at opposite ends of an anti-parallel β-sheet: (A) stick model of adducts and (B) space-filling model of adducts. In each panel the A-chain ribbon is shown in light gray and the B-chain ribbon is shown in dark gray. The structures represent the $T_2$ state (Protein Databank entry 4INS). The two mannosylpyranoside adducts project from the surface of the dimer.

FIG. 5 provides a ribbon model of a putative insulin hexamer containing O-linked mannosylpyranoside modifications of $Thr^{B27}$ in each of the three component dimers: (A) stick model of adducts and (B) space-filling model of adducts. In each panel the A-chain ribbon is shown in light gray and the B-chain ribbon is shown in dark gray. The structures represent the $T_6$ state (Protein Databank entry 4INS). The mannosylpyranoside projects from the surface of the monomer.

FIG. 7C provides a histogram that summarizes the initial rate of decrease (mg/min) in blood glucose concentration in the diabetic rats on subcutaneous injection of insulin analogues at low (blue bars) or high dose (red bars).

DETAILED DESCRIPTION OF THE INVENTION

Figure 1A:
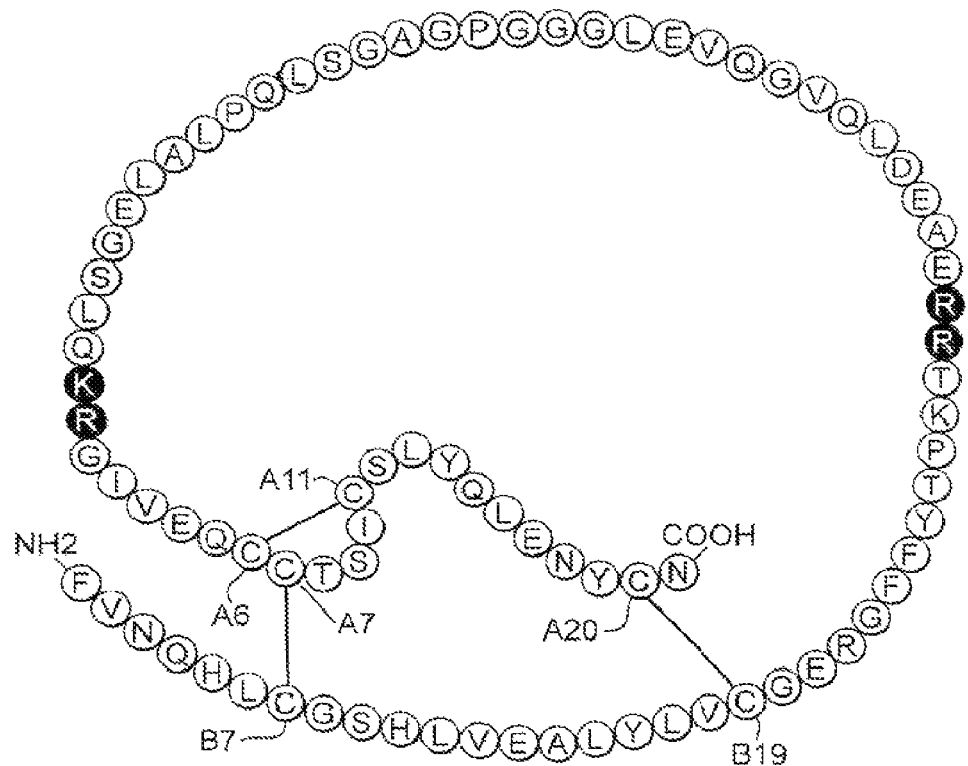
FIG. 1A is a schematic representation of the sequence of human proinsulin including the A- and B-chains and the connecting region shown with flanking dibasic cleavage sites (filled circles) and C-peptide (open circles).
Figure 1C:
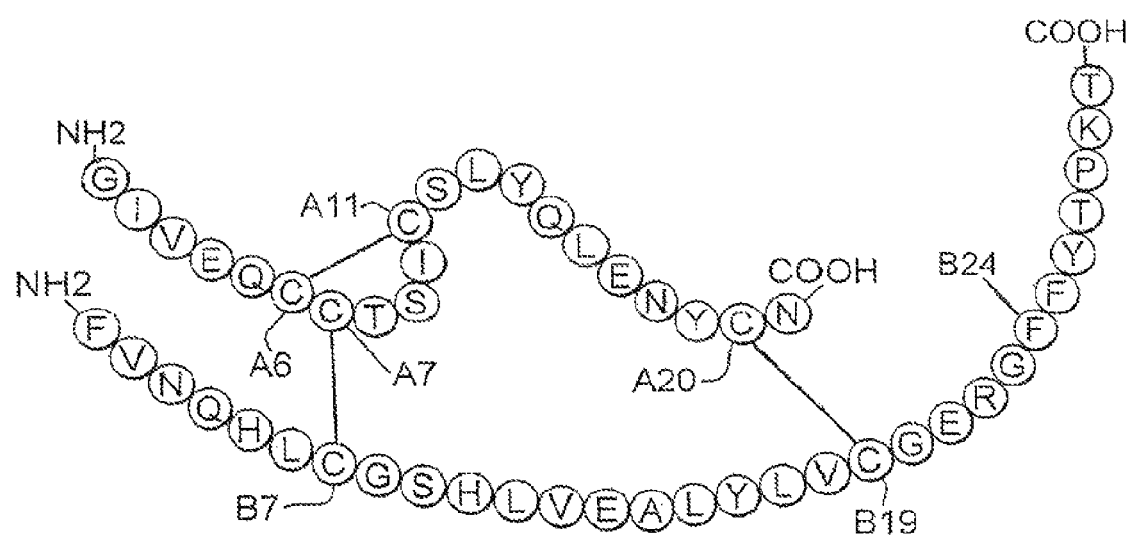
FIG. 1C is a schematic representation of the sequence of human insulin indicating the position of residues B27 and B30 in the B-chain.
Figure 2A:
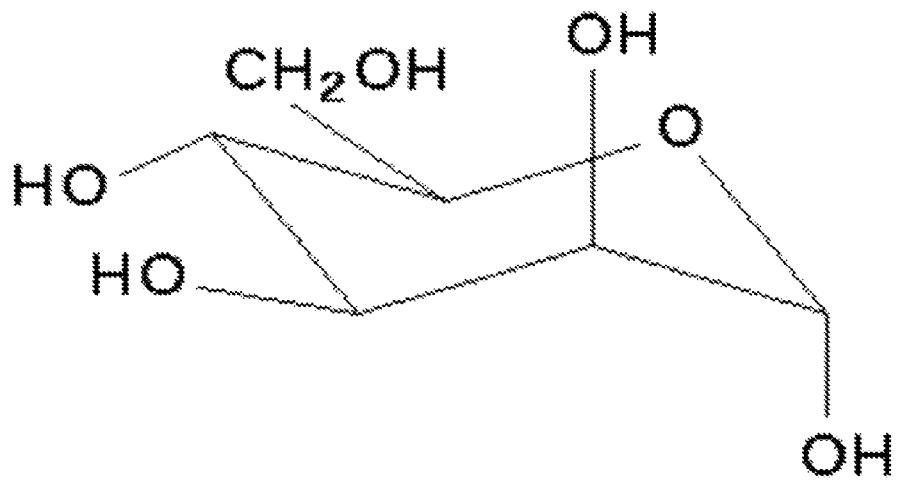
FIG. 2A provides the structure of mannosylpyranoside.
Figure 2B:
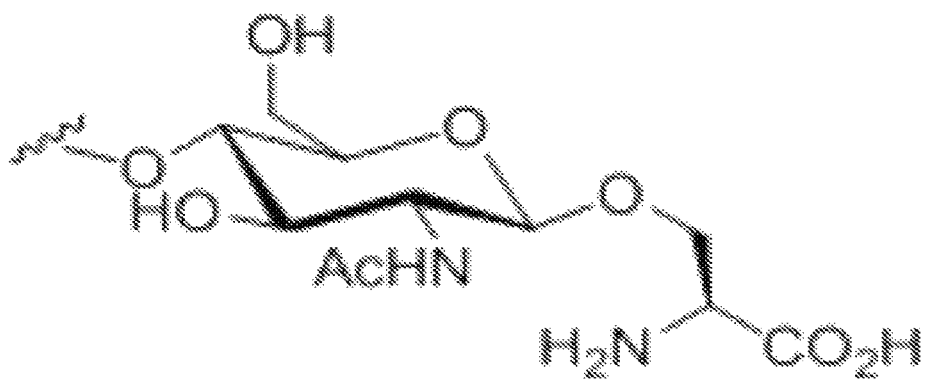
FIG. 2B provides the structure of an O-linked N-acetyl-galactosylpyranoside; the wavy line at left indicates linked protein.

The present invention is directed toward an insulin analogue that provides resistance to fibrillation above room temperature due to site-specific modification of the C-terminal region of the B-chain by a monosaccharide pyranoside. Application to rapid-acting insulin analogues provides a next generation of such analogues that retain rapid hexamer disassembly and where the analogue maintains at least a portion of biological activity of the corresponding unmodified insulin or insulin analogue. Application to basal insulin analogues engineered to exhibit a shift of their isoelectric point to near neutrality provides a next generation of such analogues that retain pH-dependent aggregation with reduced solubility at physiological pH such that the analogue maintains at least a portion of biological activity and protracted action of the corresponding unmodified insulin or insulin analogue. As used in this specification and the claims, various amino acids in insulin or an insulin analogue may be noted by the amino-acid residue in question, followed by the position of the amino acid, optionally in superscript. The position of the amino acid in question includes the A- or B chain of insulin where the substitution is located. Thus, Phe$^{B1}$ denotes a phenylalanine as the first amino acid of the B chain of wild-type insulin; Val$^{B2}$ the second amino acid of the B-chain of wild-type insulin; and so forth until Thr$^{B30}$ at the C-terminal position. On removal of residues B1-B3, this numbering is retained such that Glu$^{B4}$ would be the first amino acid of the des-[B1-B3] B-chain, Phe$^{B24}$ is the 21$^{st}$ amino acid of the des-[B1-B3] B-chain, and so forth.

The present invention pertains to modification of Thr$^{B27}$ or Thr$^{B30}$ by an $O^β$-linked monosaccharide pyranoside (α-D-mannopyranoside-$O^β$-Thr, N-acetyl-β-D-galactopyranoside-$O^β$-Thr, and α-D-glucopyranoside-$O^β$-Thr). The side chains at positions B27 and B30 project into solvent in crystal structures of insulin dimers and hexamers and also project in solvent in NMR structures of engineered insulin monomers. Whereas Thr$^{B30}$ is not well ordered, Thr$^{B27}$ projects into solvent from a β-strand (residues B24-B28), which on dimerization forms an anti-parallel β-sheet with partner strand (residues B24'-B28'). The monosaccharide pyranoside is hydrophilic and in principle would be expected to alter the pattern of hydration and network of water-linked hydrogen bonds at the surface of the insulin monomer, dimer, and hexamer. Examples of hydrophilic monosaccharide pyranosides are provided by mannose, N-acetylgalactose, and glucose. A molecular model of α-D-mannopyranose-$O^β$-Thr$^{B27}$-insulin is shown as a monomer in FIG. 3A, as a dimer in FIG. 3B, and as a hexamer in FIG. 3C. No steric interference between the adduct and other portions of the insulin molecule is predicted by these models.

Attachment of such hydrophilic ring structures to the HO$^β$-function of the side chain of Thr$^{B27}$ or Thr$^{B30}$ could be replaced by attachment of such hydrophilic ring structures to the HO$^β$-function of the side chain of Ser$^{B27}$ or Ser$^{B30}$. An analogue of the present invention may contain a single site of $O^β$-linked glycosylation at positions B27 or B30 or may contain simulataneous modification of residues B27 and B30. The latter analogues may contain the same monosaccharide at both positions or may contain one type of mono saccharide at B27 and a different type of monosaccharide at B30. For synthetic convenience modification of Thr$^{B30}$ or Ser$^{B30}$ is ordinarily undertaken in the context of a C-terminal extension of the B-chain by one residue (B31) or two residues (B31-B32). In the case of rapid-acting analogues it is preferred that such extensions contain at least one side chain with a negative charge (Asp or Glu); the incase of basal insulin analogues it is preferred that such extensions contain at least one side chain with a positive charge and may optionally be amidated to remove the negative charge ordinarily present at the C-terminal carboxylate of a peptide or protein at neutral pH. Tryptic mediated semi-synthesis of all of the above analogues is simplest to implement when the synthetic octapeptide, nonapeptide, or decapeptide lacks an internal tryptic site. All such peptides contain an N-terminal Glycine, which on tryptic-mediated semi-synthesis assumes position B23 of the B chain.

In one embodiment, the present invention provides an insulin analogue that provides more rapid hexamer disassembly by modification of Threonine at position B27 by an $O^\beta$-linked mannosyl moiety in the context of KP-insulin. In another particular embodiment the modification of Threonine at position B27 by an $O^\beta$-linked N-acetyl-galactose moiety in the context of KP-insulin. In yet another embodiment the $O^\beta$-linked N-acetyl-galactose moiety at $Thr^{B27}$ was introduced in the context of a model of wild-type human insulin in which $Lys^{B29}$ was substituted by its near isostere Ornithine, which like Lysine bears a positively charged side-chain amino group. In a further embodiment the variant "KP" B chain modified at $Thr^{B27}$ by an $O^\beta$-linked N-acetyl-galactose moiety is combined with a variant A chain containing Histidine at position A8. The present invention is not limited, however, to insulin analogues containing a monosaccharide modification at position B27. In another set of embodiments the monosaccharide modification lies at position B30 in the context of an extended B chain. In one set $O^\beta$-mannosyl-$Thr^{B30}$ was introduced in the context of a 31-residue B chain containing Ornithine at positions B29 and B31. In another particular embodiment the latter 31-residue B chain containing α-D-mannopyranoside-$O^\beta$-$Thr^{B30}$ containing Ornithine at positions B29 and B31 was combined with the wild-type A chain; in yet another particular embodiment the latter 31-residue B chain was combined with a variant A chain containing substitutions $His^{A4}$, $His^{A8}$, and $Gly^{A21}$. In another particular embodiment the $Orn^{B29}$-mannosyl-$Thr^{B30}$-$Orn^{B31}$ element is combined with the substitution $Glu^{B13} \rightarrow Gln$, resulting in a shift in predicted isoelectric point to near neutrality as is characteristic of basal insulin analogues. It is envisioned that insulin analogues of the present invention may employ $O^\beta$-linked monosaccharide modifications of $Ser^{B27}$ and/or $Ser^{B30}$ as near-isosteric analogues of the corresponding $O^\beta$-linked monosaccharide modifications of $Thr^{B27}$ and/or $Thr^{B30}$.

It is envisioned that the insulin analogues of the present invention may contain monosaccharide adducts at both positions B27 and B30, independently chosen from the group mannose, N-acetyl-galactose, and glucose. A potential example of B27-B30 homo-adducts would be a derivative of insulin containing mannose at $Thr^{B27}$ and mannose at $Thr^{B30}$ in the context of a "KP" B chain containing two-residue acidic B-chain extension $Glu^{B31}$-$Glu^{B32}$; a potential example of B27-B30 hetero-adducts would be a derivative of insulin containing mannose at $Thr^{B27}$ and glucose at $Thr^{B30}$ in the same extended B-chain context. Although each of these monosaccharide pyranosides provides a hydrophilic cyclic adduct, each may confer distinct biological properties in relation to cell-surface receptors encountered in the subcutaneous depot, encountered on the luminal surfaces of blood vessels, and/or encountered on the surface of target tissues.

It is also envisioned that these substitutions may also be made in animal insulins such as porcine, bovine, equine, and canine insulins, by way of non-limiting examples. In addition or in the alternative, the insulin analogue of the present invention may contain a deletion of residues B1-B3 or may be combined with a variant A chain containing a non-beta-branched side chain at position A8, such a nitrogen-containing side chains (Trp, His, Gln, Arg, or Lys) or the acidic non-beta-branched side chain Glu; the latter A8 substitutions may be combined with monosaccharide modifications at B27 or B30 singly or in combination with the non-standard modifications at positions B24. Examples of non-standard modifications at B24 are provided by substitution of an aromatic hydrogen atom by a larger methyl group (2-$CH_3$-Phe, 3-$CH_3$-Phe, and 4-$CH_3$-Phe), by substitution of one or more aromatic hydrogen atoms by a halogen atoms (pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe), and by substitution of the planar aromatic ring by a nonplanar aliphatic ring (Cyclohexanylalanine). The monosaccharide adducts of the present invention may also be combined with substitutions or chain extensions elsewhere in the insulin molecule that result in a shift in the isoelectric point of the analogue to near neutrality as a mechanism to confer protracted action on subcutaneous injection.

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M) Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids. Standard amino acids may also be substituted by non-standard amino acids belong to the same chemical class. By way of non-limiting example, the basic side chain Lys may be replaced by basic amino acids of shorter side-chain length (Ornithine, Diaminobutyric acid, or Diaminopropionic acid). Lys may also be replaced by the neutral aliphatic isostere Norleucine (Nle), which may in turn be substituted by analogues containing shorter aliphatic side chains (Aminobutyric acid or Aminopropionic acid).

Although not wishing to be constrained by theory, the present invention envisions that monosaccharide adducts at positions B27 and/or B30 alter the solvation and hydrogen-bonding network of water molecules on the surface of the variant B chain and so can delay the onset of fibrillation above room temperature. Because this mechanism of protection does not depend on titrable groups in the monosaccharide in the range pH 3.0-8.0, we envision that such protection will be afforded to rapid-acting analogues at pH 7.0-7.5 and to basal pI-shifted insulin analogues at pH 3.0-4.0. We also envision that, in the case of rapid-acting insulin analogues, changes in solvation and hydrogen-bonding network of water molecules on the surface of the variant insulin hexamers will lead to accelerated rates of hexamer disassembly, thereby enhancing the disassembly properties of insulin lispro ([$Lys^{B28}$, $Pro^{B29}$]-insulin, herein abbreviated KP-insulin), insulin aspart ($Asp^{B28}$-insulin), and related insulin analogues. Further, because of low-affinity binding of such adducts to a variety of cell surface receptors, the present invention envisions that the biological properties of the analogues may also be modified, such as bioavailability following subcutaneous injection, biological potency, or partial hepatoselectivity. Such adducts may also confer binding of the insulin analogues of the present invention to plant lectins, as exemplified by the binding of glucose- or mannose-derivatives of proteins to concanavalin A. It is further envisioned that monosaccharide modifications at positions B27 and/or B30 of the present invention may be made in any of a number of existing insulin analogues. For example, such adducts may be introduced in the context of insulin lispro or in the context of insulin aspart. These analogues are described in U.S. Pat. Nos. 5,149,777 and 5,474,978, the disclosures of which are hereby incorporated by reference herein. These analogues are each known as fast-acting insulins.

The amino-acid sequence of human proinsulin is provided, for comparative purposes, as SEQ ID NO: 1.

```
(human proinsulin)
                                            SEQ ID NO: 1
Phe-Val-Asn-Gln-His-Leu-Cys-Gly-Ser-His-Leu-Val-Gl u-Ala-Leu-Tyr-Leu-Val-Cys-Gly-Glu-Arg-Gly-Phe-Phe- Tyr-Thr-Pro-Lys-Thr-Arg-Arg-Glu-Ala-Glu-Asp-Leu-Gl n-Val-Gly-Gln-Val-Glu-Leu-Gly-Gly-Gly-Pro-Gly-Ala- Gly-Ser-Leu-Gln-Pro-Leu-Ala-Leu-Glu-Gly-Ser-Leu-Gl n-Lys-Arg-Gly-Ile-Val-Glu-Gln-Cys-Cys-Thr-Ser-Ile- Cys-Ser-Leu-Tyr-Gln-Leu-Glu-Asn-Tyr-Cys-Asn
```

The amino-acid sequence of the A chain of human insulin is provided as SEQ ID NO: 2.

```
(human A chain)
                                            SEQ ID NO: 2
Gly-Ile-Val-Glu-Gln-Cys-Cys-Thr-Ser-Ile-Cys-Ser- Leu-Tyr-Gln-Leu-Glu-Asn-Tyr-Cys-Asn
```

The amino-acid sequence of the B chain of human insulin is provided as SEQ ID NO: 3.

```
(human B chain)
                                            SEQ ID NO: 3
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

The amino-acid sequence of the "KP" B chain of prandial insulin analogue KP-insulin contains substitutions Pro$^{B28}$→Lys and Lys$^{B29}$→Pro as provided in SEQ ID NO: 4.

```
                                            SEQ ID NO: 4
Phe-Val-Glu-Gln-His-Leu-Cys-Gly-Ser-Xaa₄-

Leu-Val-Glu-Ala-Leu-Tyr-Leu-Val-Cys-Gly-Glu-Arg-

Gly-Phe-Phe-Try-Thr-Lys-Pro-Thr
```

The 32-residue amino-acid sequence of an extended "KP" B chain of prandial insulin analogue KP-insulin is provided in SEQ ID NO: 5.

```
                                            SEQ ID NO: 5
Phe-Val-Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Try-Thr-Lys-Pro-Thr-Glu-Glu
```

The 31-residue amino-acid sequence of a variant B chain modified and extended to contain Ornithine is provided in SEQ ID NO: 6.

```
                                            SEQ ID NO: 6
Phe-Val-Glu-Gln-His-Leu-Cys-Gly-Ser-Xaa₄-

Leu-Val-Glu-Ala-Leu-Tyr-Leu-Val-Cys-Gly-Glu-Arg-

Gly-Phe-Phe-Try-Thr-Pro-Orn-Thr-Orn
```

The amino-acid sequence of a variant B chain modified by glycosylation at Thr$^{B27}$ is provided in SEQ ID NO: 7.

```
                                            SEQ ID NO: 7
Phe-Val-Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Xaa₁-Lys-Pro-Thr
```

Where Xaa$_1$ is an O$^\beta$-Thr$^{B27}$-linked monosaccharide pyranoside selected from a group consisting of α-D-mannopyranoside, α-D-glucopyranoside, or N-acetyl-β-D-galactopyranoside.

The amino-acid sequence of a variant B chain modified by glycosylation at Ser$^{B27}$ is provided in SEQ ID NO: 8.

```
                                            SEQ ID NO: 8
Phe-Val-Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Xaa₁-Lys-Pro-Thr
```

Where Xaa$_1$ is an O$^\beta$-Ser$^{B27}$-linked monosaccharide pyranoside selected from a group consisting of α-D-mannopyranoside, α-D-glucopyranoside, or N-acetyl-β-D-galactopyranoside.

The amino-acid sequence of a variant B chain modified by glycosylation at Ser$^{B27}$ is provided in SEQ ID NO: 9.

```
                                            SEQ ID NO: 9
Phe-Val-Glu-Gln-His-Leu-Cys-Gly-Ser-Xaa₄-Leu-

Val-Glu-Ala-Leu-Tyr-Leu-Val-Cys-Gly-Glu-Arg-Gly-

Phe-Phe-Tyr-Xaa₁-Lys-Pro-Thr
```

Where Xaa$_1$ is an O$^\beta$-Ser$^{B27}$-linked monosaccharide pyranoside selected from a group consisting of α-D-mannopyranoside, α-D-glucopyranoside, or N-acetyl-β-D-galactopyranoside.

The amino-acid sequence of a variant B chain modified by glycosylation at residue B27 and extended by two residues is provided in SEQ ID NO: 10.

SEQ ID NO: 10
Phe-Val-Glu-Gln-His-Leu-Cys-Gly-Ser-Xaa$_4$-Leu-Val-

Glu-Ala-Leu-Tyr-Leu-Val-Cys-Gly-Glu-Arg-Gly-Phe-

Phe-Tyr-Xaa$_1$-Lys-Pro-Thr-Xaa$_2$-Xaa$_3$

Where Xaa$_1$ is an $O^\beta$-Ser$^{B27}$-linked monosaccharide pyranoside or $O^\beta$-Thr$^{B27}$-linked monosaccharide pyranoside selected from a group consisting of α-D-mannopyranoside, α-D-glucopyranoside, or N-acetyl-β-D-galactopyranoside; and where Xaa$_2$-Xaa$_3$ is a two-residue extension of the B chain containing at least one acidic residue (Glu or Asp).

The amino-acid sequence of a variant B chain modified by glycosylation at residue B27 and an Aspartic acid at position B28 is provided in SEQ ID NO: 11.

SEQ ID NO: 11

Phe-Val-Glu-Gln-His-Leu-Cys-Gly-Ser-$Xaa_4$-Leu-

Val-Glu-Ala-Leu-Tyr-Leu-Val-Cys-Gly-Glu-Arg-Gly-

Phe-Phe-Tyr-$Xaa_1$-Asp-$Xaa_2$-Thr

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside; and where $Xaa_2$ is Pro, Ala or a basic residue selected from the group Lys, norleucine, Orn, diaminobutyric acid or diaminopropionic acid.

The amino-acid sequence of a variant B chain modified by glycosylation at residue B27, Glutamic acid at B29, and an N-terminal deletion of residues B1-B3 is provided in SEQ ID NO: 12.

SEQ ID NO: 12

Gln-His-Leu-Cys-Gly-Ser-$Xaa_4$-Leu-Val-Glu-Ala-Leu-

Tyr-Leu-Val-Cys-Gly-Glu-Arg-Gly-Phe-Phe-Tyr-$Xaa_1$-

Pro-Glu-Thr

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside.

The amino-acid sequence of a variant B chain modified by glycosylation at residue B27, Cyclohexanylalanine (Cha) at residue B24, and extended by two residues is provided in SEQ ID NO: 13.

SEQ ID NO: 13

Phe-Val-Glu-Gln-His-Leu-Cys-Gly-Ser-$Xaa_4$-Leu-Val-

Glu-Ala-Leu-Tyr-Leu-Val-Cys-Gly-Glu-Arg-Gly-Cha-

Phe-Tyr-$Xaa_1$-Lys-Pro-Thr-$Xaa_2$-$Xaa_3$

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside; and where $Xaa_2$-$Xaa_3$ is a two-residue extension of the B chain containing at least one acidic residue (Glu or Asp).

The amino-acid sequence of a variant B chain modified by glycosylation at residue B27, Cyclohexanylalanine (Cha) at position B24, and an Aspartic acid at position B28 is provided in SEQ ID NO: 14.

SEQ ID NO: 14

Phe-Val-Glu-Gln-His-Leu-Cys-Gly-Ser-$Xaa_4$-Leu-Val-

Glu-Ala-Leu-Tyr-Leu-Val-Cys-Gly-Glu-Arg-Gly-Cha-

Phe-Tyr-$Xaa_1$-Asp-$Xaa_2$-Thr

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside; and where $Xaa_2$ is Pro, Ala or a basic residue selected from the group Lys, norleucine, Orn, diaminobutyric acid or diaminopropionic acid.

The amino-acid sequence of a variant B chain modified by glycosylation at residue B27, Cyclohexanylalanine (Cha) at position B24, Glutamic acid at B29, and an N-terminal deletion of residues B1-B3 is provided in SEQ ID NO: 15.

SEQ ID NO: 15

Gln-His-Leu-Cys-Gly-Ser-$Xaa_4$-Leu-Val-Glu-Ala-Leu-

Tyr-Leu-Val-Cys-Gly-Glu-Arg-Gly-Cha-Phe-Tyr-$Xaa_1$-

Pro-Glu-Thr

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside.

The amino-acid sequence of a variant B chain modified by glycosylation at residue B27, a non-standard derivative of Phenylalanine at residue B24, and extended by two residues is provided in SEQ ID NO: 16.

SEQ ID NO: 16

Phe-Val-Glu-Gln-His-Leu-Cys-Gly-Ser-$Xaa_4$-Leu-Val-

Glu-Ala-Leu-Tyr-Leu-Val-Cys-Gly-Glu-Arg-Gly-$Xaa_4$-

Phe-Tyr-$Xaa_1$-Lys-Pro-Thr-$Xaa_2$-$Xaa_3$

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside; where $Xaa_2$-$Xaa_3$ is a two-residue extension of the B chain containing at least one acidic residue (Glu or Asp); and where $Xaa_3$ is 2-$CH_3$-Phe, 3-$CH_3$-Phe, 4-$CH_3$-Phe, or a halogenated derivative of Phe selected from the group consisting of pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant B chain modified by glycosylation at residue B27, a halogen derivative of Phenylalanine at residue B24, and an Aspartic acid at position B28 is provided in SEQ ID NO: 17.

SEQ ID NO: 17

Phe-Val-Glu-Gln-His-Leu-Cys-Gly-Ser-$Xaa_4$-Leu-Val-

Glu-Ala-Leu-Tyr-Leu-Val-Cys-Gly-Glu-Arg-Gly-$Xaa_3$-

Phe-Tyr-$Xaa_1$-Asp-$Xaa_2$-Thr

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside; and where $Xaa_2$ is Pro, Ala or a basic residue selected from the group Lys, norleucine, Orn, diaminobutyric acid or diaminopropionic acid; and where $Xaa_3$ is a halogenated derivative of Phe selected from the group consisting of 2-$CH_3$-Phe, 3-$CH_3$-Phe, 4-$CH_3$-Phe, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant B chain modified by glycosylation at residue B27, a non-standard derivative of Phenylalanine at residue B24, Glutamic acid at B29, and an N-terminal deletion of residues B1-B3 is provided in SEQ ID NO: 18.

SEQ ID NO: 18
Gln-His-Leu-Cys-Gly-Ser-$Xaa_4$-Leu-Val-Glu-Ala-Leu-

Tyr-Leu-Val-Cys-Gly-Glu-Arg-Gly-Phe-$Xaa_2$-Tyr- $Xaa_1$-Pro-Glu-Thr

Where $Xaa_1$ is an $O^\beta$-$Ser^{B27}$-linked monosaccaride pyranoside or $O^\beta$-$Thr^{B27}$-linked monosaccaride pyranoside selected from a group consisting of α-D-mannopyranoside, α-D-glucopyranoside, or N-acetyl-β-D-galactopyranoside; and where $Xaa_2$ is 2-$CH_3$-Phe, 3-$CH_3$-Phe, 4-$CH_3$-Phe, or a halogenated derivative of Phe selected from the group consisting of pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant B chain modified by glycosylation at residue B27 and containing an acidic residue at B10, a non-standard derivative of Phenylalanine at residue B24, and substitutions at positions B28 and/or B29 known in the art to confer rapid action is provided in SEQ ID NO: 19.

SEQ ID NO: 19
Phe-Val-Glu-Gln-$Xaa_3$-Leu-Cys-Gly-Ser-$Xaa_4$-Leu-Val-

Glu-Ala-Leu-Tyr-Leu-Val-Cys-Gly-Glu-Arg-Gly-$Xaa_2$-

Phe-Tyr-$Xaa_1$-$Xaa_4$-$Xaa_5$-Thr

Where $Xaa_1$ is an $O^\beta$-$Ser^{B27}$-linked monosaccaride pyranoside or $O^\beta$-$Thr^{B27}$-linked monosaccaride pyranoside selected from a group consisting of α-D-mannopyranoside, α-D-glucopyranoside, or N-acetyl-β-D-galactopyranoside; and where $Xaa_2$ is a halogenated derivative of Phe selected from the group consisting of 2-$CH_3$-Phe, 3-$CH_3$-Phe, 4-$CH_3$-Phe, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe; where $Xaa_3$ is Asp or Glu; and where $Xaa_4$-$Xaa_5$ is Lys-Pro, Lys-Ala, Asp-Pro, Asp-Lys, Asp-Orn, Asp-diaminobutyric acid, Asp-diaminopropionic acid, or Asp-Norleucine.

The amino-acid sequence of a variant B chain modified by glycosylation at residue B30 and containing an acidic one-residue extension of the B-chain and substitutions at positions B28 and/or B29 known in the art to confer rapid action is provided in SEQ ID NO: 20.

SEQ ID NO: 20
Phe-Val-Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-$Xaa_3$-$Xaa_4$-$Xaa_1$-$Xaa_2$

Where $Xaa_1$ is an $O^\beta$-$Ser^{B30}$-linked monosaccaride pyranoside or $O^\beta$-$Thr^{B30}$-linked monosaccaride pyranoside selected from a group consisting of α-D-mannopyranoside, α-D-glucopyranoside, or N-acetyl-β-D-galactopyranoside; and where $Xaa_2$ is Glu or Asp; and where $Xaa_3$-$Xaa_4$ is Lys-Pro, Lys-Ala, Asp-Pro, Asp-Lys, Asp-Orn, Asp-diaminobutyric acid, Asp-diaminopropionic acid, or Asp-Norleucine.

The amino-acid sequence of a variant B chain modified by glycosylation at residue B30, a two-residue extension of the B-chain and substitutions at positions B28 and/or B29 known in the art to confer rapid action is provided in SEQ ID NO: 21.

SEQ ID NO: 21
Phe-Val-Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-$Xaa_4$-$Xaa_5$-$Xaa_1$-$Xaa_2$-$Xaa_3$

Where $Xaa_1$ is an $O^\beta$-$Ser^{B30}$-linked monosaccaride pyranoside or $O^\beta$-$Thr^{B30}$-linked monosaccaride pyranoside selected from a group consisting of α-D-mannopyranoside, α-D-glucopyranoside, or N-acetyl-β-D-galactopyranoside; where $Xaa_2$-$Xaa_3$ is a two-residue extension of the B chain containing at least one acidic residue (Glu or Asp); and where $Xaa_4$-$Xaa_5$ is Lys-Pro, Lys-Ala, Asp-Pro, Asp-Lys, Asp-Orn, Asp-diaminobutyric acid, Asp-diaminopropionic acid, or Asp-Norleucine.

The amino-acid sequence of a variant B chain modified by glycosylation at residue B30, a nonstandard amino-acid residue at B24, a two-residue extension of the B-chain and substitutions at positions B28 and/or B29 known in the art to confer rapid action is provided in SEQ ID NO: 22.

SEQ ID NO: 22
Phe-Val-Glu-Gln-His-Leu-Cys-Gly-Ser-His-Leu-Val-

Glu-Ala-Leu-Tyr-Leu-Val-Cys-Gly-Glu-Arg-Gly- $Xaa_5$-Phe-Tyr-Thr-$Xaa_3$-$Xaa_4$-$Xaa_1$-$Xaa_2$

Where $Xaa_1$ is an $O^\beta$-$Ser^{B30}$-linked monosaccaride pyranoside or $O^\beta$-$Thr^{B30}$-linked monosaccaride pyranoside selected from a group consisting of α-D-mannopyranoside, α-D-glucopyranoside, or N-acetyl-β-D-galactopyranoside; where $Xaa_2$ is a one-residue extension of the B chain containing Glu or Asp; where $Xaa_4$-$Xaa_5$ is Lys-Pro, Lys-Ala, Asp-Pro, Asp-Lys, Asp-Orn, Asp-diaminobutyric acid, Asp-diaminopropionic acid, or Asp-Norleucine; and where $Xaa_5$ is a non-standard amino acid selected from the group consisting of 2-$CH_3$-Phe, 3-$CH_3$-Phe, 4-$CH_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant B chain modified by glycosylation at residue B30, a nonstandard amino-acid residue at B24, a two-residue extension of the B-chain and substitutions at positions B28 and/or B29 known in the art to confer rapid action is provided in SEQ ID NO: 23.

SEQ ID NO: 23
Phe-Val-Glu-Gln-His-Leu-Cys-Gly-Ser-His-Leu-Val-

Glu-Ala-Leu-Tyr-Leu-Val-Cys-Gly-Glu-Arg-Gly-$Xaa_6$-

Phe-Tyr-Thr-$Xaa_4$-$Xaa_5$-$Xaa_1$-$Xaa_2$-$Xaa_3$

Where $Xaa_1$ is an $O^\beta$-$Ser^{B30}$-linked monosaccaride pyranoside or $O^\beta$-$Thr^{B30}$-linked monosaccaride pyranoside selected from a group consisting of α-D-mannopyranoside, α-D-glucopyranoside, or N-acetyl-β-D-galactopyranoside; where Xaa$_2$-Xaa$_3$ is a two-residue extension of the B chain containing at least one acidic residue (Glu or Asp); where Xaa$_4$-Xaa$_5$ is Lys-Pro, Lys-Ala, Asp-Pro, Asp-Lys, Asp-Orn, Asp-diaminobutyric acid, Asp-diaminopropionic acid, or Asp-Norleucine; and where Xaa$_6$ is a non-standard amino acid selected from the group consisting of 2-CH$_3$-Phe, 3-CH$_3$-Phe, 4-CH$_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant B chain modified by glycosylation at residue B30, an acidic residue at position B10, a two-residue extension of the B-chain and substitutions at positions B28 and/or B29 known in the art to confer rapid action is provided in SEQ ID NO: 24.

SEQ ID NO: 24

Phe-Val-Glu-Gln-His-Leu-Cys-Gly-Ser-$Xaa_6$-Leu-Val-

Glu-Ala-Leu-Tyr-Leu-Val-Cys-Gly-Glu-Arg-Gly-Phe-

Phe-Tyr-Thr-$Xaa_4$-$Xaa_5$-$Xaa_1$-$Xaa_2$-$Xaa_3$

Where $Xaa_1$ is an $O^β$-$Ser^{B30}$-linked monosaccaride pyranoside or $O^β$-$Thr^{B30}$-linked monosaccaride pyranoside selected from a group consisting of α-D-mannopyranoside, α-D-glucopyranoside, or N-acetyl-β-D-galactopyranoside; where $Xaa_2$-$Xaa_3$ is a two-residue extension of the B chain containing at least one acidic residue (Glu or Asp); where $Xaa_4$-$Xaa_5$ is Lys-Pro, Lys-Ala, Asp-Pro, Asp-Lys, Asp-Orn, Asp-diaminobutyric acid, Asp-diaminopropionic acid, or Asp-Norleucine; and where $Xaa_6$ is Asp or Glu.

The amino-acid sequence of a variant B chain modified by glycosylation at residue B30, a nonstandard amino-acid residue at B24, an acidic residue at B10, a two-residue extension of the B-chain and substitutions at positions B28 and/or B29 known in the art to confer rapid action is provided in SEQ ID NO: 25.

SEQ ID NO: 25

Phe-Val-Glu-Gln-His-Leu-Cys-Gly-Ser-$Xaa_7$-Leu-Val-

Glu-Ala-Leu-Tyr-Leu-Val-Cys-Gly-Glu-Arg-Gly-$Xaa_6$-

Phe-Tyr-Thr-$Xaa_4$-$Xaa_5$-$Xaa_1$-$Xaa_2$-$Xaa_3$

Where $Xaa_1$ is an $O^β$-$Ser^{B30}$-linked monosaccaride pyranoside or $O^β$-$Thr^{B30}$-linked monosaccaride pyranoside selected from a group consisting of α-D-mannopyranoside, α-D-glucopyranoside, or N-acetyl-β-D-galactopyranoside; where $Xaa_2$-$Xaa_3$ is a two-residue extension of the B chain containing at least one acidic residue (Glu or Asp); where $Xaa_4$-$Xaa_5$ is Lys-Pro, Lys-Ala, Asp-Pro, Asp-Lys, Asp-Orn, Asp-diaminobutyric acid, Asp-diaminopropionic acid, or Asp-Norleucine; where $Xaa_6$ is a non-standard amino acid selected from the group consisting of 2-$CH_3$-Phe, 3-$CH_3$-Phe, 4-$CH_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe; and where $Xaa_6$ is Asp or Glu.

The amino-acid sequence of a variant B chain modified by glycosylation at residue B27, a one-residue basic extension of the B-chain and substitutions at positions B29 uncleavable by trypsin is provided in SEQ ID NO: 26.

SEQ ID NO: 26

Phe-Val-Glu-Gln-His-Leu-Cys-Gly-Ser-His-Leu-Val-

-continued

Glu-Ala-Leu-Tyr-Leu-Val-Cys-Gly-Glu-Arg-Gly-Phe-

Phe-Tyr-$Xaa_1$-Pro-$Xaa_2$-Thr

Where $Xaa_1$ is an $O^β$-$Ser^{B27}$-linked monosaccaride pyranoside or $O^β$-$Thr^{B27}$-linked monosaccaride pyranoside selected from a group consisting of α-D-mannopyranoside, α-D-glucopyranoside, or N-acetyl-β-D-galactopyranoside; where $Xaa_2$ is Alanine, Norleucine, Ornithine, diaminobutyric acid or diaminopropionic acid.

The amino-acid sequence of a variant B chain modified by glycosylation at residue B27, a one-residue basic extension of the B-chain, substitutions at positions B29 uncleavable by trypsin, and amidation of $Thr^{B30}$ is provided in SEQ ID NO: 27.

SEQ ID NO: 27

Phe-Val-Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-$Xaa_1$-Pro-$Xaa_2$-Thr-amide

Where $Xaa_1$ is an $O^β$-$Ser^{B27}$-linked monosaccaride pyranoside or $O^β$-$Thr^{B27}$-linked monosaccaride pyranoside selected from a group consisting of α-D-mannopyranoside, α-D-glucopyranoside, or N-acetyl-β-D-galactopyranoside; where $Xaa_2$ is Alanine, Norleucine, Ornithine, diaminobutyric acid or diaminopropionic acid.

The amino-acid sequence of a variant B chain modified by glycosylation at residue B27, a one-residue basic extension of the B chain, substitutions at positions B29 uncleavable by trypsin, and a one-residue basic extension of the B chain is provided in SEQ ID NO: 28.

SEQ ID NO: 28

Phe-Val-Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-$Xaa_1$-Pro-$Xaa_2$-Thr-$Xaa_3$

Where $Xaa_1$ is an $O^β$-$Ser^{B27}$-linked monosaccaride pyranoside or $O^β$-$Thr^{B27}$-linked monosaccaride pyranoside selected from a group consisting of α-D-mannopyranoside, α-D-glucopyranoside, or N-acetyl-β-D-galactopyranoside; $Xaa_2$ is Alanine, Norleucine, Ornithine, diaminobutyric acid or diaminopropionic acid; and where $Xaa_2$ is Ornithine, diaminobutyric acid or diaminopropionic acid.

The amino-acid sequence of a variant B chain modified by glycosylation at residue B27, a one-residue basic extension of the B chain, substitutions at positions B29 uncleavable by trypsin, and a one-residue basic extension of the B chain with C-terminal amide is provided in SEQ ID NO: 29.

SEQ ID NO: 29

Phe-Val-Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-$Xaa_1$-Pro-$Xaa_2$-Thr-$Xaa_3$-amide

Where $Xaa_1$ is an $O^β$-$Ser^{B27}$-linked monosaccaride pyranoside or $O^β$-$Thr^{B27}$-linked monosaccaride pyranoside selected from a group consisting of α-D-mannopyranoside, α-D-glucopyranoside, or N-acetyl-β-D-galactopyranoside; $Xaa_2$ is Alanine, Norleucine, Ornithine, diaminobutyric acid or diaminopropionic acid; and where Xaa$_2$ is Ornithine, diaminobutyric acid or diaminopropionic acid.

The amino-acid sequence of a variant B chain modified by glycosylation at residue B27, a non-standard substitution at position B24, a one-residue basic extension of the B-chain, substitutions at positions B29 uncleavable by trypsin is provided in SEQ ID NO: 30.

SEQ ID NO: 30

Phe-Val-Glu-Gln-His-Leu-Cys-Gly-Ser-His-Leu-Val-

Glu-Ala-Leu-Tyr-Leu-Val-Cys-Gly-Glu-Arg-Gly-$Xaa_3$-

Phe-Tyr-$Xaa_1$-Pro-$Xaa_2$-Thr

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside; where $Xaa_2$ is Alanine, Norleucine, Ornithine, diaminobutyric acid or diaminopropionic acid; and where $Xaa_3$ is a non-standard amino acid selected from the group consisting of 2-$CH_3$-Phe, 3-$CH_3$-Phe, 4-$CH_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant B chain modified by glycosylation at residue B30, a one-residue extension of the B-chain, and substitutions at positions B29 uncleavable by trypsin is provided in SEQ ID NO: 31.

SEQ ID NO: 31

Phe-Val-Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-$Xaa_2$-$Xaa_1$-$Xaa_3$

Where $Xaa_1$ is an $O^{\beta}$-$Ser^{B30}$-linked monosaccaride pyranoside or $O^{\beta}$-$Thr^{B30}$-linked monosaccaride pyranoside selected from a group consisting of α-D-mannopyranoside, α-D-glucopyranoside, or N-acetyl-β-D-galactopyranoside; where $Xaa_2$ and Xaa3 are selected from the group consisting of Alanine, Norleucine, Ornithine, diaminobutyric acid or diaminopropionic acid.

The amino-acid sequence of a variant B chain modified by glycosylation at residue B30, a one-residue extension of the B-chain with C-terminal amide, and substitutions at positions B29 uncleavable by trypsin is provided in SEQ ID NO: 32.

SEQ ID NO: 32

Phe-Val-Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-$Xaa_2$-$Xaa_1$-$Xaa_3$-amide

Where $Xaa_1$ is an $O^{\beta}$-$Ser^{B30}$-linked monosaccaride pyranoside or $O^{\beta}$-$Thr^{B30}$-linked monosaccaride pyranoside selected from a group consisting of α-D-mannopyranoside, α-D-glucopyranoside, or N-acetyl-β-D-galactopyranoside; where $Xaa_2$ and Xaa3 are selected from the group consisting of Alanine, Norleucine, Ornithine, diaminobutyric acid or diaminopropionic acid.

The amino-acid sequence of a variant $Gln^{B13}$-containing B chain further modified by glycosylation at residue B27, a one-residue basic extension of the B-chain and substitutions at positions B29 uncleavable by trypsin is provided in SEQ ID NO: 33.

SEQ ID NO: 33

Phe-Val-Glu-Gln-His-Leu-Cys-Gly-Ser-His-Leu-Val-

Gln-Ala-Leu-Tyr-Leu-Val-Cys-Gly-Glu-Arg-Gly-Phe-

Phe-Tyr-$Xaa_1$-Pro-$Xaa_2$-Thr

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside; where $Xaa_2$ is Alanine, Norleucine, Ornithine, diaminobutyric acid or diaminopropionic acid.

The amino-acid sequence of a variant $Gln^{B13}$-containing B chain further modified by glycosylation at residue B27, a one-residue basic extension of the B-chain, substitutions at positions B29 uncleavable by trypsin, and amidation of $Thr^{B30}$ is provided in SEQ ID NO: 34.

SEQ ID NO: 34

Phe-Val-Glu-Gln-His-Leu-Cys-Gly-Ser-His-Leu-Val-

Gln-Ala-Leu-Tyr-Leu-Val-Cys-Gly-Glu-Arg-Gly-Phe-

Phe-Tyr-$Xaa_1$-Pro-$Xaa_2$-Thr-amide

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside; where $Xaa_2$ is Alanine, Norleucine, Ornithine, diaminobutyric acid or diaminopropionic acid.

The amino-acid sequence of a variant $Gln^{B13}$-containing B chain further modified by glycosylation at residue B27, a one-residue basic extension of the B chain, substitutions at positions B29 uncleavable by trypsin, and a one-residue basic extension of the B chain is provided in SEQ ID NO: 35.

SEQ ID NO: 35

Phe-Val-Glu-Gln-His-Leu-Cys-Gly-Ser-His-Leu-Val-

Gln-Ala-Leu-Tyr-Leu-Val-Cys-Gly-Glu-Arg-Gly-Phe-

Phe-Tyr-$Xaa_1$-Pro-$Xaa_2$-Thr-$Xaa_3$

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside; $Xaa_2$ is Alanine, Norleucine, Ornithine, diaminobutyric acid or diaminopropionic acid; and where $Xaa_2$ is Ornithine, diaminobutyric acid or diaminopropionic acid.

The amino-acid sequence of a variant $Gln^{B13}$-containing B chain further modified by glycosylation at residue B27, a one-residue basic extension of the B chain, substitutions at positions B29 uncleavable by trypsin, and a one-residue basic extension of the B chain with C-terminal amide is provided in SEQ ID NO: 36.

SEQ ID NO: 36

Phe-Val-Glu-Gln-His-Leu-Cys-Gly-Ser-His-Leu-Val-

Gln-Ala-Leu-Tyr-Leu-Val-Cys-Gly-Glu-Arg-Gly-Phe-

Phe-Tyr-$Xaa_1$-Pro-$Xaa_2$-Thr-$Xaa_3$-amide

Where $Xaa_1$ is an $O^{\beta}$-$Ser^{B27}$-linked monosaccaride pyranoside or $O^{\beta}$-$Thr^{B27}$-linked monosaccaride pyranoside selected from a group consisting of α-D-mannopyranoside, α-D-glucopyranoside, or N-acetyl-β-D-galactopyranoside; Xaa$_2$ is Alanine, Norleucine, Ornithine, diaminobutyric acid or diaminopropionic acid; and where Xaa$_2$ is Ornithine, diaminobutyric acid or diaminopropionic acid.

The amino-acid sequence of a variant Gln$^{B13}$-containing B chain further modified by glycosylation at residue B27, a non-standard substitution at position B24, a one-residue basic extension of the B-chain, substitutions at positions B29 uncleavable by trypsin is provided in SEQ ID NO: 37.

SEQ ID NO: 37
Phe-Val-Glu-Gln-His-Leu-Cys-Gly-Ser-His-Leu-Val-

Gln-Ala-Leu-Tyr-Leu-Val-Cys-Gly-Glu-Arg-Gly-

Xaa$_3$-Phe-Tyr-Xaa$_1$-Pro-Xaa$_2$-Thr

Where Xaa$_1$ is an O$^β$-Ser$^{B27}$-linked monosaccharide pyranoside or O$^β$-Thr$^{B27}$-linked monosaccharide pyranoside selected from a group consisting of α-D-mannopyranoside, α-D-glucopyranoside, or N-acetyl-β-D-galactopyranoside; where Xaa$_2$ is Alanine, Norleucine, Ornithine, diaminobutyric acid or diaminopropionic acid; and where Xaa$_3$ is a non-standard amino acid selected from the group consisting of 2-CH$_3$-Phe, 3-CH$_3$-Phe, 4-CH$_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant Gln$^{B13}$-containing B chain further modified by glycosylation at residue B30, a one-residue extension of the B-chain, and substitutions at positions B29 uncleavable by trypsin is provided in SEQ ID NO: 38.

SEQ ID NO: 38
Phe-Val-Glu-Gln-His-Leu-Cys-Gly-Ser-His-Leu-Val-

Gln-Ala-Leu-Tyr-Leu-Val-Cys-Gly-Glu-Arg-Gly-Phe-

Phe-Tyr-Thr-Pro-Xaa$_2$-Xaa$_1$-Xaa$_3$

Where Xaa$_1$ is an O$^β$-Ser$^{B30}$-linked monosaccharide pyranoside or O$^β$-Thr$^{B30}$-linked monosaccharide pyranoside selected from a group consisting of α-D-mannopyranoside, α-D-glucopyranoside, or N-acetyl-β-D-galactopyranoside; where Xaa$_2$ and Xaa3 are selected from the group consisting of Alanine, Norleucine, Ornithine, diaminobutyric acid or diaminopropionic acid.

The amino-acid sequence of a variant Gln$^{B13}$-containing B chain further modified by glycosylation at residue B30, a one-residue extension of the B-chain with C-terminal amide, and substitutions at positions B29 uncleavable by trypsin is provided in SEQ ID NO: 39.

SEQ ID NO: 39
Phe-Val-Glu-Gln-His-Leu-Cys-Gly-Ser-His-Leu-Val-

Gln-Ala-Leu-Tyr-Leu-Val-Cys-Gly-Glu-Arg-Gly-Phe-

Phe-Tyr-Thr-Pro-Xaa$_2$-Xaa$_1$-Xaa$_3$-amide

Where Xaa$_1$ is an O$^β$-Ser$^{B30}$-linked monosaccharide pyranoside or O$^β$-Thr$^{B30}$-linked monosaccharide pyranoside selected from a group consisting of α-D-mannopyranoside, α-D-glucopyranoside, or N-acetyl-β-D-galactopyranoside; where Xaa$_2$ and Xaa3 are selected from the group consisting of Alanine, Norleucine, Ornithine, diaminobutyric acid or diaminopropionic acid.

The amino-acid sequence of a variant Gln$^{B13}$-containing B chain further modified by glycosylation at residue B30, a non-standard substitution at position B24, a one-residue extension of the B-chain, and substitutions at positions B29 uncleavable by trypsin is provided in SEQ ID NO: 40.

SEQ ID NO: 40
Phe-Val-Glu-Gln-His-Leu-Cys-Gly-Ser-His-Leu-Val-

Gln-Ala-Leu-Tyr-Leu-Val-Cys-Gly-Glu-Arg-Gly-

Xaa$_4$-Phe-Tyr-Thr-Pro-Xaa$_2$-Xaa$_1$-Xaa$_3$

Where Xaa$_1$ is an O$^β$-Ser$^{B30}$-linked monosaccharide pyranoside or O$^β$-Thr$^{B30}$-linked monosaccharide pyranoside selected from a group consisting of α-D-mannopyranoside, α-D-glucopyranoside, or N-acetyl-β-D-galactopyranoside; where Xaa$_2$ and Xaa$_3$ are each selected independently from a group consisting of Alanine, Norleucine, Ornithine, diaminobutyric acid and diaminopropionic acid; and where Xaa$_4$ is a non-standard amino acid selected from the group consisting of 2-CH$_3$-Phe, 3-CH$_3$-Phe, 4-CH$_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant Gln$^{B13}$-containing B chain further modified by glycosylation at residue B30 and by iodination of Tyr at position B26, containing a one-residue extension of the B-chain, substitutions at positions B29 uncleavable by trypsin, optionally containing a C-terminal amide and optionally containing a non-standard substitution at position B24 is provided in SEQ ID NO: 41.

SEQ ID NO: 41
Phe-Val-Glu-Gln-His-Leu-Cys-Gly-Ser-His-Leu-Val-

Gln-Ala-Leu-Tyr-Leu-Val-Cys-Gly-Glu-Arg-Gly-

Xaa$_5$-Phe-Xaa$_2$-Thr-Pro-Xaa$_3$-Xaa$_1$-Xaa$_4$-Xaa$_6$

Where Xaa$_1$ is an O$^β$-Ser$^{B30}$-linked monosaccharide pyranoside or O$^β$-Thr$^{B30}$-linked monosaccharide pyranoside selected from a group consisting of α-D-mannopyranoside, α-D-glucopyranoside, or N-acetyl-β-D-galactopyranoside; where Xaa$_2$ is 3-mono-iodo-Tyr or (3,5)-di-iodo-Tyr; where Xaa$_3$ and Xaa$_4$ are each selected independently from a group consisting of Alanine, Norleucine, Ornithine, diaminobutyric acid and diaminopropionic acid; where Xaa$_5$ is Phe or optionally a non-standard amino acid selected from the group consisting of 2-CH$_3$-Phe, 3-CH$_3$-Phe, 4-CH$_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe; and where Xaa$_6$ is an unmodified C-terminal carboxylate group or optionally C-terminal amide.

The amino-acid sequence of a variant Gln$^{B13}$-containing B chain further modified by glycosylation at residue B30, a non-standard substitution at position B24, a one-residue extension of the B-chain with C-terminal amide, and substitutions at positions B29 uncleavable by trypsin is provided in SEQ ID NO: 42.

SEQ ID NO: 42
Phe-Val-Glu-Gln-His-Leu-Cys-Gly-Ser-His-Leu-Val-

Gln-Ala-Leu-Tyr-Leu-Val-Cys-Gly-Glu-Arg-Gly-

Xaa$_4$-Phe-Tyr-Thr-Pro-Xaa$_2$-Xaa$_1$-Xaa$_3$-amide

Where Xaa$_1$ is an O$^\beta$-Ser$^{B30}$-linked monosaccharide pyranoside or O$^\beta$-Thr$^{B30}$-linked monosaccharide pyranoside selected from a group consisting of α-D-mannopyranoside, α-D-glucopyranoside, or N-acetyl-β-D-galactopyranoside; where Xaa$_2$ and Xaa$_3$ are each selected independently from a group consisting of Alanine, Norleucine, Ornithine, diaminobutyric acid and diaminopropionic acid; and where Xaa$_4$ is a non-standard amino acid selected from the group consisting of 2-CH$_3$-Phe, 3-CH$_3$-Phe, 4-CH$_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant B chain independently modified by glycosylation at both residues B27 and residue B30, containing substitutions at positions B28 and/or B29 known in the art to confer rapid action, containing a two-residue extension of the B-chain, and optionally containing a non-standard amino acid at position B24 is provided in SEQ ID NO: 43.

SEQ ID NO: 43
Phe-Val-Glu-Gln-His-Leu-Cys-Gly-Ser-His-Leu-Val-

Xaa$_5$-Ala-Leu-Tyr-Leu-Val-Cys-Gly-Glu-Arg-Gly-

Xaa$_7$-Phe-Tyr-Xaa$_1$-Xaa$_3$-Xaa$_4$-Xaa$_2$-Xaa$_5$-Xaa$_6$

Where Xaa$_1$ is an O$^\beta$-Ser$^{B30}$-linked monosaccharide pyranoside or O$^\beta$-Thr$^{B30}$-linked monosaccharide pyranoside selected from a group consisting of α-D-mannopyranoside, α-D-glucopyranoside, or N-acetyl-β-D-galactopyranoside; Xaa$_2$ is an O$^\beta$-Ser$^{B30}$-linked monosaccharide pyranoside or O$^\beta$-Thr$^{B30}$-linked monosaccharide pyranoside independently selected from a group consisting of α-D-mannopyranoside, α-D-glucopyranoside, or N-acetyl-β-D-galactopyranoside; where Xaa$_3$ and Xaa$_4$ are Lys-Pro, Lys-Ala, Asp-Pro, Asp-Lys, Asp-Ala, Asp-Norleucine, Asp-Orn, Asp-diaminobutyric acid, or Asp-dipropionic acid; where and Xaa$_5$ and Xaa$_6$ are each selected from a group consisting of Ala, Asp, and Glu such that at least one acidic residue is selected; and where Xaa$_7$ is a non-standard amino acid selected from the group consisting of Phe, 2-CH$_3$-Phe, 3-CH$_3$-Phe, 4-CH$_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant B chain independently modified by glycosylation at both residues B27 and residue B30, containing substitutions at positions B28 and/or B29 known in the art to confer rapid action, containing a one-residue extension of the B-chain, and optionally containing a non-standard amino acid at position B24 is provided in SEQ ID NO: 44.

SEQ ID NO: 44
Phe-Val-Glu-Gln-His-Leu-Cys-Gly-Ser-His-Leu-Val-

Xaa$_5$-Ala-Leu-Tyr-Leu-Val-Cys-Gly-Glu-Arg-Gly-

Xaa$_6$-Phe-Tyr-Xaa$_1$-Xaa$_3$-Xaa$_4$-Xaa$_2$-Xaa$_5$

Where Xaa$_1$ is an O$^\beta$-Ser$^{B30}$-linked monosaccharide pyranoside or O$^\beta$-Thr$^{B30}$-linked monosaccharide pyranoside selected from a group consisting of α-D-mannopyranoside, α-D-glucopyranoside, or N-acetyl-β-D-galactopyranoside; Xaa$_2$ is an O$^\beta$-Ser$^{B30}$-linked monosaccharide pyranoside or O$^\beta$-Thr$^{B30}$-linked monosaccharide pyranoside independently selected from a group consisting of α-D-mannopyranoside, α-D-glucopyranoside, or N-acetyl-β-D-galactopyranoside; where Xaa$_3$ and Xaa$_4$ are Lys-Pro, Lys-Ala, Asp-Pro, Asp-Lys, Asp-Ala, Asp-Norleucine, Asp-Orn, Asp-diaminobutyric acid, or Asp-dipropionic acid; and where Xaa$_5$ is Ala, Asp, or Glu; and where Xaa$_6$ is a non-standard amino acid selected from the group consisting of Phe, 2-CH$_3$-Phe, 3-CH$_3$-Phe, 4-CH$_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant B chain independently modified by glycosylation at both residues B27 and residue B30, containing an acidic residue at position B10, containing substitutions at positions B28 and/or B29 known in the art to confer rapid action, containing a one-residue extension of the B-chain, and optionally containing a non-standard amino acid at position B24 is provided in SEQ ID NO: 45.

SEQ ID NO: 45
Phe-Val-Glu-Gln-His-Leu-Cys-Gly-Ser-Xaa$_7$-Leu-Val-

Xaa$_5$-Ala-Leu-Tyr-Leu-Val-Cys-Gly-Glu-Arg-Gly-Xaa$_6$-

Phe-Tyr-Xaa$_1$-Xaa$_3$-Xaa$_4$-Xaa$_2$-Xaa$_5$

Where Xaa$_1$ is an O$^\beta$-Ser$^{B30}$-linked monosaccharide pyranoside or O$^\beta$-Thr$^{B30}$-linked monosaccharide pyranoside selected from a group consisting of α-D-mannopyranoside, α-D-glucopyranoside, or N-acetyl-β-D-galactopyranoside; Xaa$_2$ is an O$^\beta$-Ser$^{B30}$-linked monosaccharide pyranoside or O$^\beta$-Thr$^{B30}$-linked monosaccharide pyranoside independently selected from a group consisting of α-D-mannopyranoside, α-D-glucopyranoside, or N-acetyl-β-D-galactopyranoside; where Xaa$_3$ and Xaa$_4$ are Lys-Pro, Lys-Ala, Asp-Pro, Asp-Lys, Asp-Ala, Asp-Norleucine, Asp-Orn, Asp-diaminobutyric acid, or Asp-dipropionic acid; and where Xaa$_5$ is Ala, Asp, or Glu; where Xaa$_6$ is a non-standard amino acid selected from the group consisting of Phe, 2-CH$_3$-Phe, 3-CH$_3$-Phe, 4-CH$_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe; and where Xaa$_7$ is Glu or Asp.

The amino-acid sequence of a variant B chain independently modified by glycosylation at both residues B27 and residue B30, containing a one-residue extension of the B-chain, containing substitutions at positions B29 uncleavable by trypsin, optionally containing Glutamine at position B13, and optionally containing a non-standard amino acid at position B24 is provided in SEQ ID NO: 46.

SEQ ID NO: 46
Phe-Val-Glu-Gln-His-Leu-Cys-Gly-Ser-His-Leu-Val-

Xaa$_5$-Ala-Leu-Tyr-Leu-Val-Cys-Gly-Glu-Arg-Gly-Xaa$_5$-

Phe-Tyr-Xaa$_1$-Pro-Xaa$_3$-Xaa$_2$-Xaa$_4$

Where Xaa$_1$ is an O$^\beta$-Ser$^{B30}$-linked monosaccharide pyranoside or O$^\beta$-Thr$^{B30}$-linked monosaccharide pyranoside selected from a group consisting of α-D-mannopyranoside, α-D-glucopyranoside, or N-acetyl-β-D-galactopyranoside; where Xaa$_2$ is an O$^\beta$-Ser$^{B30}$-linked monosaccharide pyranoside or O$^\beta$-Thr$^{B30}$-linked monosaccharide pyranoside selected independently from a group consisting of α-D-mannopyranoside, α-D-glucopyranoside, or N-acetyl-β-D-galactopyranoside; where Xaa$_3$ and Xaa$_4$ are each selected independently from a group consisting of Alanine, Norleucine, Ornithine, diaminobutyric acid and diaminopropionic acid; where Xaa$_5$ is Glu or Gln; and where Xaa$_6$ is a non-standard amino acid selected from the group consisting of 2-CH$_3$-Phe, 3-CH$_3$-Phe, 4-CH$_3$-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of a variant B chain independently modified by glycosylation at both residues B27 and residue B30, containing a one-residue extension of the B-chain with C-terminal amide, containing substitutions at positions B29 uncleavable by trypsin, optionally containing Glutamine at position B13, and optionally containing a non-standard amino acid at position B24 is provided in SEQ ID NO: 47.

```
                                                SEQ ID NO: 47
Phe-Val-Glu-Gln-His-Leu-Cys-Gly-Ser-His-Leu-Val-

Xaa₅-Ala-Leu-Tyr-Leu-Val-Cys-Gly-Glu-Arg-Gly-

Xaa₅-Phe-Tyr-Xaa₁-Pro-Xaa₃-Xaa₂-Xaa₄-amide
```

Where $Xaa_1$ is an $O^\beta$-$Ser^{B30}$-linked monosaccharide pyranoside or $O^\beta$-$Thr^{B30}$-linked monosaccharide pyranoside selected from a group consisting of α-D-mannopyranoside, α-D-glucopyranoside, or N-acetyl-β-D-galactopyranoside; where $Xaa_2$ is an $O^\beta$-$Ser^{B30}$-linked monosaccharide pyranoside or $O^\beta$-$Thr^{B30}$-linked monosaccharide pyranoside selected independently from a group consisting of α-D-mannopyranoside, α-D-glucopyranoside, or N-acetyl-β-D-galactopyranoside; where $Xaa_3$ and $Xaa_4$ are each selected independently from a group consisting of Alanine, Norleucine, Ornithine, diaminobutyric acid and diaminopropionic acid; where $Xaa_5$ is Glu or Gln; and where $Xaa_6$ is a non-standard amino acid selected from the group consisting of 2-CH₃-Phe, 3-CH₃-Phe, 4-CH₃-Phe, Cyclohexanylalanine, pentafluoro-Phe, 2F-Phe, 3F-Phe, 2-Cl-Phe, 3-Cl-Phe, 4-Cl-Phe, 2-Br-Phe, 3-Br-Phe, and 4-Br-Phe.

The amino-acid sequence of the A chain of human insulin modified at position A8 to contain Glutamic acid is provided as SEQ ID NO: 48.

```
                                                SEQ ID NO: 48
Gly-Ile-Val-Glu-Gln-Cys-Cys-Glu-Ser-Ile-Cys-Ser-

Leu-Tyr-Gln-Leu-Glu-Asn-Tyr-Cys-Asn
```

The amino-acid sequence of the A chain of human insulin modified at position A8 to contain a nitrogen-containing side chain is provided as SEQ ID NO: 49.

```
                                                SEQ ID NO: 49
Gly-Ile-Val-Glu-Gln-Cys-Cys-Xaa₁-Ser-Ile-Cys-Ser-

Leu-Tyr-Gln-Leu-Glu-Asn-Tyr-Cys-Asn
```

Where $Xaa_1$ is selected from a group consisting of His, Trp, Lys, Arg, or Gln.

The amino-acid sequence of the A chain of human insulin modified at position A8 to contain a nitrogen-containing side chain and further modified at position A21 is provided as SEQ ID NO: 50.

```
                                                SEQ ID NO: 50
Gly-Ile-Val-Glu-Gln-Cys-Cys-Xaa₁-Ser-Ile-Cys-Ser-

Leu-Tyr-Gln-Leu-Glu-Asn-Tyr-Cys-Xaa₂
```

Where $Xaa_1$ is selected from a group consisting of His, Trp, Lys, Arg, or Gln; and where $Xaa_2$ is Asp, Gly or Ala.

The amino-acid sequence of the A chain of human insulin modified at positions A4 and A8 to contain Histidine and optionally modified at position A21 is provided as SEQ ID NO: 45.

```
                                                SEQ ID NO: 51
Gly-Ile-Val-His-Gln-Cys-Cys-His-Ser-Ile-Cys-Ser-

Leu-Tyr-Gln-Leu-Glu-Asn-Tyr-Cys-Xaa₁
```

Where $Xaa_1$ is Gly or Ala.

The amino-acid sequence of the A chain of human insulin containing a basic N-terminal extension and optionally modified at position A8 to contain a nitrogen-containing side chain is provided as SEQ ID NO: 52.

```
                                                SEQ ID NO: 52
Xaa₁-Gly-Ile-Val-Glu-Gln-Cys-Cys-Xaa₂-Ser-Ile-

Cys-Ser-Leu-Tyr-Gln-Leu-Glu-Asn-Tyr-Cys-Asn
```

Where $Xaa_2$ is Arg, Lys, Orn, diaminobuytic acid, or diaminopropionic acid; and where $Xaa_2$ is selected from a group consisting of Thr, His, Trp, Lys, Arg, or Gln.

The amino-acid sequence of the A chain of human insulin containing a basic N-terminal extension, optionally modified at position A8 to contain a nitrogen-containing side chain, and modified at position A21 is provided as SEQ ID NO: 53.

```
                                                SEQ ID NO: 53
Xaa₁-Gly-Ile-Val-Glu-Gln-Cys-Cys-Xaa₂-Ser-Ile-

Cys-Ser-Leu-Tyr-Gln-Leu-Glu-Asn-Tyr-Cys-Xaa₃
```

Where $Xaa_2$ is Arg, Lys, Orn, diaminobuytic acid, or diaminopropionic acid; and where $Xaa_2$ is selected from a group consisting of Thr, His, Trp, Lys, Arg, or Gln; and where $Xaa_3$ is Ala or Gly.

The following synthetic peptide sequences are suitable for trypsin-mediated sem-synthesis with wild-type des-octapeptide[B23-B30]-insulin or a variant thereof containing one or more substitutions in the A- or truncated B chains.

```
                                                SEQ ID NO: 54
Gly-Phe-Phe-Tyr-Xaa₁-Pro-Xaa₂-Thr
```

Where $Xaa_1$ is an $O^\beta$-$Ser^{B27}$-linked monosaccharide pyranoside or $O^\beta$-$Thr^{B27}$-linked monosaccharide pyranoside selected from a group consisting of α-D-mannopyranoside, α-D-glucopyranoside, or N-acetyl-β-D-galactopyranoside; and where $Xaa_2$ is Norleucine, Ornithine, diaminobutytic acid, or diaminopropionic acid.

```
                                                SEQ ID NO: 55
Gly-Xaa₃-Phe-Tyr-Xaa₁-Pro-Xaa₂-Thr
```

Where $Xaa_1$ is an $O^\beta$-$Ser^{B27}$-linked monosaccharide pyranoside or $O^\beta$-$Thr^{B27}$-linked monosaccharide pyranoside selected from a group consisting of α-D-mannopyranoside, α-D-glucopyranoside, or N-acetyl-β-D-galactopyranoside; where $Xaa_2$ is Norleucine, Ornithine, diaminobutytic acid, or diaminopropionic acid; and where $Xaa_3$ is Cyclohexanylalanine, 2-CH₃-Phe, 3-CH₃-Phe, 4-CH₃-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

```
                                                SEQ ID NO: 56
Gly-Phe-Phe-Tyr-Xaa₁-Pro-Xaa₂-Thr-amide
```

Where $Xaa_1$ is an $O^\beta$-$Ser^{B27}$-linked monosaccharide pyranoside or $O^\beta$-$Thr^{B27}$-linked monosaccharide pyranoside selected from a group consisting of α-D-mannopyranoside, α-D-glucopyranoside, or N-acetyl-β-D-galactopyranoside; and where $Xaa_2$ is Norleucine, Ornithine, diaminobutytic acid, or diaminopropionic acid.

SEQ ID NO: 57
Gly-Phe-Phe-$Xaa_3$-$Xaa_1$-Pro-$Xaa_2$-Thr

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside; where $Xaa_2$ is Norleucine, Ornithine, diaminobutytic acid, or diaminopropionic acid; and where $Xaa_3$ is 3-mono-iodo-Tyr or di-iodo-(3,5)-Tyr.

SEQ ID NO: 58
Gly-Phe-Phe-Tyr-$Xaa_1$-Pro-$Xaa_2$-Thr-$Xaa_3$

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside; where $Xaa_2$ is Norleucine, Ornithine, diaminobutytic acid, or diaminopropionic acid; and where $Xaa_3$ is Ornithine, diaminobutytic acid, or diaminopropionic acid.

SEQ ID NO: 59
Gly-$Xaa_4$-Phe-Tyr-$Xaa_1$-Pro-$Xaa_2$-Thr-$Xaa_3$

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside; where $Xaa_2$ is Norleucine, Ornithine, diaminobutytic acid, or diaminopropionic acid; where $Xaa_3$ is Ornithine, diaminobutytic acid, or diaminopropionic acid; and where $Xaa_4$ is Cyclohexanylalanine, 2-$CH_3$-Phe, 3-$CH_3$-Phe, 4-$CH_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 60
Gly-Phe-Phe-Tyr-$Xaa_1$-Pro-$Xaa_2$-Thr-$Xaa_2$-amide

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside; where $Xaa_2$ is Norleucine, Ornithine, diaminobutytic acid, or diaminopropionic acid; and where $Xaa_3$ is Ornithine, diaminobutytic acid, or diaminopropionic acid.

SEQ ID NO: 61
Gly-Phe-Phe-$Xaa_4$-$Xaa_1$-Pro-$Xaa_2$-Thr-$Xaa_3$

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside; where $Xaa_2$ is Norleucine, Ornithine, diaminobutytic acid, or diaminopropionic acid; where $Xaa_3$ is Ornithine, diaminobutytic acid, or diaminopropionic acid; and where $Xaa_4$ is 3-mono-iodo-Tyr or di-iodo-(3,5)-Tyr.

SEQ ID NO: 62
Gly-Phe-Phe-Tyr-$Xaa_1$-Lys-Pro-Thr

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside.

SEQ ID NO: 63
Gly-Phe-Phe-Tyr-$Xaa_1$-Lys-Pro-Thr-Glu-Glu

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside.

SEQ ID NO: 64
Gly-$Xaa_2$-Phe-Tyr-$Xaa_1$-Lys-Pro-Thr

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside; where $Xaa_2$ is Cyclohexanylalanine, 2-$CH_3$-Phe, 3-$CH_3$-Phe, 4-$CH_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 65
Gly-$Xaa_2$-Phe-Tyr-$Xaa_1$-Lys-Pro-Thr-Glu-Glu

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside; where $Xaa_2$ is Cyclohexanylalanine, 2-$CH_3$-Phe, 3-$CH_3$-Phe, 4-$CH_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 66
Gly-$Xaa_3$-Phe-Tyr-$Xaa_1$-Asp-$Xaa_2$-Thr

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside; Xaa2 is Pro, Ala, Norleucine, Ornithine, diamonibutyric acid, or diaminipropionic acid; and where $Xaa_3$ is Phe, Cyclohexanylalanine, 2-$CH_3$-Phe, 3-$CH_3$-Phe, 4-$CH_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 67
Gly-$Xaa_4$-Phe-Tyr-$Xaa_1$-Asp-$Xaa_2$-Thr-Glu-Glu

Where $Xaa_1$ is an $O^β$-$Ser^{B27}$-linked monosaccharide pyranoside or $O^β$-$Thr^{B27}$-linked monosaccharide pyranoside selected from a group consisting of α-D-mannopyranoside, α-D-glucopyranoside, or N-acetyl-β-D-galactopyranoside; Xaa2 is Pro, Ala, Norleucine, Ornithine, diamonibutyric acid, or diaminopropionic acid; and where $Xaa_3$ is Phe, Cyclohexanylalanine, 2-$CH_3$-Phe, 3-$CH_3$-Phe, 4-$CH_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 68
Gly-Xaa$_4$-Phe-Tyr-Xaa$_1$-Lys-Pro-Thr-Xaa$_2$-Xaa$_3$

Where Xaa$_1$ is an O$^\beta$-Ser$^{B27}$-linked monosaccharide pyranoside or O$^\beta$-Thr$^{B27}$-linked monosaccharide pyranoside selected from a group consisting of α-D-mannopyranoside, α-D-glucopyranoside, or N-acetyl-β-D-galactopyranoside; Xaa2 is Pro, Ala, Norleucine, Ornithine, diamonibutyric acid, or diaminipropionic acid; where Xaa$_2$ and Xaa$_3$ are each selected from a group consisting of Ala, Asp, and Glu such that at least one bears an acidic side chain; and where Xaa$_4$ is Phe, Cyclohexanylalanine, 2-CH$_3$-Phe, 3-CH$_3$-Phe, 4-CH$_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 69
Gly-Xaa$_5$-Phe-Tyr-Xaa$_1$-Asp-Xaa$_2$-Thr-Xaa$_3$-Xaa$_4$

Where Xaa$_1$ is an O$^\beta$-Ser$^{B27}$-linked monosaccharide pyranoside or O$^\beta$-Thr$^{B27}$-linked monosaccharide pyranoside selected from a group consisting of α-D-mannopyranoside, α-D-glucopyranoside, or N-acetyl-β-D-galactopyranoside; Xaa$_2$ is Pro, Ala, Norleucine, Ornithine, diamonibutyric acid, or diaminipropionic acid; where Xaa$_3$ and Xaa$_4$ are each selected from a group consisting of Ala, Asp, and Glu such that at least one bears an acidic side chain; and where Xaa$_5$ is Phe, Cyclohexanylalanine, 2-CH$_3$-Phe, 3-CH$_3$-Phe, 4-CH$_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 70
Gly-Xaa$_4$-Phe-Tyr-Thr-Lys-Pro-Xaa$_1$-Xaa$_2$-Xaa$_3$

Where Xaa$_1$ is an O$^\beta$-Ser$^{B30}$-linked monosaccharide pyranoside or O$^\beta$-Thr$^{B30}$-linked monosaccharide pyranoside selected from a group consisting of α-D-mannopyranoside, α-D-glucopyranoside, or N-acetyl-β-D-galactopyranoside; Xaa2 is Pro, Ala, Norleucine, Ornithine, diamonibutyric acid, or diaminipropionic acid; where Xaa$_2$ and Xaa$_3$ are each selected from a group consisting of Ala, Asp, and Glu such that at least one bears an acidic side chain; and where Xaa$_4$ is Phe, Cyclohexanylalanine, 2-CH$_3$-Phe, 3-CH$_3$-Phe, 4-CH$_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 71
Gly-Xaa$_5$-Phe-Tyr-Thr-Asp-Xaa$_2$-Xaa$_1$-Xaa$_3$-Xaa$_4$

Where Xaa$_1$ is an O$^\beta$-Ser$^{B30}$-linked monosaccharide pyranoside or O$^\beta$-Thr$^{B30}$-linked monosaccharide pyranoside selected from a group consisting of α-D-mannopyranoside, α-D-glucopyranoside, or N-acetyl-β-D-galactopyranoside; Xaa2 is Pro, Ala, Norleucine, Ornithine, diamonibutyric acid, or diaminipropionic acid; where Xaa$_3$ and Xaa$_4$ are each selected from a group consisting of Ala, Asp, and Glu such that at least one bears an acidic side chain; and where Xaa$_5$ is Phe, Cyclohexanylalanine, 2-CH$_3$-Phe, 3-CH$_3$-Phe, 4-CH$_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 72
Gly-Xaa$_5$-Phe-Tyr-Xaa$_1$-Lys-Pro-Xaa$_2$-Xaa$_3$-Xaa$_4$

Where Xaa$_1$ is an O$^\beta$-Ser$^{B27}$-linked monosaccharide pyranoside or O$^\beta$-Thr$^{B27}$-linked monosaccharide pyranoside selected from a group consisting of α-D-mannopyranoside, α-D-glucopyranoside, or N-acetyl-β-D-galactopyranoside; where Xaa$_2$ is an O$^\beta$-Ser$^{B30}$-linked monosaccharide pyranoside or O$^\beta$-Thr$^{B30}$-linked monosaccharide pyranoside independently selected from a group consisting of α-D-mannopyranoside, α-D-glucopyranoside, or N-acetyl-β-D-galactopyranoside; Xaa$_3$ and Xaa$_4$ are each selected from a group consisting of Ala, Asp, and Glu such that at least one bears an acidic side chain; and where Xaa$_5$ is Phe, Cyclohexanylalanine, 2-CH$_3$-Phe, 3-CH$_3$-Phe, 4-CH$_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 73
Gly-Xaa$_5$-Phe-Tyr-Xaa$_1$-Asp-Xaa$_3$-Xaa$_2$-Xaa$_4$

Where Xaa$_1$ is an O$^\beta$-Ser$^{B27}$-linked monosaccharide pyranoside or O$^\beta$-Thr$^{B27}$-linked monosaccharide pyranoside selected from a group consisting of α-D-mannopyranoside, α-D-glucopyranoside, or N-acetyl-β-D-galactopyranoside; where Xaa$_2$ is an O$^\beta$-Ser$^{B30}$-linked monosaccharide pyranoside or O$^\beta$-Thr$^{B30}$-linked monosaccharide pyranoside independently selected from a group consisting of α-D-mannopyranoside, α-D-glucopyranoside, or N-acetyl-β-D-galactopyranoside; Xaa$_3$ is Pro, Norleucine, Orn, diaminobutyric acid, or dipropionic acid; Xaa$_4$ is Ala, Asp, and Glu; and where Xaa$_5$ is Phe, Cyclohexanylalanine, 2-CH$_3$-Phe, 3-CH$_3$-Phe, 4-CH$_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 74
Gly-Xaa$_5$-Phe-Tyr-Xaa$_1$-Lys-Asp-Pro-Xaa$_3$-Xaa$_4$

Where Xaa$_1$ is an O$^\beta$-Ser$^{B27}$-linked monosaccharide pyranoside or O$^\beta$-Thr$^{B27}$-linked monosaccharide pyranoside selected from a group consisting of α-D-mannopyranoside, α-D-glucopyranoside, or N-acetyl-β-D-galactopyranoside; where Xaa$_2$ is an O$^\beta$-Ser$^{B30}$-linked monosaccharide pyranoside or O$^\beta$-Thr$^{B30}$-linked monosaccharide pyranoside independently selected from a group consisting of α-D-mannopyranoside, α-D-glucopyranoside, or N-acetyl-β-D-galactopyranoside; Xaa$_3$ and Xaa$_4$ are each selected from a group consisting of Ala, Asp, and Glu such that at least one bears an acidic side chain; and where Xaa$_5$ is Phe, Cyclohexanylalanine, 2-CH$_3$-Phe, 3-CH$_3$-Phe, 4-CH$_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 75
Gly-Xaa$_4$-Phe-Tyr-Xaa$_1$-Lys-Pro-Xaa$_2$-Xaa$_3$

Where Xaa$_1$ is an O$^\beta$-Ser$^{B27}$-linked monosaccharide pyranoside or O$^\beta$-Thr$^{B27}$-linked monosaccharide pyranoside selected from a group consisting of α-D-mannopyranoside, α-D-glucopyranoside, or N-acetyl-β-D-galactopyranoside; where Xaa$_2$ is an O$^\beta$-Ser$^{B30}$-linked monosaccharide pyranoside or O$^\beta$-Thr$^{B30}$-linked monosaccharide pyranoside independently selected from a group consisting of α-D-mannopyranoside, α-D-glucopyranoside, or N-acetyl-β-D-galactopyranoside; Xaa$_3$ is Ala, Asp, and Glu; and where Xaa$_4$ is Phe, Cyclohexanylalanine, 2-CH$_3$-Phe, 3-CH$_3$-Phe, 4-CH$_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 76
Gly-Xaa$_5$-Phe-Tyr-Thr-Asp-Xaa$_2$-Xaa$_1$-Xaa$_3$-Xaa$_4$

Where Xaa$_1$ is an O$^\beta$-Ser$^{B30}$-linked monosaccharide pyranoside or O$^\beta$-Thr$^{B30}$-linked monosaccharide pyranoside selected from a group consisting of α-D-mannopyranoside, α-D-glucopyranoside, or N-acetyl-β-D-galactopyranoside; Xaa2 is Pro, Ala, Norleucine, Ornithine, diamonibutyric acid, or diaminipropionic acid; where Xaa$_3$ and Xaa$_4$ are each selected from a group consisting of Ala, Asp, and Glu such that at least one bears an acidic side chain; and where Xaa$_5$ is Phe, Cyclohexanylalanine, 2-CH$_3$-Phe, 3-CH$_3$-Phe, 4-CH$_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 77
Gly-Phe-Phe-Tyr-Xaa$_1$-Pro-Xaa$_3$-Xaa$_2$-Xaa$_4$

Where Xaa$_1$ is an O$^\beta$-Ser$^{B27}$-linked monosaccharide pyranoside or O$^\beta$-Thr$^{B27}$-linked monosaccharide pyranoside selected from a group consisting of α-D-mannopyranoside, α-D-glucopyranoside, or N-acetyl-β-D-galactopyranoside; where Xaa$_2$ is an O$^\beta$-Ser$^{B30}$-linked monosaccharide pyranoside or O$^\beta$-Thr$^{B30}$-linked monosaccharide pyranoside independently selected from a group consisting of α-D-mannopyranoside, α-D-glucopyranoside, or N-acetyl-β-D-galactopyranoside; where Xaa$_3$ is Norleucine, Ornithine, diaminobutytic acid, or diaminopropionic acid; and where Xaa$_4$ is Ornithine, diaminobutytic acid, or diaminopropionic acid.

SEQ ID NO: 78
Gly-Xaa$_5$-Phe-Tyr-Xaa$_1$-Pro-Xaa$_3$-Xaa$_2$-Xaa$_4$

Where Xaa$_1$ is an O$^\beta$-Ser$^{B27}$-linked monosaccharide pyranoside or O$^\beta$-Thr$^{B27}$-linked monosaccharide pyranoside selected from a group consisting of α-D-mannopyranoside, α-D-glucopyranoside, or N-acetyl-β-D-galactopyranoside; where Xaa$_2$ is an O$^\beta$-Ser$^{B30}$-linked monosaccharide pyranoside or O$^\beta$-Thr$^{B30}$-linked monosaccharide pyranoside independently selected from a group consisting of α-D-mannopyranoside, α-D-glucopyranoside, or N-acetyl-β-D-galactopyranoside; where Xaa$_3$ is Norleucine, Ornithine, diaminobutytic acid, or diaminopropionic acid; where Xaa$_4$ is Ornithine, diaminobutytic acid, or diaminopropionic acid; and where Xaa$_5$ is Cyclohexanylalanine, 2-CH$_3$-Phe, 3-CH$_3$-Phe, 4-CH$_3$-Phe, pentafluoro-Phe, 2F-Phe, 3F-Phe, 2-Cl-Phe, 3-Cl-Phe, 4-Cl-Phe, 2-Br-Phe, 3-Br-Phe, or 4-Br-Phe.

SEQ ID NO: 79
Gly-Phe-Phe-Xaa$_5$-Xaa$_1$-Pro-Xaa$_3$-Xaa$_2$-Xaa$_4$

Where Xaa$_1$ is an O$^\beta$-Ser$^{B27}$-linked monosaccharide pyranoside or O$^\beta$-Thr$^{B27}$-linked monosaccharide pyranoside selected from a group consisting of α-D-mannopyranoside, α-D-glucopyranoside, or N-acetyl-β-D-galactopyranoside; where Xaa$_2$ is an O$^\beta$-Ser$^{B30}$-linked monosaccharide pyranoside or O$^\beta$-Thr$^{B30}$-linked monosaccharide pyranoside independently selected from a group consisting of α-D-mannopyranoside, α-D-glucopyranoside, or N-acetyl-β-D-galactopyranoside; where Xaa$_3$ is Norleucine, Ornithine, diaminobutytic acid, or diaminopropionic acid; where Xaa$_4$ is Ornithine, diaminobutytic acid, or diaminopropionic acid; and where Xaa$_5$ is 3-mono-iodo-Tyr or (3,5)-di-iodo-Tyr.

Analogues of insulin containing α-D-mannopyranoside, β-D-glucopyranoside, and/or N-acetyl-β-D-galactopyranoside as O$^\beta$-linked adducts of Threonine were prepared by trypsin-mediated semi-synthesis. The protocol for semi-synthesis employed a des-octapeptide[B23-B30] fragment of human insulin or insulin analogue together with a synthetic peptide containing an N-terminal Glycine (octapeptide, nonapeptide, or decapeptide) and a monosaccharide adduct at Thr$^{B27}$ and/or Thr$^{B30}$. The des-octapeptide[B23-B30] fragment contains the three native disulfide bridges of wild-type insulin; the protocol including purification of the fragment, peptide, and product by high-performance liquid chromatography was a modification of that described (Mirmira, R. G., and Tager, H. S., 1989. J. Biol. Chem. 264: 6349-6354.) This protocol employs (i) a synthetic peptide containing a monosaccharide pyranoside adduct (SEQ ID NO: 53-65) and (ii) truncated analogue des-tripeptide[B1-B3]-des-octapeptide[B23-B30]-insulin, or in the case of [HisA4, His$^{48}$, Gly$^{A21}$]-insulin analogues, [HisA4, His$^{48}$, Gly$^{A21}$]-des-tripeptide[B1-B3]-des-octapeptide[B23-B30]-insulin, or in the case of Gln$^{B13}$-insulin analogues, Gln$^{B13}$-des-tripeptide[B1-B3]-des-octapeptide[B23-B30]-insulin, or in the case of His$^{A8}$-insulin analogues, His$^{A8}$-des-tripeptide[B1-B3]-des-octapeptide[B23-B30]-insulin. With respect to non-standard synthetic peptide sequences containing an N-terminal Glycine, sequence design exploited the inability of trypsin does not cleave after Orn, Norleucine, diaminobutyric acid, or diaminopropinic acid and further exploited the fact that trypsin cleaves Lys-Pro steps inefficiently (as in KP-insulin and KP-insulin analogues; residues B28-B29) in contrast to the efficient cleavage of Pro-Lys-Xaa steps (as in wild-type human, pork, and beef insulin; residues B28-B30). Synthetic peptides were prepared by solid-phase peptide synthesis using 9-fluoren-9-yl-methoxy-carbonyl (F-moc) protected precursors. Fmoc-protected precursors of Thr adducts contained appropriate protecting groups on hydroxyl groups of the monosaccharide pyranoside.

In brief, des-octapeptide (15 mg) and octapeptide (15 mg) were dissolved in a mixture of dimethylacetamide/1,4-butandiol/0.2 M Tris acetate (pH 8) containing 10 mM calcium acetate and 1 mM ethylene diamine tetra-acetic acid (EDTA) (35:35:30, v/v, 0.4 mL). The final pH was adjusted to 7.0 with 10 μL of N-methylmorpholine. The solution was cooled to 12° C., and 1.5 mg of TPCK-trypsin was added and incubated for 2 days at 12° C. An additional 1.5 mg of trypsin was added after 24 hr. The reaction was acidified with 0.1% trifluoroacetic acid and purified by preparative reverse-phase HPLC (C4). Mass spectrometry using matrix-assisted laser desorption/ionization time-of-flight (MALDI-TOF; Applied Biosystems, Foster City, Calif.) in each case gave expected values (not shown). The general protocol for solid-phase synthesis is as described (Merrifield et al., 1982. Biochemistry 21: 5020-5031). 9-fluoren-9-yl-methoxy-carbonyl (F-moc)-protected phenylalanine analogues were purchased from Chem-Impex International (Wood Dale, Ill.).

The above protocol was employed to prepare analogues of human insulin containing Lysine at position B28, Proline at position B29, and Threonine at position B30 (derivatives of KP-insulin). The protocol was also employed to prepare B-chain extended analogues containing the "KP" substitutions, Glu$^{B31}$ and Glu$^{B31}$, and at B30 either Thr, α-D-mannopyranoside-O$^\beta$-Thr, or N-acetyl-β-D-galactopyranoside-O$^\beta$-Thr. The above protocol was further employed to prepare analogues of human insulin containing Ornithine at position B29 and as a B31 extension; the intervening residue at B30 was either Thr, α-D-mannopyranoside-O$^\beta$-Thr, or N-acetyl-β-D-galactopyranoside-O$^β$-Thr. An analogue was also prepared containing α-D-mannopyranoside-O$^β$-Thr$^{B27}$ and β-D-glucopyranoside-O$^β$-Thr$^{B30}$ in the context of an extended B-chain containing Glu$^{B31}$ and Glu$^{B32}$ as an acidic tag. The method of preparation of these analogues exploits non-standard amino-acid substitutions at position 29 to eliminate the tryptic site ordinarily present within the C-terminal octapeptide of the B chain (i.e., between Lys$^{B29}$ and Thr$^{B30}$) while maintaining a Proline at position 28. Pro$^{B28}$ contributes to the stability of the dimer interface within the insulin hexamer, and so this method of preparation provides near-isosteric models of wild-type insulin in which other modifications may conveniently be incorporated without the need for cumbersome side-chain protection.

Circular dichroism (CD) spectra were obtained at 4° C. and/or 25° C. using an Aviv spectropolarimeter (Weiss et al., *Biochemistry* 39: 15429-15440). Samples contained ca. 25 μM DKP-insulin or analogues in 50 mM potassium phosphate (pH 7.4); samples were diluted to 5 μM for guanidine-induced denaturation studies at 25° C. To extract free energies of unfolding, denaturation transitions were fitted by non-linear least squares to a two-state model as described by Sosnick et al., *Methods Enzymol.* 317: 393-409. In brief, CD data θ(x), where x indicates the concentration of denaturant, were fitted by a nonlinear least-squares program according to $$\theta(x) = \frac{\theta_A + \theta_B e^{(-\Delta G^o_{H_2O} - mx)/RT}}{1 + e^{(-\Delta G^o_{H_2O} - mx)/RT}}$$

where x is the concentration of guanidine and where $\theta_A$ and $\theta_B$ are baseline values in the native and unfolded states. Baselines were approximated by pre- and post-transition lines. The m values obtained in fitting the variant unfolding transitions are lower than the m value obtained in fitting the wild-type unfolding curve. To test whether this difference and apparent change in $\Delta G_u$ result from an inability to measure the CD signal from the fully unfolded state, simulations were performed in which the data were extrapolated to plateau CD values at higher concentrations of guanidine; essentially identical estimates of $\Delta G_u$ and m were obtained.

Figure 6:
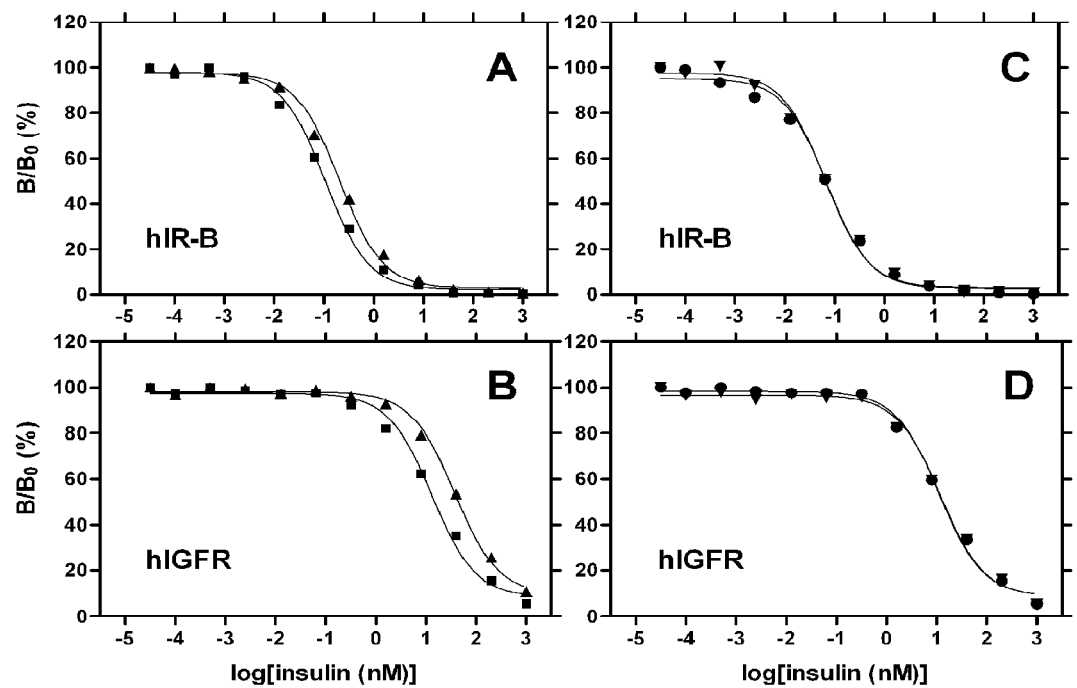
FIG. 6 is a graph showing the results of receptor-binding studies of insulin analogues. (A and B) Studies of α-D-mannopyranoside-$O^β$-$Thr^{B27}$-KP-insulin versus KP-insulin by competitive displacement of (A) $^{125}I$-$Tyr^{A14}$-labeled human insulin bound to isoform B of the human insulin receptor and (B) $^{125}I$-Tyr31-labeled IGF-I bound to the Type I IGF Receptor (IGF-1R). Symbols: (■) KP-insulin and (▲) α-D-mannopyranoside-$O^β$-$Thr^{B27}$-KP-insulin. (C and D) Studies of N-acetyl-β-D-galactopyranoside-$O^β$-$Thr^{B27}$-$Orn^{B29}$-insulin versus $Orn^{B29}$-insulin by competitive displacement of (A) $^{125}I$-$Tyr^{A14}$-labeled human insulin IR-B and (B) $^{125}I$-Tyr31-labeled IGF-I bound to IGF-1R. Symbols: (■) KP-insulin and (▲) α-D-mannopyranoside-$O^β$-$Thr^{B27}$-KP-insulin. (B) Relative activities for the Type I IGF receptor (IGF-1R) are determined by competitive binding assay in which receptor-bound $^{125}I$-labeled IGF-I is displaced by increasing concentrations of human insulin (■) or its analogues: Symbols: N-acetyl-β-D-galactopyranoside-$O^β$-$Thr^{B27}$-$Orn^{B29}$-insulin (▼) and $Orn^{B29}$-insulin (●).

Relative activity is defined as the ratio of the hormone-receptor dissociation constants of analogue to wild-type human insulin, as measured by a competitive displacement assay using $^{125}$I-human insulin. Microtiter strip plates (Nunc Maxisorb) were incubated overnight at 4° C. with AU5 IgG (100 μl/well of 40 mg/ml in phosphate-buffered saline). Binding data were analyzed by a two-site sequential model. Data were corrected for nonspecific binding (amount of radioactivity remaining membrane associated in the presence of 1 μM human insulin. In all assays the percentage of tracer bound in the absence of competing ligand was less than 15% to avoid ligand-depletion artifacts. Representative data are provided in FIGS. 6A and 6C; corresponding assays conducted with the Type I IGF receptor (IGF-1R) are shown in FIGS. 6B and 6D (labeled IGFR in the figure). Dissociation constants ($K_d$) were determined by fitting to a mathematic model as described by Whittaker and Whittaker (2005. *J. Biol. Chem.* 280: 20932-20936); the model employed non-linear regression with the assumption of heterologous competition (Wang, 1995, *FEBS Lett.* 360: 111-114). Results are summarized in Tables 1A, 1B, and 1C.

In each case the insulin analogues modified by a monosaccaride adduct retain a significant portion of the binding affinity of human insulin.

TABLE 1A

| | Dissociation Constant (nM) | | |
|---|---|---|---|
| Analog | hIR-A | hIR-B | hIGF-1R |
| KP-insulin | 0.047 ± 0.007 | 0.069 ± 0.010 | 8.39 ± 1.34 |
| α-D-mannopyranoside-Oβ-Thr$^{B27}$-KP-insulin | 0.091 ± 0.014 | 0.131 ± 0.020 | 23.05 ± 4.97 |
| N-acetyl-β-D-galacto-pyranoside-Oβ-Thr$^{B27}$-KP insulin | 0.055 ± 0.008 | 7.17 ± 1.20 | ND |

TABLE 1B

| | Dissociation Constant (nM) | | |
|---|---|---|---|
| Analog | hIR-A | hIR-B | hIGF-1R |
| KP insulin | 0.047 ± 0.007 | 0.069 ± 0.010 | 8.39 ± 1.34 |
| KPTEE | 0.098 ± 0.014 | 0.141 ± 0.021 | 40.87 ± 7.01 |
| α-D-mannopyran-oside-Oβ-Thr B30 KPTEE | 0.122 ± 0.017 | 0.166 ± 0.024 | 51. ± 10.76 |

TABLE 1C

| | Dissociation Constant (nM) | |
|---|---|---|
| Analog | hIR-B | hIGF-1R |
| Orn$^{B29}$-insulin | 0.041 ± 0.007 | 7.14 ± 1.17 |
| N-acetyl-β-D-galacto-pyranoside-Oβ-Thr$^{B27}$-Orn$^{B29}$-insulin | 0.032 ± 0.006 | 7.57 ± 1.26 |
| [His$^{A4}$, His$^{A8}$, Gly$^{A21}$]-insulin | 0.134 ± 0.020 | 29.04 ± 5.70 |
| α-D-mannopyranoside-Oβ-Thr$^{B30}$-[His$^{A4}$, His$^{A8}$, Gly$^{A21}$]-insulin | 0.199 ± 0.029 | 41.8 ± 0.36 |

TABLE 1D

| | Dissociation Constant (nM) | |
|---|---|---|
| Analog | hIR-B | hIGF-1R |
| KP-insulin | 0.120 ± 0.017 | 3.86 ± 0.60 |
| β-D-glucopyranoside-Oβ-Thr$^{B27}$-KP-insulin | 0.147 ± 0.022 | 6.11 ± 1.02 |
| α-D-mannopyranoside-Oβ-Thr$^{B27}$-Glucose-Thr$^{B30}$-KP-insulin | 0.515 ± 0.073 | 45.88 ± 8.95 |

Footnote to Table 1: Abbreviations, hIR-A, A isoform of the human insulin receptor; hIR-B, B isoform of the human insulin receptor; IGF-1R, human Type 1 IGF receptor; ND, not determined.
Data in Table 1D were obtained with a different preparation of receptor than was used in Tables 1A-1C, accounting for the lower apparent affinity of the control KP-insulin analog.

TABLE 2

Thermodynamic Studies of Insulin Analogues

| Analog | $\Delta G_u$ (kcal/mol) | $C_{mid}$ (M) |
|---|---|---|
| KP-insulin | 2.8 ± 0.1 | 4.7 ± 0.2 |
| β-D-glucopyranoside-Oβ-Thr$^{B27}$-KP-insulin | 3.0 ± 0.1 | 4.9 ± 0.1 |
| KPTEE | 3.1 ± 0.1 | 5.0 ± 0.1 |
| α-D-mannopyranoside-Oβ-Thr$^{B27}$-Glucose-Thr$^{B30}$-KP-insulin | 3.3 ± 0.1 | 4.8 ± 0.2 |

TABLE 2-continued

Thermodynamic Studies of Insulin Analogues

| Analog | $\Delta G_u$ (kcal/mol) | $C_{mid}$ (M) |
|---|---|---|
| α-D-mannopyranoside-O$^\beta$-Thr$^{B27}$-KP-insulin | 3.0 ± 0.1 | 4.9 ± 0.1 |

Footnote to Table 2: Free energies of unfolding as inferred from application of a two-state model are designated $\Delta G_u$ (kcal/mol).
The concentration of guanidine-HCl required to unfold 50% of the protein molecules in solution is designated $C_{mid}$.

Figure 7A:
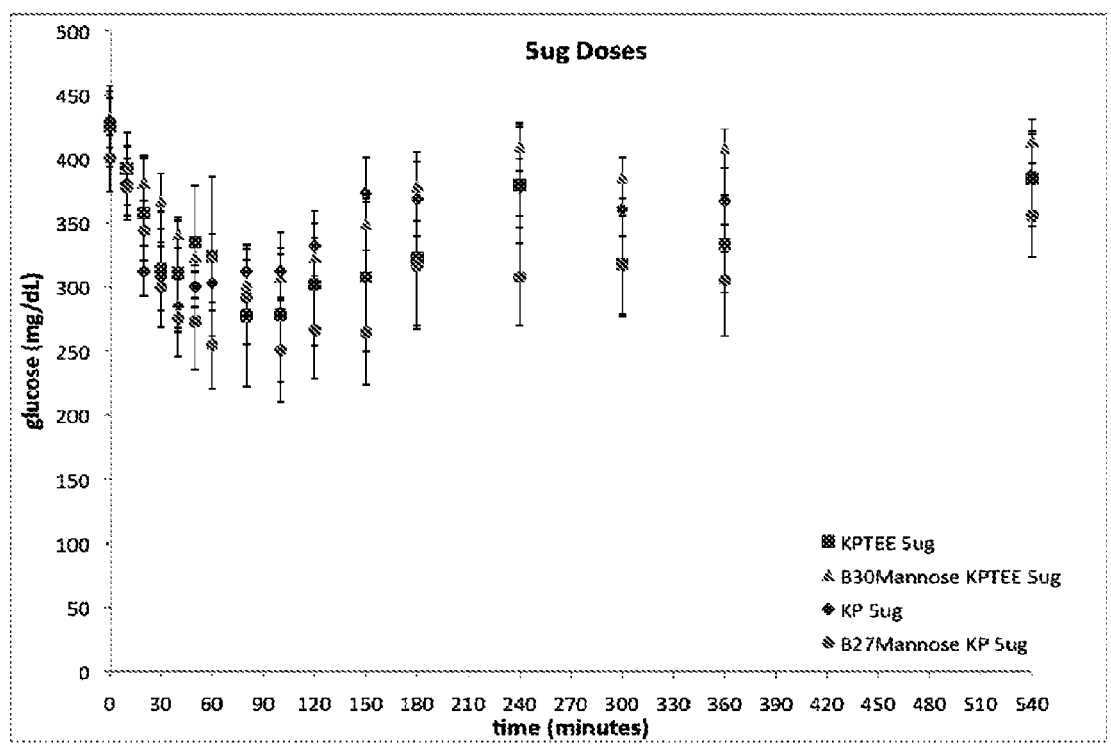
FIG. 7A provides the results of biological testing of low-dose mannosyl-modified insulin analogues in rats (5 μg per rat) rendered diabetic by steptozotocin. The following analogues were tested: α-D-mannopyranoside-$O^β$-$Thr^{B27}$-KP-insulin (in relation to control KP-insulin) and [$Glu^{B31}$, $Glu^{B32}$]-extended α-D-mannopyranoside-$O^β$-$Thr^{B30}$-KP-insulin (in relation to control [$Glu^{B31}$, $Glu^{B32}$]-extended KP-insulin; designated "KPEE"). The X-axis indicates time in minutes following subcutaneous injection of an insulin analog; the Y-axis provides the blood glucose concentration at that time. Symbols are defined within the panel. The potency and pharmacokinetics of KP-insulin in the STZ Sprague-Dawley rat model are indistinguishable from those of wild-type human insulin. A dose of 5 μg per rat corresponds to ca. 50% of maximal potency.
Figure 7B:
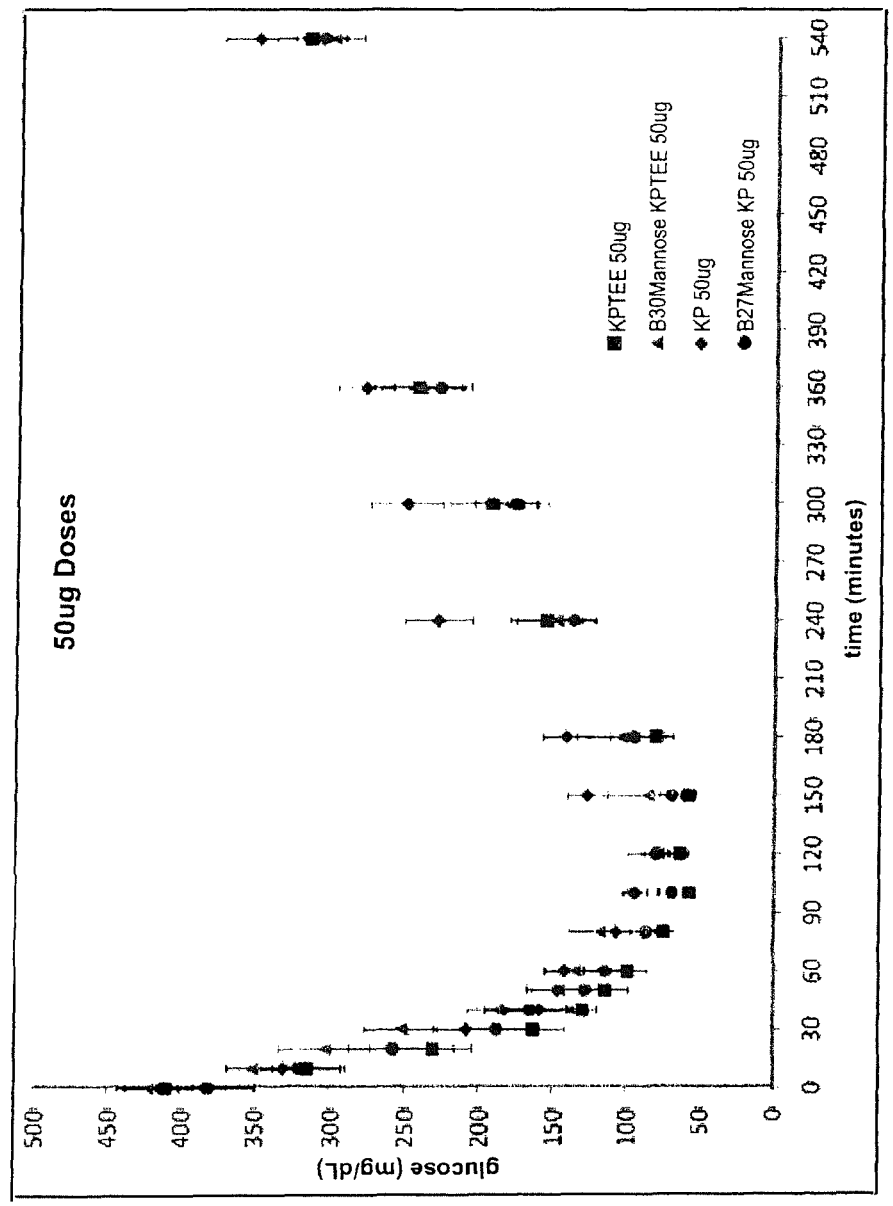
FIG. 7B provides the results of biological testing of high-dose mannosyl-modified insulin analogues (50 μg per rat) in rats rendered diabetic by steptozotocin. Symbols and axes are as in FIG. 7A. In dose-response studies of wild-type human insulin in this rat model, a dose of 50 μg per rat corresponds to the plateau value of maximal potency.
Figure 8A:
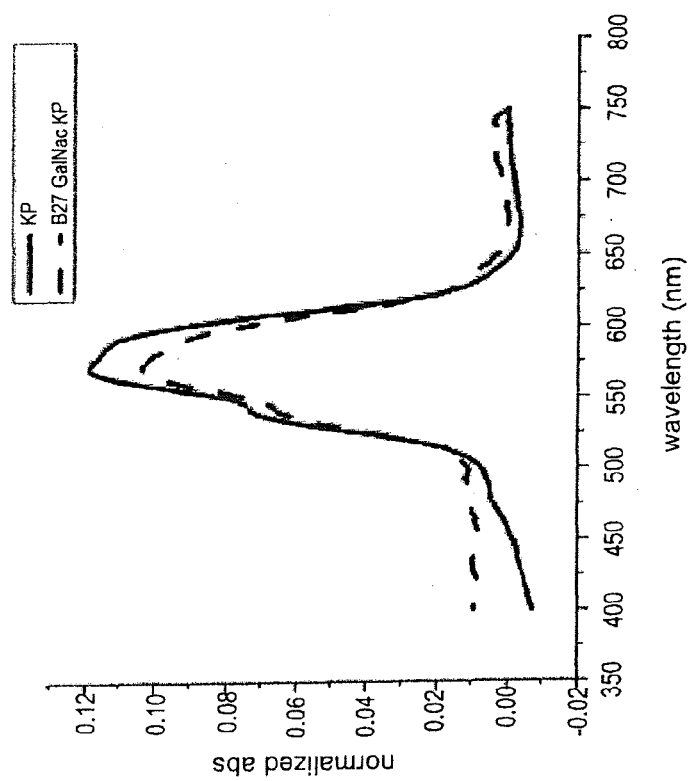
FIG. 8 presents an assay that probes the rate of disassembly of cobalt insulin analogue hexamers. (A and B) Baseline visible absorption spectra of phenol-stabilized cobalt insulin hexamers in the $R_6$ state due to d-d transitions in bound $Co^{2+}$ ions in tetrahedral environment: (A) α-D-mannopyranoside-$O^β$-Thr$^{B27}$-KP-insulin (dashed line) versus KP-insulin (solid line); and (B) N-acetyl-β-D-galactopyranoside-$O^β$-Thr$^{B27}$-KP-insulin (dashed line) versus KP-insulin (solid line). These data demonstrate that the Thr$^{B27}$-modified analogues retain competence to form metal-ion-stabilized $R_6$ hexamers. (C and D) EDTA sequestration assays. Time-dependent attenuation of the $R_6$-state-specific $Co^{2+}$-absorption band following addition of an excess of ETDA: (C) mannosyl-Thr$^{B27}$-KP-insulin (doted line) versus KP-insulin (dashed line) and wild-type insulin (solid line); and (D) N-acetyl-β-D-galactopyranoside-$O^β$-Thr$^{B27}$-KP-insulin (dotted line) versus KP-insulin (solid line). These data demonstrate that the monosaccharide modifications of Thr$^{B27}$ each lead to accelerated hexamer disassembly.

To evaluate the biological activity and potency of the analogues in an animal model, male Sprague-Dawley rats (mean body mass ~300 grams) were rendered diabetic by treatment with streptozotocin (STZ). Protein solutions containing KP-insulin or an analogues of KP-insulin were prepared using a protein-free sterile diluent (obtained from Eli Lilly and Co.) composed of 16 mg glycerin, 1.6 mg meta-cresol, 0.65 mg phenol, and 3.8 mg sodium phosphate pH 7.4. The activity of α-D-mannopyranoside-O$^\beta$-Thr$^{B27}$-KP-insulin was evaluated relative to its parent KP-insulin. Similarly, the activity of α-D-mannopyranoside-O$^\beta$-Thr$^{B30}$-[Glu$^{B31}$, Glu$^{B32}$]-KP-insulin relative to its parent [Glu$^{B31}$, Glu$^{B32}$]-KP-insulin. These formulations of KP-insulin or KP-insulin analogues were injected subcutaneously, and resulting changes in blood glucose concentration were monitored by serial measurements using a clinical glucometer (Hypoguard Advance Micro-Draw meter). To ensure uniformity of formulation, insulins were each re-purified by reverse-phase HPLC, dried to powder, dissolved in diluent at the same maximum protein concentration (300 µg/mL) and re-quantified by analytical C4 rp-HPLC; dilutions were made using the above buffer. Rats were injected subcutaneously at time t=0 with 5 or 50 µg insulin or insulin analogs in 100 µl of buffer per 300 g rat. The lower dose corresponds to ca. 17 µg/kg body weight, which in international units (IU) implies 0.5 IU/kg body weight. Dose-response studies of wild-type insulin indicated that at this dose the rate of glucose disposal during the first hour following injection was half maximal; the higher dose lies on the maximal plateau. Blood was obtained from the clipped tip of the tail at time 0 and every 10 minutes up to 90 min. The efficacy of insulin was calculated using (a) the change in concentration over time (using least-mean squares and initial region of linear fall) divided by the concentration of insulin injected and (b) the integrated area between the glucose time dependence and a horizontal line at the starting blood glucose concentration. Assessment of statistical significance was performed using a Student's t-test. Results at low and high doses are shown in FIGS. 7A and 7B, respectively. The histogram in FIG. 7C provides a summary of biological response rates during the first 60 minutes. Remarkably, α-D-mannopyranoside-O$^\beta$-Thr$^{B27}$-KP-insulin was found to be more active than its parent KP-insulin. Analogue α-D-mannopyranoside-O$^\beta$-Thr$^{B30}$-[Glu$^{B31}$, Glu$^{B32}$]-KP-insulin was also found to be more active than KP-insulin but similar to its parent [Glu$^{B31}$, Glu$^{B32}$]-KP-insulin. FIGS. 8 and 9 provide respective studies of in vitro receptor binding and hypoglycemic potency in STZ rats for derivatives of KP-insulin containing glucose-related carbohydrate modifications: β-D-glucopyranoside-O$^\beta$Thr$^{B27}$KP-insulin (N=3) and α-D-mannopyranoside-O$^\beta$-Thr$^{B27}$-β-D-glucopyranoside-O$^\beta$-Thr$^{B30}$-[Glu$^{B31}$, Glu$^{B32}$]-KP-insulin (N=5). Control assays were performed at the same time with KP-insulin (N=5) and -[Glu$^{B31}$, Glu$^{B32}$]-KP-insulin (N=5). Although the in vitro affinity of β-D-glucopyranoside-O$^\beta$-Thr$^{B27}$-KP-insulin for the insulin receptor is indistinguishable from that of KP-insulin (within experimental error; Table 1D), its apparent potency in STZ rats is reduced (FIG. 9), which may reflect decreased bioavailability due to binding to endogenous lectin-like molecules in the subcutaneous space.

The far-ultraviolet circular dichroism (CD) spectra of the B27 monosaccharide-linked analogue of KP-insulin are similar to those of the parent analogues. Free energies of unfolding ($\Delta G_u$) at 25° C. were estimated based on a two-state model as extrapolated to zero denaturant concentration; the denaturant was guanidine hydrochloride. The resulting estimates of $\Delta G_u$ were in each case similar to those of the parent analogues lacking a monosaccharide adduct. Estimates of free energies of unfolding and the mid-point concentration of guanidine hydrochloride ($C_{mid}$) for a subset of analogues are given in Table 2.

Physical stability was probed by measurement of lag times prior to onset of fibrillation as detected by enhancement of Thioflavin T fluorescence and visible cloudiness of the samples. Lag times thus indicate the time (in days) required for initiation of protein fibrillation on gentle agitation at 37° C. in zinc-free phosphate-buffered saline (pH 7.4). At least twofold extension of the lag times (corresponding to enhanced physical stability) was observed in comparative studies of N-acetyl-β-D-galactopyranoside-O$^\beta$-Thr$^{B27}$-Orn$^{B29}$-insulin relative to its parent Orn$^{B29}$-insulin and in studies of α-D-mannopyranoside-O$^\beta$-Thr$^{B27}$-KP-insulin relative to its parent KP-insulin. The lag time of (Glu$^{B31}$, Glu$^{B32}$)-extended KP-insulin is ca. threefold longer than that of KP-insulin and is not further prolonged by the B30 adduct α-D-mannopyranoside-O$^\beta$-Thr.

A method for treating a patient comprises administering an insulin analogue containing a monosaccharide adduct as known in the art or described herein. It is another aspect of the present invention that insulin analogues containing O-linked monosaccharide adducts at positions B27 and/or B30 may readily be obtained by semi-synthesis. This protocol employs tryptic digestion of a two-chain or single-chain precursor polypeptide following its folding to achieve native disulfide pairing, yielding a des-octapeptide[B23-B30] fragment of insulin or an insulin analogue containing additional substitutions in the A- and B chains. It is yet another aspect of the present invention that use of non-standard amino-acid substitutions enables a rapid and efficient method of preparation of monosaccharide-modified insulin analogues by trypsin-mediated semi-synthesis using unprotected octapeptides.

In still another example, the insulin analogue is administered by an external or implantable insulin pump. An insulin analogue of the present invention may also contain other modifications, such as a halogen atom at positions B24, B25, or B26 as described more fully in co-pending U.S. patent application Ser. No. 13/018,011, the disclosure of which is incorporated by reference herein. An insulin analogue of the present invention may also contain non-standard side chains position B24, such as Cyclohexanylalanine, 2-CH$_3$-Phe, 3-CH$_3$-Phe, or 4-CH$_3$-Phe as described more fully in co-pending U.S. Provisional Patent Application No. 61/507,324. An insulin analogue of the present invention may also contain a foreshortened B-chain due to deletion of residues B1-B3 as described more fully in co-pending U.S. Provisional Patent Application 61/589,012.

A surrogate marker for the pharmacokinetics of insulin hexamer disassembly (designated the EDTA sequestration assay) employs cobalt ions (Co$^{2+}$) rather than zinc ions (Zn$^{2+}$) to mediate hexamer assembly. Although Co$^{2+}$ and Zn$^{2+}$ hexamers are similar in structure, the cobalt ion provides a convenient spectroscopic probe due to its unfilled d-electronic shell. The principle of the assay is as follows. Solutions of R6 phenol-stabilized $Co^{2+}$ insulin hexamers are blue due to tetrahedral $Co^{2+}$ coordination; on disassembly the protein solution is colorless as octahedral $Co^{2+}$ coordination by water or EDTA (ethylene-diamine-tetra-acetic acid; a strong chelator of metal ions) lacks optical transitions at visible wavelengths as a consequence of ligand field theory. The EDTA sequestration assay exploits these spectroscopic features as follows. At time t=0 a molar excess of EDTA is added to a solution of R6 insulin hexamers or insulin analog hexamers. Although EDTA does not itself attack the hexamer to strip it of metal ions, any $Co^{2+}$ions released in the course of transient hexamer disassembly become trapped by the chelator and thus unavailable for reassembly. The rate of disappearance of the blue color (the tetrahedral d-d optical transition at 574 nm of the R-specific insulin-bound $Co^{2+}$) thus provides an optical signature of the kinetics of hexamer disassembly.

Figure 8B:
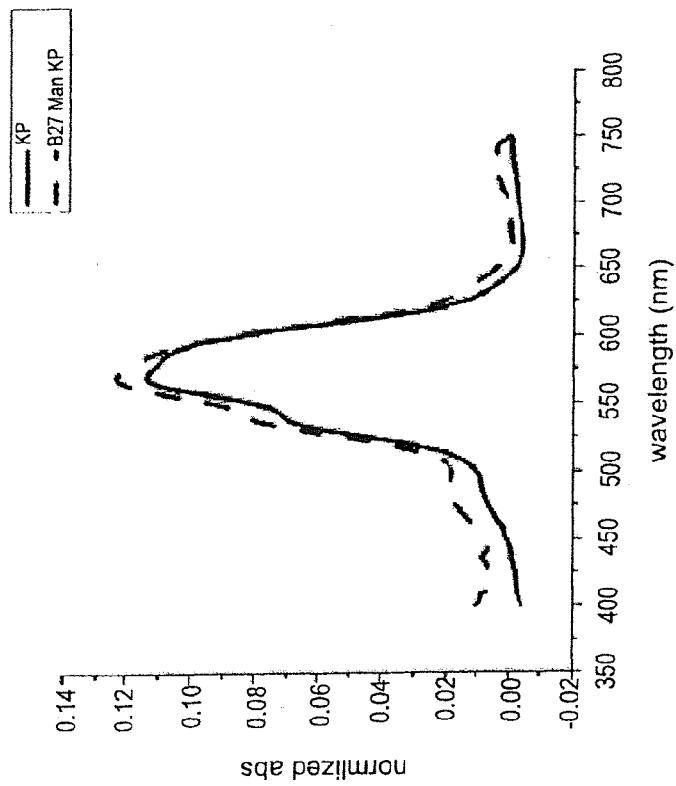
Figure 8D:
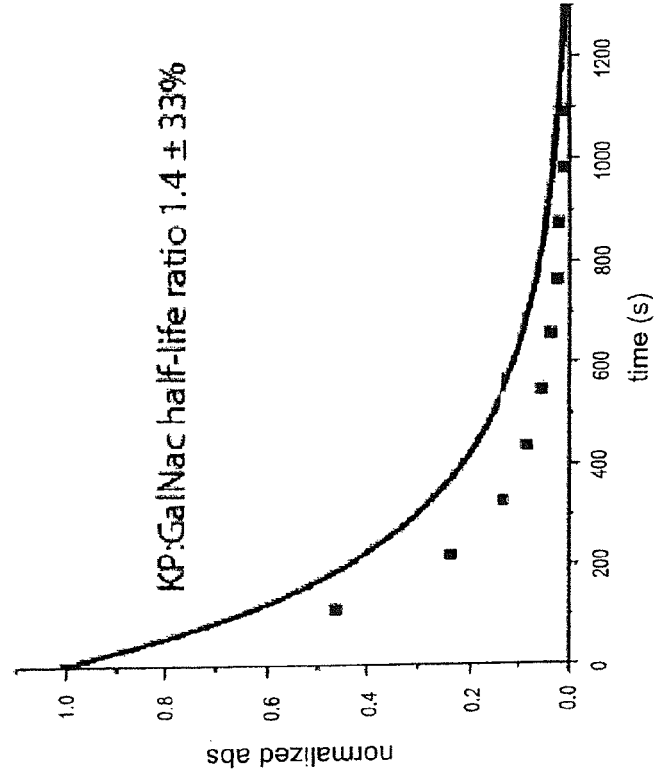
Figure 8C:
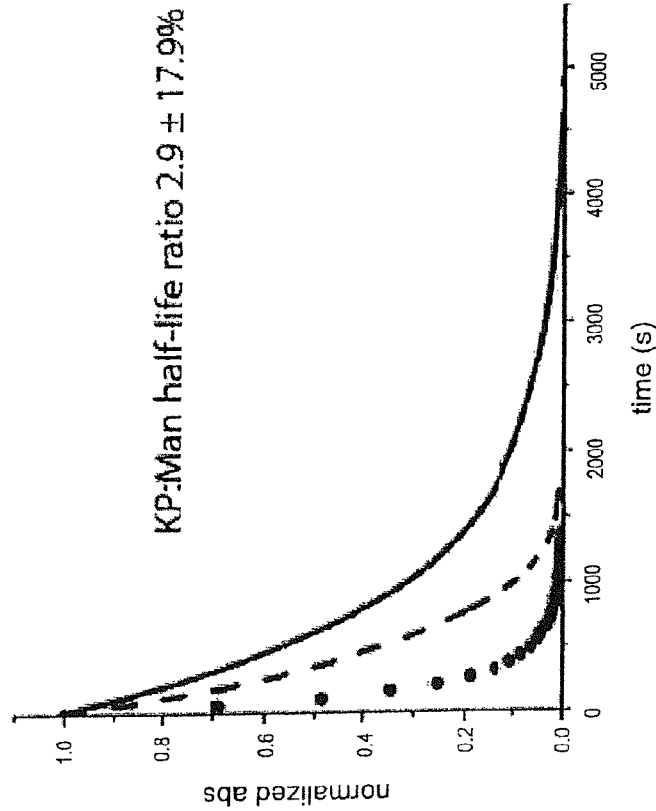
Figure 9:
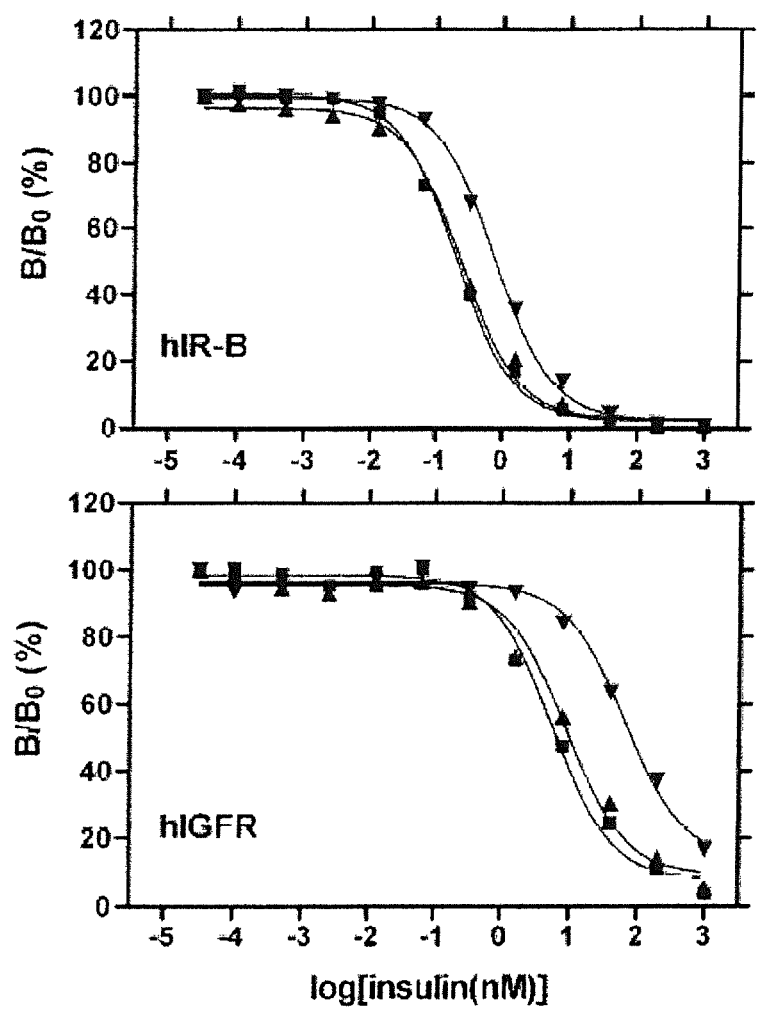
FIG. 9 is a graph showing the results of receptor-binding studies of insulin analogues. Studies of β-D-glucopyranoside-$O^β$-Thr$^{B27}$-KP-insulin versus KP-insulin by competitive displacement of (Upper Panel) $^{125}$I-Tyr$^{A14}$-labeled human insulin bound to isoform B of the human insulin receptor ("hIR-B" in figure) and (Lower Panel) $^{125}$I-Tyr31-labeled IGF-I bound to the Type I IGF Receptor (IGF-1R; "hIGFR"). Symbols: (■) KP-insulin, (▲) β-D-glucopyranoside-$O^β$-Thr$^{B27}$-KP-insulin, and (▼) [Glu$^{B31}$, Glu$^{B32}$]-extended α-D-mannopyranoside-$O^β$-Thr$^{B27}$-β-D-glucoopyranoside-$O^β$-Thr$^{B27}$-KP-insulin.
Figure 10:
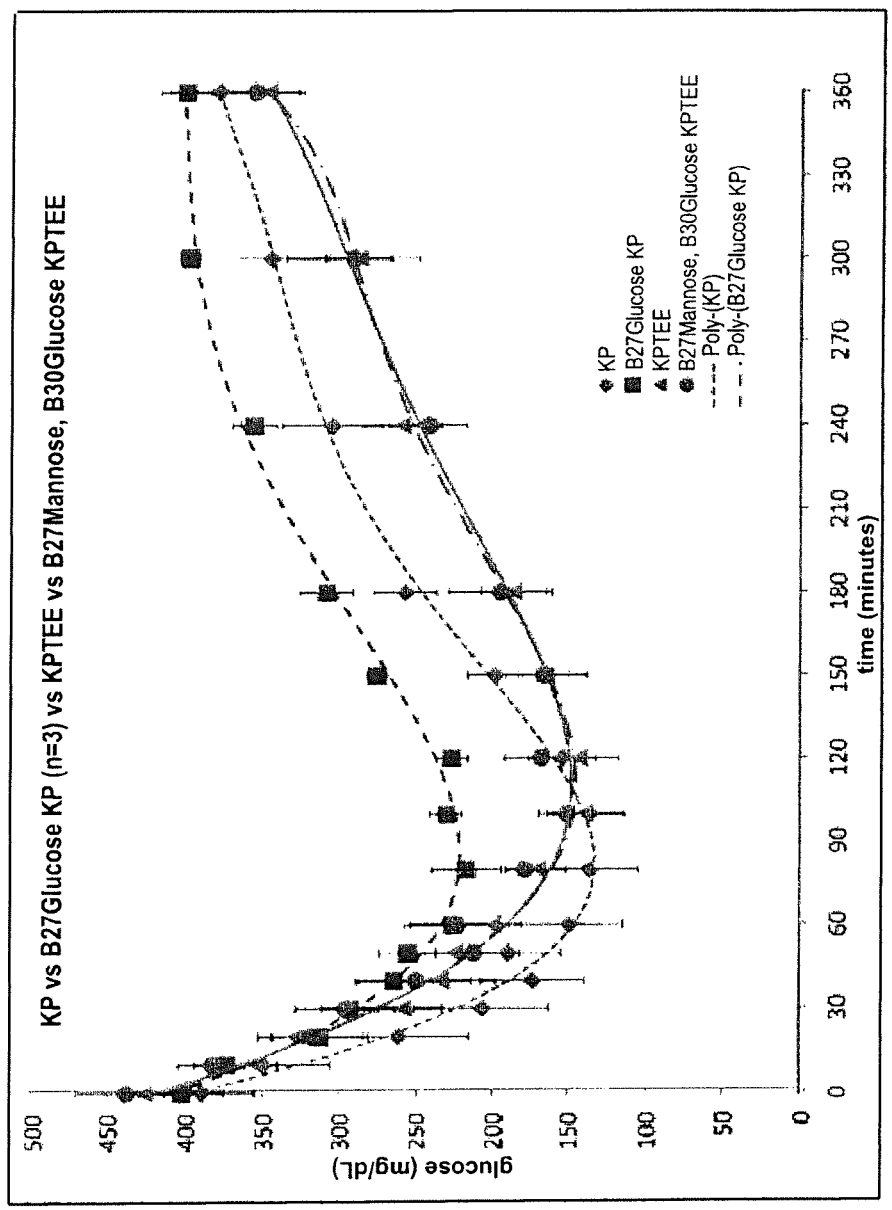
FIG. 10 provides the results of biological testing at medium-dose of monosaccharide-modified insulin analogues in rats (20 μg per rat) rendered diabetic by steptozotocin. The following analogues were tested: (filled squares) β-D-glucoopyranoside-$O^β$-Thr$^{B27}$-KP-insulin in relation to (filled diamonds) control KP-insulin; and (filled circles) [Glu$^{B31}$, Glu$^{B32}$]-extended α-D-mannopyranoside-$O^β$-Thr$^{B27}$-β-D-glucoopyranoside-$O^β$-Thr$^{B30}$-KP-insulin in relation to (filled triangles) [Glu$^{B31}$, Glu$^{B32}$]-extended KP-insulin; designated "KPTEE"). The X-axis indicates time in minutes following subcutaneous injection of an insulin analog; the Y-axis provides the blood glucose concentration at that time. Symbols are defined within the panel.
Figure 11:
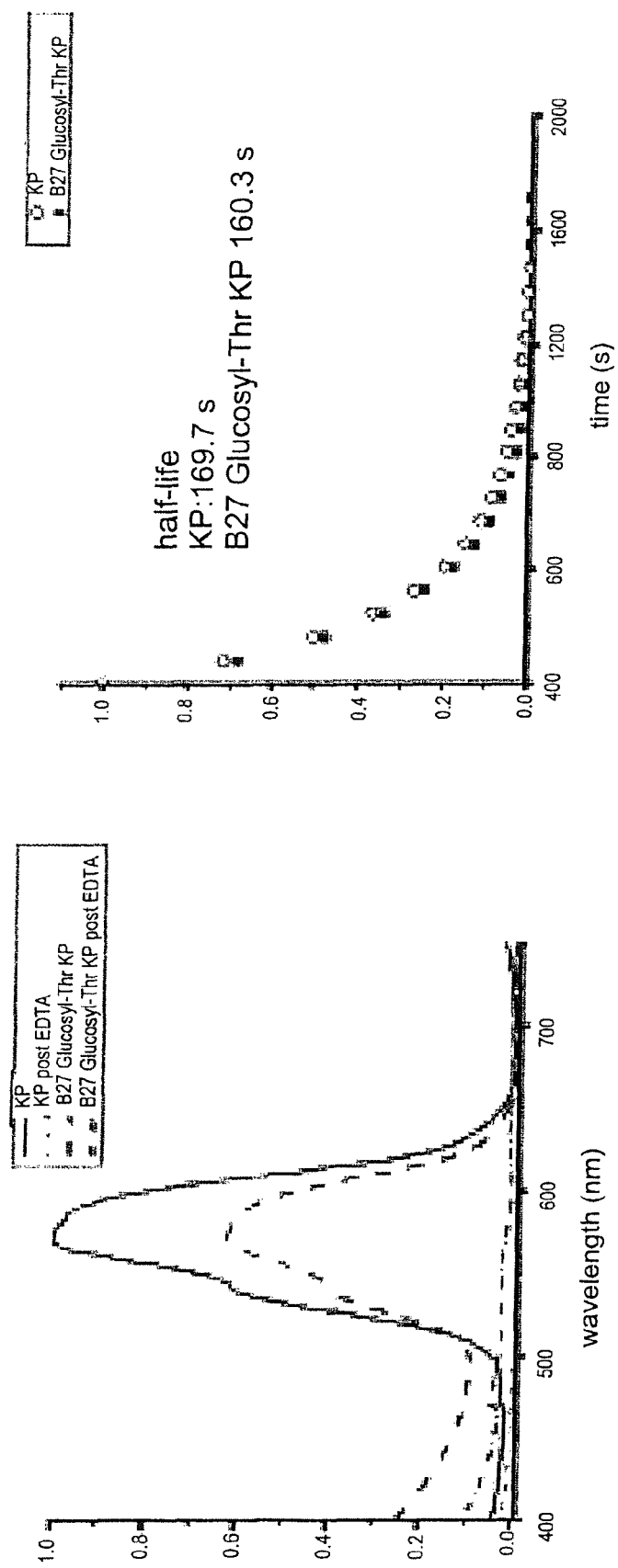
FIG. 11 presents an assay that probes the rate of disassembly of cobalt insulin analogue hexamers by the protocol illustrated in FIG. 8. (Left) Baseline visible absorption spectra of phenol-stabilized cobalt insulin hexamers in the $R_6$ state due to d-d transitions in bound $Co^{2+}$ ions in tetrahedral environment: (solid line) KP-insulin versus (dashed line) β-D-glucopyranoside-$O^β$-Thr$^{B27}$-KP-insulin; attenuation of the visible absorption peak was in each case observed following EDTA sequestration of the cobalt ions (dotted and dashed-dot lines). (Right) EDTA sequestration assays. Time-dependent attenuation of the $R_6$-state-specific $Co^{2+}$-absorption band following addition of an excess of ETDA: (open circles) KP-insulin versus (solid squares) β-D-galactopyranoside-$O^β$-Thr$^{B27}$-KP-insulin. These data demonstrate that this monosaccharide modification of Thr$^{B27}$ does not lead to accelerated hexamer disassembly.

EDTA assays were performed to compare the disassembly rate of α-D-mannopyranoside-$O^{\beta}$-$Thr^{B27}$-KP-insulin relative to the rates characteristic of its parent KP-insulin and wild-type human insulin (FIGS. 8A and 8C) and likewise to compare the disassembly rate of N-acetyl-β-D-galactopyranoside-$O^{\beta}$-$Thr^{B27}$-KP-insulin to that of KP-insulin (FIGS. 8B and 8D). Averaged traces of insulin cobalt solutions showing characteristic spectral profiles from 400-750 nm were first determined (FIGS. 8A and 8B). Samples were dissolved in 50 mM Tris (pH 7.4), 50 mM phenol, and 0.2 mM $CoCl_2$. NaSCN was then added to a final concentration of 1 mM. The kinetic studies of hexamer dissociation after addition of 2 mM EDTA as monitored at 574 nm (25° C. and pH 7.4) are also shown (FIGS. 8C and 8D), demonstrating that the α-D-mannopyranoside-$O^{\beta}$-$Thr^{B27}$ and N-acetyl-β-D-galactopyranoside-$O^{\beta}$-$Thr^{B27}$ in each case increase the rate of hexamer disassembly relative to that of KP-insulin (which in turn exhibits more rapid disassembly than wild-type insulin as expected). Such accelerated disassembly suggests that the B27 adducts may render the modified insulin lispro analogue formulations more rapid acting than Humalog after subcutaneous injection. In addition, the baseline optical absorption spectra of the hexameric cobalt complexes at t=0 are similar among all the samples. The similar shapes and magnitudes of these respective d-d electronic transitions imply that the metal ions are in similar R6-specific tetrahedral coordination sites in wild-type and variant hexamers. This result is significant as it implies that insulin analogues modified at B27 by an O-linked monosaccharide adduct remains competent for metal-ion-mediated assembly and hence a zinc-based formulation. Cobalt absorption studies of β-D-glucopyranoside-$O^{\beta}$-$Thr^{B27}$-KP-insulin by contrast yielded a visible absorption spectum whose d-d absorption band was approximately half as intensive as that of KP-insulin, suggesting formation of $T_3R^f_3$ hexamers rather than $R_6$ hexamers (FIG. 11, left). The kinetic stability of the modified hexamers was found to be essentially identical to that of KP-insulin (FIG. 11, right).

A pharmaceutical composition may comprise such insulin analogues and which may optionally include zinc. Zinc ions may be included in such a composition at a level of a molar ratio of between 2.2 and 3.0 per hexamer of the insulin analogue. In such a formulation, the concentration of the insulin analogue would typically be between about 0.1 and about 3 mM; concentrations up to 3 mM may be used in the reservoir of an insulin pump. Modifications of meal-time insulin analogues may be formulated as described for (a) "regular" formulations of Humulin® (Eli Lilly and Co.), Humalog® (Eli Lilly and Co.), Novalin® (Novo-Nordisk), and Novalog® (Novo-Nordisk) and other rapid-acting insulin formulations currently approved for human use, (b) "NPH" formulations of the above and other insulin analogues, and (c) mixtures of such formulations. Analogues of insulin lacking residues B1-B3 and containing $Glu^{B29}$ may also be formulated in the absence of zinc ions as known in the art for the formulation of insulin glulisine.

Excipients may include glycerol, glycine, arginine, Tris, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

Based upon the foregoing disclosure, it should now be apparent that insulin analogues provided will carry out the objects set forth hereinabove. Namely, these insulin analogues exhibit enhanced resistance to fibrillation while retaining desirable pharmacodynamic features (either rapid action or prolonged action as appropriate) and maintaining at least a fraction of the biological activity of wild-type insulin. It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Merrifield, R. B., Vizioli, L. D., and Boman, H. G. 1982. Synthesis of the antibacterial peptide cecropin A (1-33). *Biochemistry* 21: 5020-5031.

Mirmira, R. G., and Tager, H. S. 1989. Role of the phenylalanine B24 side chain in directing insulin interaction with its receptor: Importance of main chain conformation. *J. Biol. Chem.* 264: 6349-6354.

Sohma, Y., Hua, Q. X., Whittaker, J., Weiss, M. A. & Kent, S. B. H. 2010. Design and folding of [$Glu^{A4}(O^{\beta}$-$Thr^{B30})$]insulin ("Ester Insulin"): a minimal proinsulin surrogate chemically convertible to human insulin. *Angew. Chem. Int. Ed.* 49: 5489-5493

Sosnick, T. R., Fang, X., and Shelton, V. M. 2000. Application of circular dichroism to study RNA folding transitions. *Methods Enzymol.* 317: 393-409.

Wang, Z. X. 1995. An exact mathematical expression for describing competitive biding of two different ligands to a protein molecule *FEBS Lett.* 360: 111-114.

Weiss, M. A., Hua, Q. X., Jia, W., Chu, Y. C., Wang, R. Y., and Katsoyannis, P. G. 2000. Hierarchiacal protein "un-design": insulin's intrachain disulfide bridge tethers a recognition α-helix. *Biochemistry* 39: 15429-15440.

Whittaker, J., and Whittaker, L. 2005. Characterization of the functional insulin binding epitopes of the full length insulin receptor. *J. Biol. Chem.* 280: 20932-20936.

What is claimed is:

1. An insulin analogue comprising an insulin B-chain polypeptide modified with at least one of an O-linked monosaccharide pyranoside adduct at the side chain of residue B27 and an O-linked monosaccharide pyranoside adduct at the side chain of residue B30, relative to human insulin.

2. The insulin analogue of claim 1, wherein the at least one monosaccharide is selected from the group consisting of a manopyranoside, an N-acetyl-galactopyranoside, and a glucopyranoside.

3. An insulin analogue of claim 2, wherein the at least one monosaccharide adduct is located at position B27.

4. An insulin analogue of claim 3, wherein the at least one monosaccharide O-linkage has an alpha configuration.

5. An insulin analogue of claim 3, wherein the at least one monosaccharide O-linkage has a Beta configuration.

6. An insulin analogue of claim 2, wherein the at least one monosaccharide adduct is at position B30.

7. An insulin analogue of claim 6, wherein the monosaccharide O-linkage has an alpha configuration.

8. An insulin analogue of claim 6, wherein the monosaccharide O-linkage has a Beta configuration.

9. An insulin analogue of claim 6, additionally comprising a monosaccharide adduct located at position B27.

10. An insulin analogue of claim 2, wherein the at least one monosaccharide is linked to the side-chain oxygen atom of Threonine.

11. The insulin analogue of claim 2, wherein the insulin analogue additionally comprises the substitutions $Lys^{B28}$ and $Pro^{B29}$.

12. An insulin analogue of claim 2, wherein the B chain is additionally extended by $Glu^{B31}$ and optionally $Glu^{B32}$.

13. An insulin analogue of claim 2, wherein the insulin analogue additionally comprises $Orn^{B29}$.

14. An insulin analogue of claim 2 additionally comprising Histidine substitutions at positions A4 and A8 and a Glycine substitution at position A21.

15. An insulin analogue of claim 2, comprising a B chain polypeptide having the polypeptide sequence of SEQ ID NO: 7 and optionally an A chain polypeptide sequence of SEQ ID NO: 51.

16. An insulin analogue of claim 2, wherein the analogue is an analogue of a mammalian insulin.

17. A method of lowering the blood sugar of a patient, the method comprising administering a physiologically effective amount of an insulin analogue or a pharmaceutically acceptable salt thereof to the patient, wherein the insulin analogue or a pharmaceutically acceptable salt thereof contains a B-chain polypeptide modified by at least one of an O-linked monosaccharide at position B27 and an O-linked monosaccharide at position B30.

18. The method of claim 17, wherein the at least one monosaccharide is selected from the group consisting of a manopyranoside, an N-acetyl-galactopyranoside, and a glucopyranoside.

19. The method of claim 18, wherein the B chain is additionally extended by $Glu^{B31}$ and optionally $Glu^{B32}$.

20. A peptide containing an N-terminal glycine and one or two O-linked monosaccharide adducts selected from the group consisting of SEQ ID NOS: 54, 62 and 63.

* * * * *